(12) United States Patent
Pringle

(10) Patent No.: US 7,629,497 B2
(45) Date of Patent: Dec. 8, 2009

(54) MICROWAVE-BASED RECOVERY OF HYDROCARBONS AND FOSSIL FUELS

(75) Inventor: Frank G. Pringle, Medford, NJ (US)

(73) Assignee: Global Resource Corporation, Mount Laurel, NJ (US)

( * ) Notice: Subject to any disclaimer, the term of this patent is extended or adjusted under 35 U.S.C. 154(b) by 269 days.

(21) Appl. No.: 11/610,823

(22) Filed: Dec. 14, 2006

(65) Prior Publication Data

US 2007/0131591 A1 Jun. 14, 2007

Related U.S. Application Data

(60) Provisional application No. 60/750,098, filed on Dec. 14, 2005.

(51) Int. Cl.
*C10G 1/10* (2006.01)
*C10G 1/00* (2006.01)

(52) U.S. Cl. ............. 585/241; 204/157.43; 204/158.21; 204/157.15; 208/402; 588/219; 588/310; 219/690; 219/748

(58) Field of Classification Search ................. 208/402; 204/157.15, 157.43, 158.21; 588/310, 319, 588/405, 408–409, 900, 219; 219/690, 748
See application file for complete search history.

(56) References Cited

U.S. PATENT DOCUMENTS

| | | | |
|---|---|---|---|
| 2,757,738 A | 8/1956 | Ritchey | |
| 3,170,519 A | 2/1965 | Haagensen | 166/60 |
| 3,449,213 A * | 6/1969 | Ellis, Jr. et al. | 201/19 |
| 3,566,066 A | 2/1971 | Borthwick | 219/10.55 |
| 4,123,230 A | 10/1978 | Kirkbride | 44/1 R |
| 4,153,533 A | 5/1979 | Kirkbride | 208/11 R |
| 4,279,722 A * | 7/1981 | Kirkbride | 204/157.15 |
| 4,376,034 A | 3/1983 | Wall | 208/11 R |
| 4,408,999 A | 10/1983 | Nadkarni et al. | 44/1 SR |
| 4,419,214 A | 12/1983 | Balint et al. | 208/8 R |
| 4,647,443 A | 3/1987 | Apffel | 423/449 |
| 4,740,270 A | 4/1988 | Roy | 201/35 |
| 4,817,711 A | 4/1989 | Jeambey | 166/248 |
| 4,839,021 A | 6/1989 | Roy | 208/13 |
| 4,912,971 A | 4/1990 | Jeambey | 73/151 |
| 5,055,180 A | 10/1991 | Klaila | 208/402 |
| 5,084,140 A | 1/1992 | Holland | 201/19 |
| 5,087,436 A | 2/1992 | Roy | 423/461 |
| 5,099,086 A | 3/1992 | Roy | 585/1 |
| 5,167,772 A | 12/1992 | Parker, Sr. | 202/105 |
| 5,208,401 A | 5/1993 | Roy | 585/1 |
| 5,229,099 A | 7/1993 | Roy | 423/461 |
| 5,242,245 A | 9/1993 | Schellstede | 405/128 |
| 5,321,222 A | 6/1994 | Bible et al. | 219/745 |
| 5,330,623 A | 7/1994 | Holland | 201/19 |
| 5,364,821 A | 11/1994 | Holland | 502/5 |
| 5,366,595 A | 11/1994 | Padgett et al. | 201/19 |
| 5,387,321 A | 2/1995 | Holland | |
| 5,390,861 A | 2/1995 | Bishop | 241/24 |
| 5,451,297 A | 9/1995 | Roy | 201/25 |
| 5,470,384 A | 11/1995 | Cha et al. | 106/284.03 |
| 5,507,927 A | 4/1996 | Emery | 204/157.43 |
| 5,521,360 A | 5/1996 | Johnson et al. | 219/709 |
| 5,578,700 A | 11/1996 | Hunt et al. | 528/501 |
| 5,589,599 A | 12/1996 | McMullen et al. | 585/240 |
| 5,720,232 A | 2/1998 | Meador | 110/346 |
| 5,735,948 A | 4/1998 | Cha et al. | 106/724 |
| 5,836,524 A | 11/1998 | Wang | 241/23 |
| 5,876,684 A | 3/1999 | Withers et al. | 423/445 B |
| 5,877,395 A | 3/1999 | Emery | 588/900 |
| 6,097,985 A | 8/2000 | Kasevich et al. | 607/102 |
| 6,302,898 B1 | 10/2001 | Edwards et al. | 606/214 |
| 6,427,089 B1 | 7/2002 | Knowlton | 607/101 |
| 6,590,042 B1 | 7/2003 | Tang | 525/332.6 |
| 6,693,265 B1 | 2/2004 | Bell et al. | 219/686 |
| 7,101,463 B1 | 9/2006 | Weinecke et al. | |
| 7,101,464 B1 | 9/2006 | Pringle | 202/113 |
| 2004/0031731 A1 | 2/2004 | Honeycutt et al. | 208/402 |
| 2004/0074759 A1* | 4/2004 | Purta et al. | 204/157.15 |
| 2004/0253166 A1 | 12/2004 | Kruesi | 423/445 R |

FOREIGN PATENT DOCUMENTS

| | | |
|---|---|---|
| DE | 43 27 958 C1 | 11/1994 |
| DE | 196 31 201 A1 | 2/1998 |
| EP | 0 601 798 A1 | 6/1994 |
| FR | 2 799 763 | 4/2001 |

(Continued)

OTHER PUBLICATIONS

U.S. Appl. No. 11/610,962, filed Dec. 14, 2006, Pringle.

(Continued)

*Primary Examiner*—Glenn A Caldarola
*Assistant Examiner*—Brian McCaig
(74) *Attorney, Agent, or Firm*—Woodcock Washburn LLP

(57) ABSTRACT

The present invention provides methods for decomposing and extracting compositions for the recovery of petroleum-based materials from composites comprising those petroleum-based materials, comprising subjecting the compositions and/or composites to microwave radiation, wherein the microwave radiation is in the range of from about 4 GHz to about 18 GHz. The present invention also provides for products produced by the methods of the present invention and for apparatuses used to perform the methods of the present invention.

27 Claims, 35 Drawing Sheets

FOREIGN PATENT DOCUMENTS

| WO | WO 85/04893 A1 | 11/1985 |
| WO | WO 91/03281 A1 | 3/1991 |
| WO | WO 01/03473 A1 | 1/2001 |
| WO | WO 01/12289 A1 | 2/2001 |
| WO | WO 03/016826 A2 | 2/2003 |

OTHER PUBLICATIONS

Depew, M.C., et al., "Microwave induced catalytic decomposition of some Alberta oil sands and bitumens," *Research on Chemical Intermediates*, 1991, 16(3), 213-223.

Domínguez, A., et al., "Investigations into the characteristics of oils produced from microwave pyrolysis of sewage sludge," Fuel Processing Technology, 2005, 86, 1007-1020.

Domínguez, A., et al., "Gas chromatographic-mass spectrometric study of the oil fractions produced by microwave-assisted pyrolysis of different sewage sludges," J. of Chromatography A, 2003, 1012, 193-206.

Gasner, L.L., et al., "Microwave and conventional pyrolysis of a bituminous coal," Chem. Eng. Commun., 1986, 48, 1-6.

Kamci, O., et al., "Brown coal conversion by microwave plasma reactions under successive supply of methane," Fuel, 1998, 77(13), 1503-2506.

Menéndez, J.A., et al., "Microwave-induced drying, pyrolysis and gasification (MWDPG) of sewage sludge: vitrification of the solid residue," J. Anal. Appl. Pyrolysis, 2005, 74, 406-412.

Menéndez, J.A., et al., "Microwave pyrolysis of sewage sludge: analysis of the gas fraction," J. Anal. Appl. Pyrolysis, 2004, 71, 657-667.

Tanner, D.D., et al., "The catalytic conversion of $C_1$-$C_n$ hydrocarbons to olefins and hydrogen: microwave-assisted C-C and C-H bond activation," Energy & Fuels, 2001, 15, 197-204.

"A microwave oven for oil shale," *Access to Energy newsletter Archive*, 1975, http://www.accesstoenergy.com/view/atearchive/s76a3826.htm.

Behringer, M., "Tires can help make the environment go 'round," *Market Plus J.*, Summer 1998, 23-27.

Bows, J.R., "Variable frequency microwave heating of food," *J. Microw. Power Electromagn. Energy*, 1999, 34(4), 227-238 (Abstract, 1 page).

"Carbon Recovery Corporation—executive summary," *Carbon Recovery Corporation*, http://www.carbonrecovery.com/Executive_Summary.html, downloaded from the internet on Sep. 14, 2006, 7 pages.

Copty, A., et al., "Low-power near field microwave applicator for localized heating of soft matter," Appl. Phys. Lett., 2004, 84(25), 5109-5111.

Coulter, P.E., "Synopsis of scrap rubber reclamation in Canada," *North American Recycled Rubber Association*, http://www.p2pays.org/ref/11/10504/html/biblio/htmls/prh3.htm, downloaded from the internet on Jul. 27, 2005, 2 pages.

DeKok, D., "Microwaves extract tough-to-reach oil," *The Patriot-News*, 2006, http://www.pennlive.com/printer/printer.ssf?/base/business/1158367209289720.xml, downloaded from the internet on Sep. 18, 2006, 2 pages.

Finden, S., et al., "Microwave technology," 2005, http://www.ife.no/main_subjects_new/energy_environment/microwaves, downloaded from the internet on Jan. 11, 2007, 3 pages.

"Frequently asked questions," *Environmental Waste International*, 2001, http://www.ewmc.com/FAQs/FAQs.html, downloaded from the internet on Jul. 27, 2005.

Krauss, C., "The cautious U.S. boom in oil shale," *The New York Times*, Dec. 21, 2006, Late Edition, Section C, col. 5, p. C1 and 5.

Ku, H.S., et al., "Variable frequency microwave processing of thermoplastic composites," *ISSN*, 2000, 29(6), 278-284.

"Microwave reduction of medical waste and tires," *OCDTA Environmental Technology Profiles Catalogue*, 2000, http://www.oceta.on.ca/profiles/EWI/ewi_tech.html, downloaded from the internet on Jul. 27, 2005, 6 pages.

"Microwave properties," *Environmental Waste International*, 2001, http://www.ewmc.com/Technology/Technology_microwave.html, downloaded from the internet on Jan. 12, 2007, 2 pages.

Napoli, A., et al., "Scrap tyre pyrolysis: are the effluents valuable products?," *J. of Analytical and Applied Pyrolysis*,, 1997, 373-382.

"Oil shale technology assessment," *Oil Shale Resources Technology & Economics* ,, 1991, vol. II, 7-8, B4-B5.

"Oil recovery from fractured reservoirs using microwave heating," http://www.tudelft.nl/live/binaries/b2eaf5b5-68a9-4a11-9db8-a91d9e56914e/doc/HB-microwave.pdf , downloaded from the internet on Jan. 31, 2007, 2 pages.

Pringle, F., "Striking oil—in a landfill," *Business, The Philadelphia Inquirer*, 2004, 2 pages.

Roy, C., et al., "Vacuum pyrolysis of used tires," 1995, http://www.p2pays.org/ref/11/10504/html/biblio/html4/pyh3.htm, downloaded from the internet on Jul. 27, 2005, 10 pages.

"Waste tire recycling, contents and subject index and pyrolysis," http://www.p2pays.org/ref/11/10504/html/summary/sindex.htm, downloaded from the internet on Jul. 27, 2005, 6 pages.

"What is reverse polymerization?," *Environmental Waste International*, 2001, http://www.ewmc.com/Technology/Technology_rev_polymerization.html, downloaded from the internet on Jan. 12, 2007, 2 pages.

Whittaker, G., "A basic introduction to microwave chemistry," 1997, http://homepages.ed.ac.uk/ah05/basicintro.html, downloaded from the internet on Jan. 11, 2007, 3 pages.

Kiser, J.V.L., "Scrap-Tire Pyrolysis—the Impossible Dream?" Scrap, Sep./Oct. 2002, 34-41.

Pacella, R.M., Popular Science, "Best of What's New—2007 Green Tech PopSci Innovator: Frank Pringle", Dec. 2007, downloadable from http://www.popsci.com/popsci/flat/bown/2007/innovator_2.html.

Time Magazine, "The Best Inventions of the Year: Recovering Lost Oil", Nov. 12, 2007, p. 88.

\* cited by examiner

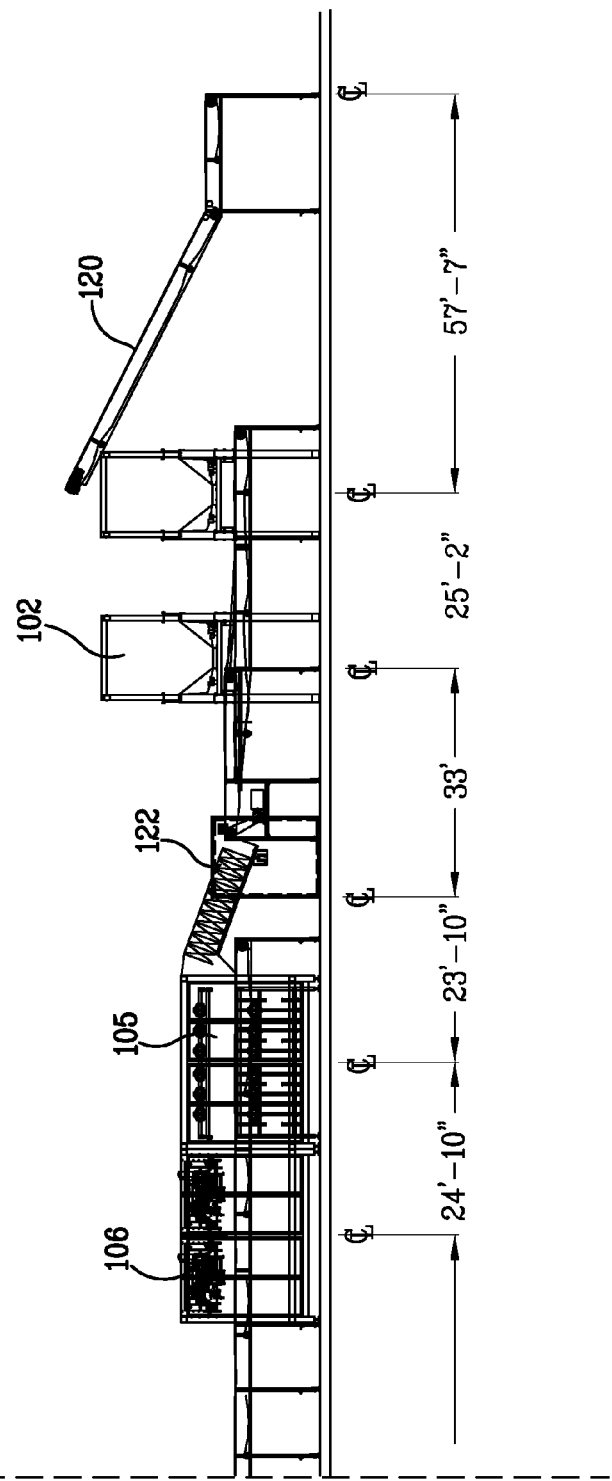

On Site Fractionalizing

Pyrolytic Carbon Black (1st Stage)
(Electron Microscope Photograph 60,000x magnification)

Pyrolytic Carbon Black (2nd Stage)
(Electron Microscope Photograph 60,000x magnification)

Pyrolytic Carbon Black (Final)
(Electron Microscope Photograph 60,000x magnification)

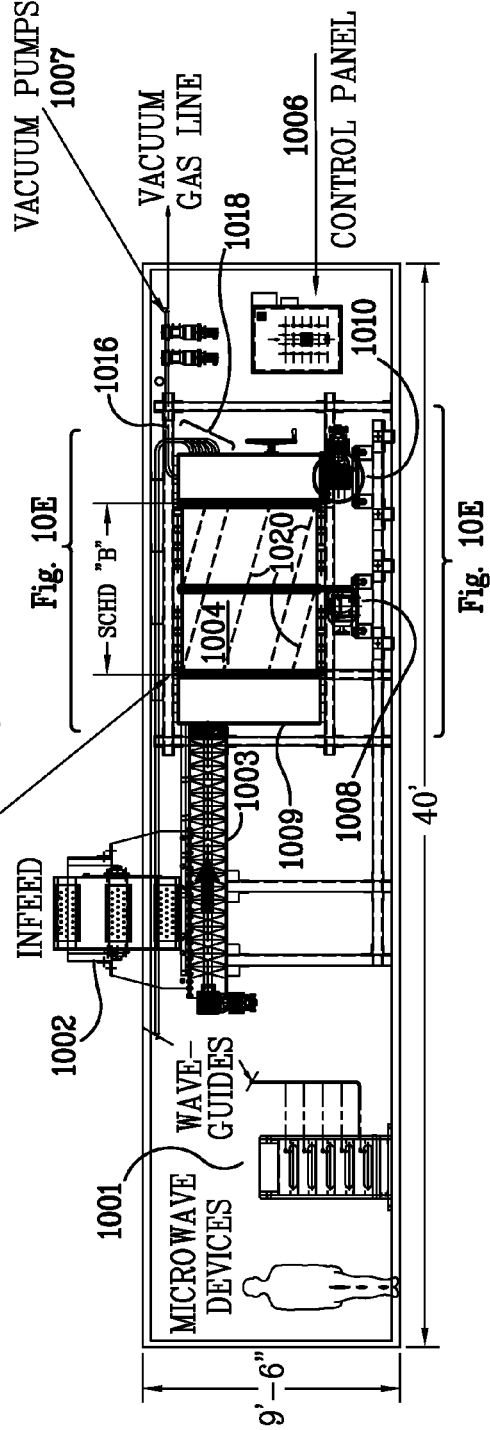
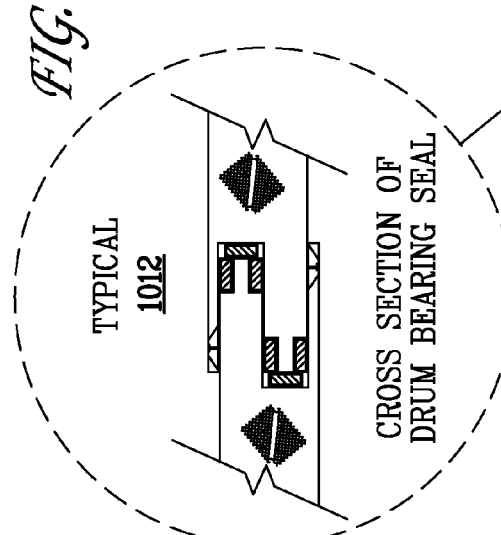

MICROWAVE-BASED RECOVERY OF HYDROCARBONS AND FOSSIL FUELS

CROSS-REFERENCE TO RELATED APPLICATIONS

This application claims the benefit of U.S. Provisional Patent Application No. 60/750,098, "Method for Using Microwave Radiation", filed Dec. 14, 2005, the entirety of which is incorporated by reference herein.

FIELD OF THE INVENTION

The present invention relates to methods and apparatuses for using microwave radiation and more particularly, to methods and apparatuses for decomposing compositions comprising petroleum-based materials.

BACKGROUND OF THE INVENTION

Petroleum-based materials are integral to the world's economy and demand for such fuels and consumer products is increasing. As the demand rises, there is a need to efficiently and economically extract petroleum-based materials to fulfill that demand. As such, it would be advantageous to not only be able to extract petroleum-based materials from the earth, but to also recycle consumer products to recapture those petroleum-based materials.

Worldwide oil consumption is estimated at seventy-three million barrels per day and growing. Thus, there is a need for sufficient oil supplies. Tar sands, oil sands, oil shales, oil cuttings, and slurry oil contain large quantities of oil, however, extraction of oil from these materials is costly and time-consuming and generally does not yield sufficient quantities of usable oil.

Soil contaminated with petroleum products is an environmental hazard, yet decontamination of petroleum-tainted soil is time-consuming and expensive.

Furthermore, it has been estimated that 280 million gallons of oil-based products such as plastics go into landfills each day in the United States. It would be desirable to recapture and recycle the raw materials of these products.

Scrap vehicle tires are a significant problem worldwide and their disposal presents significant environmental and safety hazards, including fires, overflowing landfills, and atmospheric pollution. While there are a number of existing applications for these tires, including tire-derived fuels, road construction, and rubber products, these applications are insufficient to dispose of all the available scrap tires. The major components of tires are steel, carbon black, and hydrocarbon gases and oils, which are commercially desirable. As such, it is advantageous to develop processes for the recovery of these products from scrap vehicles tires. Prior art methods of decomposing scrap vehicle tires do not produce commercial-grade carbon black and require high temperatures and extended exposure times for recovery of the hydrocarbon components.

Efforts to recycle tires using microwave technology has been described in U.S. Pat. Nos. 5,507,927 and 5,877,395 to Emery. Efforts to recover petroleum from petroleum-impregnated media has been described in U.S. Pat. Nos. 4,817,711 and 4,912,971 to Jeambey. Efforts to decompose plastics using microwave radiation has been described in U.S. Pat. No. 5,084,140 to Holland. The prior work has involved the use of single-frequency microwave radiation. Single-frequency microwave radiation is a slow process that does not provide uniform heating. Moreover, single-frequency microwave radiation typically results in arcing on metal components.

Thus, there is a need for methods and apparatuses for the recycling of petroleum-based compositions and for the recovery of petroleum-based materials from composites containing petroleum-based materials. The invention is directed to these and other important needs.

SUMMARY OF THE INVENTION

The present invention provides methods for decomposing compositions comprising carbon-based materials comprising subjecting the compositions to microwave radiation for a time sufficient to at least partially decompose the composition, wherein the microwave radiation comprises at least one frequency component in the range of from about 4 GHz to about 18 GHz.

The present invention provides methods for decomposing compositions comprising petroleum-based materials comprising subjecting the compositions to microwave radiation for a time sufficient to at least partially decompose the composition, wherein the microwave radiation comprises at least one frequency component in the range of from about 4 GHz to about 18 GHz.

The present invention further provides methods for recovery of petroleum-based materials from composites comprising those petroleum-based materials. The methods of the present invention include subjecting the composite to microwave radiation for a time sufficient to extract the petroleum-based material, wherein the microwave radiation comprises at least one frequency component in the range of from about 4 GHz to about 18 GHz.

The present invention also provides for products produced by the methods of the present invention.

The present invention additionally provides apparatuses for decomposing compositions comprising petroleum-based materials. The apparatuses of the present invention comprise a microwave radiation generator, wherein the generator is capable of applying microwave radiation characterized as having at least one frequency component in the range of from 4 GHz to about 18 GHz, and at least one container to collect decomposed components from the compositions. The present invention further provides apparatuses for extracting petroleum-based materials from composites comprising the petroleum-based material. These apparatuses comprise a microwave radiation generator, wherein the generator is capable of applying microwave radiation characterized as having at least one frequency component in the range of from 4 GHz to about 18 GHz, and at least one container to collect decomposed components from the composite.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIGS. 1A-1G illustrate an embodiment of the present invention directed to processing tire cuttings using microwaves to recover fuel oil;

FIG. 4A illustrates an elevation view of a microwave reactor system suitable for processing shale rock, tar sands, drill cuttings, and the like;

FIGS. 10A-10E illustrate an additional embodiment of a drum reactor system for processing materials containing hydrocarbons.

DETAILED DESCRIPTION OF ILLUSTRATIVE EMBODIMENTS

Figure 1B:
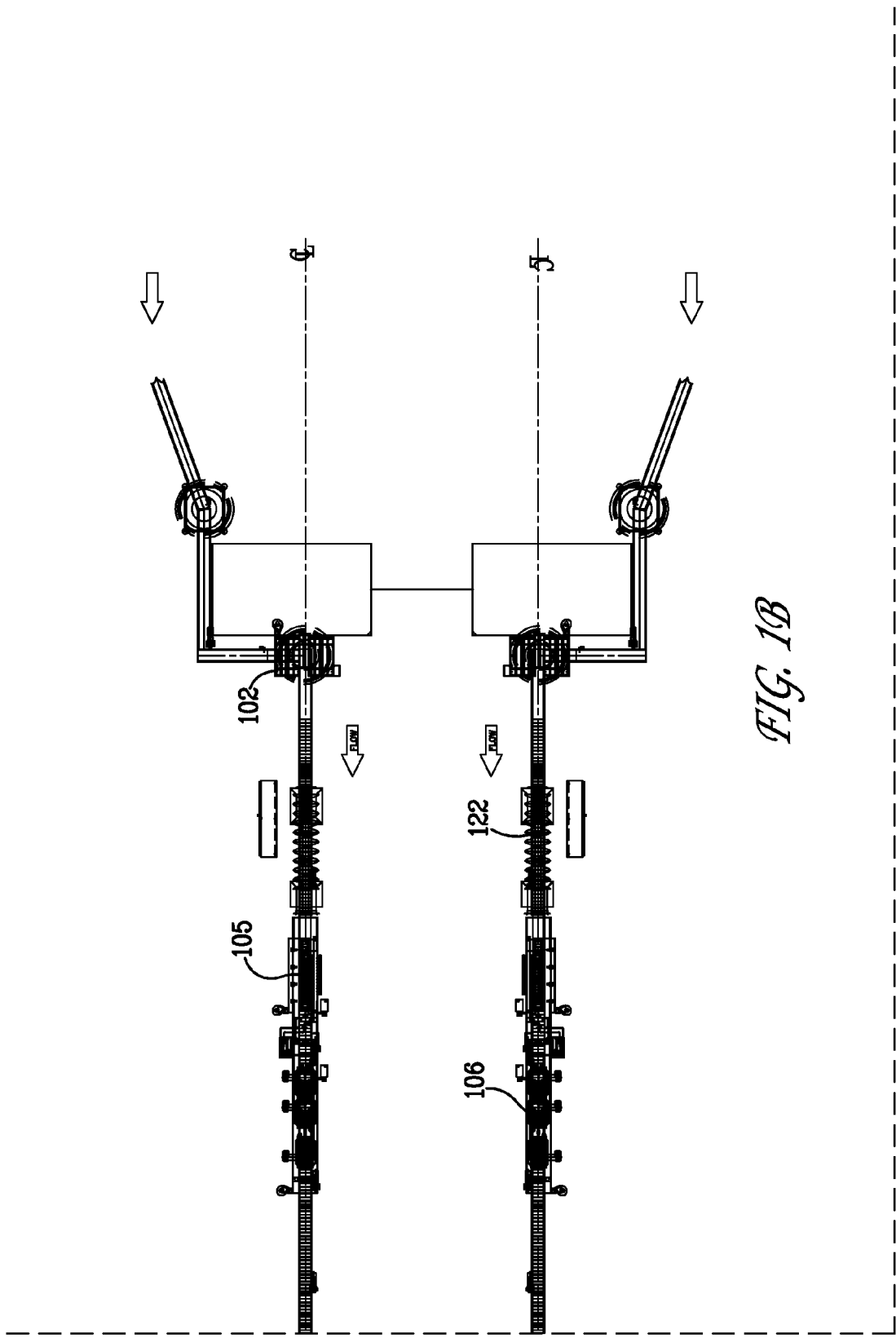

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

"Sweeping," as the term is used herein, is defined as the application of a plurality of radiation frequencies over a period of time.

"Pulsing," as used herein, means subjecting the composition to microwave radiation for a period of time, followed by periods of time wherein the composition is not subjected to microwave radiation.

"Oil," as used herein, means any hydrocarbon or petroleum-based oil.

"Gas," as used herein, includes any hydrocarbon-based material that is in the gaseous state at atmospheric temperature and pressure and includes, but is not limited to, methane, ethane, propane, butane, isobutene, or mixtures thereof.

"Carbon black," as used herein, includes any grade of commercially-acceptable carbon black, including, but not limited to, rubber black.

"Oil sands," also known as "tar sands," are deposits of bitumen, a heavy black viscous oil.

"Oil shale" is sedimentary rock containing a high proportion of Kerogen, which, when heated, can be converted into oil.

"Slurry oil" is refinery waste oil.

"Oil cuttings" are the waste product generated during the drilling of oil wells. Examples of oil cuttings include, but are not limited to, bits and pieces of oil-soaked soil and rock.

"Hydrocarbons" are compositions that comprise carbon and hydrogen.

"Carbon-based" refers to matter that comprises carbon.

"Decompose" and "decomposing" refers to a process whereby matter is broken down to smaller constituents. For example, solids can be broken down into particles, liquids, vapors, gases, or any combination thereof, rubbery materials can be broken down into liquids, vapors, gases, or any combination thereof, viscous liquids can be broken down to lower viscosity liquids, vapors, gases, or any combination thereof, liquids can be broken down to vapors, gases, or any combination thereof; composite materials comprising inorganic solids and trapped organic matter can be broken down to inorganic solids and released organic vapors and gases, and the like.

1 Torr=1 mm Hg=1 millimeter mercury.

Methods for decomposing compositions comprising petroleum-based materials are set forth herein. The compositions used in the present invention contemplate any composition comprised of petroleum-based, carbon-based and various hydrocarbon materials. The petroleum-based materials may be present in the composition in amounts ranging from about 1% to 100%, by weight, based on the weight of the composition. Preferably, the composition is a vehicle tire. In other embodiments, the composition comprises plastic, which includes, but is not limited to ethylene (co)polymer, propylene (co)polymer, styrene (co)polymer, butadiene (co)polymer, polyvinyl chloride, polyvinyl acetate, polycarbonate, polyethylene terephthalate, (meth)acrylic (co)polymer, or a mixture thereof. A variety of natural and synthetic resins and rubbers can also be decomposed according to the methods described herein. Various carbon-based materials that can also be processed according to the inventions described herein include coal, such as anthracite coal and bituminous coal.

In one embodiment, the composition is subjected to microwave radiation for a time sufficient to at least partially decompose the composition. The microwave radiation can be in the range of from about 4.0 and about 12.0 GHz. Other ranges can also be used, for example, in the range of from about 4 GHz to about 18 GHz, and more preferably in the range of from about 12 GHz to about 18 GHz. For example, coal can be processed at frequencies in the range of from about 4 GHz to about 18 GHz, and more preferably in the range of from about 12 GHz to about 18 GHz.

In one embodiment, the composition is subjected to one or more pre-selected microwave radiation frequencies. Preferably, the pre-selected microwave radiation frequency will be the resonating microwave frequency, i.e, the microwave radiation frequency at which the composition absorbs a maximum amount of microwave radiation. It has been determined that different compositions of the present invention will absorb more or less microwave radiation, depending on the frequency of the microwave radiation applied. It has also been determined that the frequency at which maximum microwave radiation is absorbed differs by composition. By using methods known in the art, a composition of the present invention can be subjected to different frequencies of microwave radiation and the relative amounts of microwave radiation absorbed can be determined. Preferably, the microwave radiation selected is the frequency that comparatively results in the greatest amount of microwave radiation absorption. In one embodiment, microwave radiation frequency resulting in a comparative maximum absorption of microwave radiation by the compositions of the present invention is in the range of from about 4.0 and about 12.0 GHz. In others, particularly with respect to vehicle tires, the microwave radiation frequency resulting in a comparative maximum absorption of microwave radiation by the compositions of the present invention is in the range of from about 4.0 and about 7.2 GHz. In yet others, the microwave radiation frequency resulting in a comparative maximum absorption of microwave radiation by the compositions of the present invention is in the range of from about 4.0 and about 6.0 GHz.

The present invention also provides methods for subjecting a composition to a sweeping range of microwave radiation frequencies for a time sufficient to at least partially decompose the composition. Preferably, variable frequency microwave ("VFM") is used to sweep the compositions. VFM is described in U.S. Pat. No. 5,321,222 to Bible, et al. and U.S. Pat. No. 5,521,360 to Johnson, et al., incorporated herein by reference in their entireties. Unlike single frequency microwave radiation, VFM produces a bandwidth of microwave radiation frequencies that are applied sequentially to the composition. Consequentially, the field distribution with VFM is substantially more uniform than the field distribution of single microwave frequency radiation. The more uniform field distribution of VFM produces fewer hot spots, resulting in more uniform heating of the composition. Moreover, generally, no single frequency is applied for longer than about 25 µs. The short duration of each applied frequency produces no build-up of charge, thus eliminating discharge, or arcing, typically observed during single frequency microwave irradiation.

In some embodiments, particularly with respect to vehicle tires, the range of microwave radiation frequencies swept is in the range of from about 4.0 GHz to about 12.0 GHz. In certain embodiments, the range of microwave radiation frequencies swept is in the range of from about 5.8 GHz to about 7.0 GHz. In still others, the range of microwave radiation frequencies swept is in the range of from about 7.9 GHz and 8.7 GHz. In some embodiments, range of microwave radiation frequencies is in the C-Band frequency range, the C-Band frequency range encompassing microwave frequencies in the range of from about 4.0 GHz to about 8.0 GHz. In other embodiments, the range of microwave radiation frequencies is in the X-Band frequency range, the X-band frequency range encompassing microwave frequencies in the range of from about 8.0 GHz to about 12.0 GHz.

Preferably, the sweeping of the range of microwave radiation frequencies encompasses a pre-selected, resonating microwave radiation frequency characterized as having at least one frequency component in the range of from about 4.0 GHz to about 12.0 GHz. This frequency can be selected by using the methods described herein and techniques known in the art. Preferably, the bandwidth of the sweeping range of microwave radiation is about 4.0 GHz. More preferably, the range of microwave frequencies with which the composition is swept, is about ±2 GHz of the pre-selected microwave radiation frequency. For example, if the pre-selected microwave radiation frequency is 7.2 GHz, the composition would be swept with the range of microwave radiation frequencies encompassing from about 5.2 to about 9.2 GHz. The microwave frequencies can also be swept at about ±1.5 GHz, or even ±1.0 GHz, or even ±0.5 GHz of the preselected microwave frequency.

Upon decomposition of the compositions subjected to the methods and apparatuses of the invention, flammable hydrocarbon-based gases are released. To reduce the risk of ignition, it is preferred that the method be performed in an oxygen-deprived atmosphere. Preferably, the composition is exposed to less than about 12% oxygen. More preferably, the composition is exposed to less than about 8% oxygen. Even more preferably, the composition is exposed to less than about 5% oxygen.

In one embodiment, the composition is exposed an inert gas atmosphere. Preferably, the inert gas is nitrogen, argon, or mixtures thereof.

In some embodiments, the composition is exposed to less than atmospheric pressure. Preferably, the composition is exposed to less than about 40 Torr. More preferably, the composition is exposed to less than about 20 Torr. Even more preferably, the composition is exposed to less than about 5 Torr. Without being bound by any particular theory or operation, it is believed that operating at sub-atmospheric pressures helps to recover hydrocarbon-based gases and prevents overheating.

In one embodiment, the composition of the present invention forms a vehicle tire. Using the methods of the present invention, the tire can be decomposed to produce at least one of oil, gas, steel, sulfur, and carbon black.

Over-exposure to microwave radiation and over-heating of the composition of the present invention may result in the recovery of non-commercially-acceptable carbon black. Controlling the temperature of the composition during microwave irradiation prevents such over-exposure and over-heating to produce commercially-acceptable carbon black. Preferably, the temperature of the composition does not exceed about 700° F. More preferably, the temperature of the composition does not exceed about 500° F. Even more preferably, the temperature of the composition does not exceed about 465° F.

In one embodiment, the temperature of the composition can be controlled while performing the method of the present invention by pulsing the microwave radiation subjection. For example, microwave radiation can be applied until the composition temperature reaches about 465° F., at which time, the application of microwave radiation can be stopped for a time sufficient for the composition to cool between about 5 to 25 degrees. Once the composition has cooled, the application of microwave radiation can be resumed. This process can be repeated, as necessary, until the composition is sufficiently decomposed.

Decomposition products obtained from the compositions using the methods of the present invention may be refined and/or purified using techniques known in the art.

The present invention also provides methods for extracting petroleum-based materials from composites comprising the petroleum-based materials by subjecting the composites to microwave radiation for a time sufficient to extract the petroleum-based material. Preferably, the microwave radiation is in the range of from about 4.0 and about 12.0 GHz.

The composites are any material comprising petroleum-based materials, including, but not limited to, at least one of oil sands, oil shale, slurry oil, oil cuttings, and soil or sand contaminated with petroleum-based materials. As used herein, "composites" also includes, but is not limited to, oil wells.

In one embodiment, the composite is subjected to one or more pre-selected microwave radiation frequencies. Preferably, the pre-selected microwave radiation frequency will be the resonating microwave frequency, i.e, the microwave radiation frequency at which the composite absorbs a maximum amount of microwave radiation. It has been determined that different composites of the present invention will absorb more or less microwave radiation, depending on the frequency of the microwave radiation applied. It has also been determined that the frequency at which maximum microwave radiation is absorbed differs by composite. By using methods known in the art, a composite of the present invention can be subjected to different frequencies of microwave radiation and the relative amounts of microwave radiation absorbed can be determined. Preferably, the microwave radiation selected is the frequency that comparatively results in the greatest amount of microwave radiation absorption. In one embodiment, microwave radiation frequency resulting in a comparative maximum absorption of microwave radiation by the composite of the present invention is in the range of from about 4.0 and about 12.0 GHz. In others, the microwave radiation frequency resulting in a comparative maximum absorption of microwave radiation by the composite of the present invention is in the range of from about 7.9 and about 12.0 GHz. In yet others, the microwave radiation frequency resulting in a comparative maximum absorption of microwave radiation by the composite of the present invention is in the range of from about 7.9 and about 8.7 GHz.

The present invention also provides methods for recovery of petroleum-based materials from composites comprising those petroleum-based materials, by subjecting the composite to a sweeping range of microwave radiation frequencies for a time sufficient to extract the petroleum-based material, and wherein the range of frequencies of the microwave radiation is in the range of from about 4.0 GHz to about 12.0 GHz. The composites are any material comprising petroleum-based materials, including, but not limited to, at least one of oil sands, oil shale, slurry oil, oil cuttings and soil or sand contaminated with petroleum-based materials.

Preferably, variable frequency microwave ("VFM") is used to sweep the composites. VFM is described in U.S. Pat. No. 5,321,222 to Bible, et al. and U.S. Pat. No. 5,521,360 to Johnson, et al., incorporated herein by reference in their entireties. Unlike single frequency microwave radiation, VFM produces a bandwidth of microwave radiation frequencies that are applied sequentially to the composite. Consequentially, the field distribution with VFM is substantially more uniform than the field distribution of single microwave frequency radiation. The more uniform field distribution of VFM produces fewer hot spots, resulting in more uniform heating of the composite. Moreover, generally, no single frequency is applied for longer than about 25 μsr, or no longer than about 20 μs, or no longer than about 15μs, or even no longer than about 10μs. The short duration of each applied frequency produces no build-up of charge, thus eliminating discharge, or arcing, typically observed during single frequency microwave irradiation.

In certain embodiments, the range of microwave radiation frequencies is in the range of from about 7.9 GHz to about 12.0 GHz. In still others, the range of microwave radiation frequencies is in the range of from about 7.9 GHz and 8.7 GHz. In some embodiments, range of microwave radiation frequencies is in the C-Band frequency range, the C-Band frequency range encompassing microwave frequencies in the range of from about 4.0 GHz to about 8.0 GHz. In other embodiments, the range of microwave radiation frequencies is in the X-Band frequency range, the X-band frequency range encompassing microwave frequencies in the range of from about 8.0 GHz to about 12.0 GHz.

Preferably, the sweeping of the range of microwave radiation frequencies encompasses one or more pre-selected microwave radiation frequencies in the range of from about 4.0 GHz to about 12.0 GHz. This frequency can be selected by using the methods described herein and techniques known in the art. In one embodiment, the pre-selected microwave radiation frequency is in the range of from about 7.9 and about 8.7 GHz. In other embodiments, the bandwidth of the sweeping range of microwave radiation is about 4.0 GHz. More preferably, the range of microwave frequencies with which the composition is swept, is about ±2 GHz of the pre-selected microwave radiation frequency. For example, if the pre-selected microwave radiation frequency is 7.2 GHz, the composition would be swept with the range of microwave radiation frequencies encompassing from about 5.2 to about 9.2 GHz.

Upon extraction, flammable hydrocarbon-based gases are released. To reduce the risk of ignition, it is preferred that the method be performed in an oxygen-deprived atmosphere. Preferably, the composite is exposed to less than about 12% oxygen. More preferably, the composite is exposed to less than about 8% oxygen. Even more preferably, the composite is exposed to less than about 5% oxygen.

In one embodiment, the composite is exposed to an inert gas atmosphere. Preferably, the inert gas is nitrogen, argon, or mixtures thereof.

In some embodiments, the composite is exposed to less than atmospheric pressure. Preferably, the composite is exposed to less than about 40 Torr. More preferably, the composite is exposed to less than about 20 Torr. Even more preferably, the composite is exposed to less than about 5 Torr.

In one embodiment, the composite is subjected to microwave radiation sufficient to heat the petroleum-based material to its boiling point temperature. Boiling point temperatures of petroleum-based materials are known in the art. Reducing the pressure at which the composite is exposed will result in a decrease in the boiling point temperature of the petroleum-based material. Those of skill in the art will be able to determine the boiling point temperatures of petroleum-based materials at different pressures.

In some embodiments, the methods of the present invention may be used in situ to extract petroleum-based materials from composites located in the field. In other embodiments, inert gases may be flowed, in situ, onto the composites. In one embodiment, the pressure surrounding the composite may be reduced to below atmospheric pressure.

Using the methods of the present invention, oil and/or gases can be recovered from the composite.

The petroleum-based material extracted using the methods of the present invention may be refined and/or purified using techniques known in the art.

The present invention also provides for apparatuses for decomposing a composition comprising a petroleum-based material. In one embodiment, the apparatuses of the present invention comprise a microwave radiation generator, wherein the generator is capable of applying microwave radiation characterized as having at least one frequency component in the range of from about 4.0 and about 12.0 GHz, and at least one container to collect decomposed components from the composition. In one embodiment, the microwave radiation generator is capable of applying a microwave radiation frequency between about 4.0 and about 12.0 GHz.

In other embodiments, the apparatuses of the present invention comprise a microwave radiation generator, wherein the generator is capable of applying a sweeping range of frequencies of microwave radiation characterized as having at least one frequency component in the range of from about 4.0 GHz to about 12.0 GHz, and at least one container to collect decomposed components from the composition. In other embodiments, microwave radiation generator is capable of applying sweeping microwave radiation in the C-Band frequency range. In yet other embodiments, microwave radiation generator is capable of applying sweeping microwave radiation in the X-Band frequency range. In yet other embodiments, microwave radiation generator is capable of applying sweeping microwave radiation in the Ku-Band frequency range (about 12 GHz to about 18 GHz). In further embodiments, the microwave radiation generator is capable of applying sweeping microwave radiation in the range of about 5.8 GHz to about 7.0 GHz. In yet other embodiments, the microwave radiation generator is capable of applying sweeping microwave radiation in the range of about 7.9 GHz to about 8.7 GHz.

In another embodiment, the chamber is open to the outside atmospheric conditions. In other embodiments, the chamber is closed to the outside atmosphere. In yet other embodiments, the chamber has an internal pressure of less than atmospheric pressure. Preferably, the chamber is capable of operating at a pressure of less than about 40 Torr. More preferably, the chamber is capable of operating at a pressure of less than about 20 Torr. Even more preferably, the chamber is capable of operating a pressure of less than about 5 Torr.

The present invention also provides for apparatuses for extracting a petroleum-based material from a composite comprising the petroleum-based material. In one embodiment, the apparatuses of the present invention comprise a microwave radiation generator, wherein the generator is capable of applying microwave radiation characterized as having at least one frequency component in the range of from about 4.0 GHz to about 12.0 GHz, and at least one container to collect the extracted petroleum-based material. In some embodiments, the microwave radiation generator is capable of applying a microwave radiation frequency of characterized as having at least one frequency component in the range of from about 4.0 and about 12.0 GHz.

In other embodiments, the apparatuses of the present invention comprise a microwave radiation generator, wherein the generator is capable of applying a sweeping range of frequencies of microwave radiation characterized as having at least one frequency component in the range of from about 4.0 GHz to about 12.0 GHz, and at least one container to collect the extracted petroleum-based material. In some embodiments, the microwave radiation generator is capable of applying sweeping microwave radiation in the C-Band frequency range. In yet other embodiments, microwave radiation generator is capable of applying sweeping microwave radiation in the X-Band frequency range. In further embodiments, the microwave radiation generator is capable of applying sweeping microwave radiation in the range of about 5.8 GHz to about 7.0 GHz. In yet other embodiments, the microwave radiation generator is capable of applying sweeping microwave radiation in the range of about 7.9 GHz to about 8.7 GHz.

In some embodiments, the apparatuses of the present invention may be used in situ to extracted petroleum-based materials from composites located in the field.

In other embodiments, the apparatuses further comprise at least one chamber for holding the composite. In another embodiment, the chamber is open to the outside atmospheric conditions. In other embodiments, the chamber is closed to the outside atmosphere. In yet other embodiments, the chamber has an internal pressure of less than atmospheric pressure. Preferably, the chamber is capable of operating at a pressure of less than about 40 Torr. More preferably, the chamber is capable of operating at a pressure of less than about 20 Torr. Even more preferably, the chamber is capable of operating at a pressure of less than about 5 Torr.

In other embodiments, the apparatuses further comprise at least one chamber for holding the composition. The volume of the compositions of the present invention may reduce during decomposition. In some embodiments, the chamber may have a conveyor having a perforated bottom such that decomposed materials may fall out of the chamber once reaching a particular size, so as not to over-expose the materials to microwave radiation. The conveyor may be adapted to be oscillated.

An exemplary embodiment of the present invention is depicted in FIGS. 1A-1G. FIGS. 1A-1G demonstrates one apparatus wherein tire fragments are placed on a first conveyor belt that carries the tire pieces through three, differently-sized chambers of the apparatus. In a first chamber, the tire pieces are exposed to microwave radiation using the methods described herein. As the tire fragments decompose, the smaller pieces will fall through perforations in the first conveyor and drop to a second conveyor. The second conveyor is not exposed to microwave radiation in the first chamber. The second conveyor carries the pieces to a second chamber, wherein they are exposed to microwave radiation using the methods described herein. As the pieces decompose, the smaller pieces fall through the perforations in the second conveyor to a third conveyor. The perforations in the second conveyor are smaller than the perforations in the first conveyor. The third conveyor is not exposed to microwave radiation in the second chamber. The third conveyor carries the pieces to a third chamber, wherein they are exposed to microwave radiation using the methods described herein. As the pieces decompose, the smaller pieces fall through the perforations in the third conveyor to a fourth conveyor. The perforations in the third conveyor are smaller than the perforations in the second conveyor. Decomposition will be essentially complete after exposure in the third chamber and the material remaining on the fourth conveyor will be mainly steel, carbon black, and ash, which can be further processed using techniques known in the art.

Figure 1C:
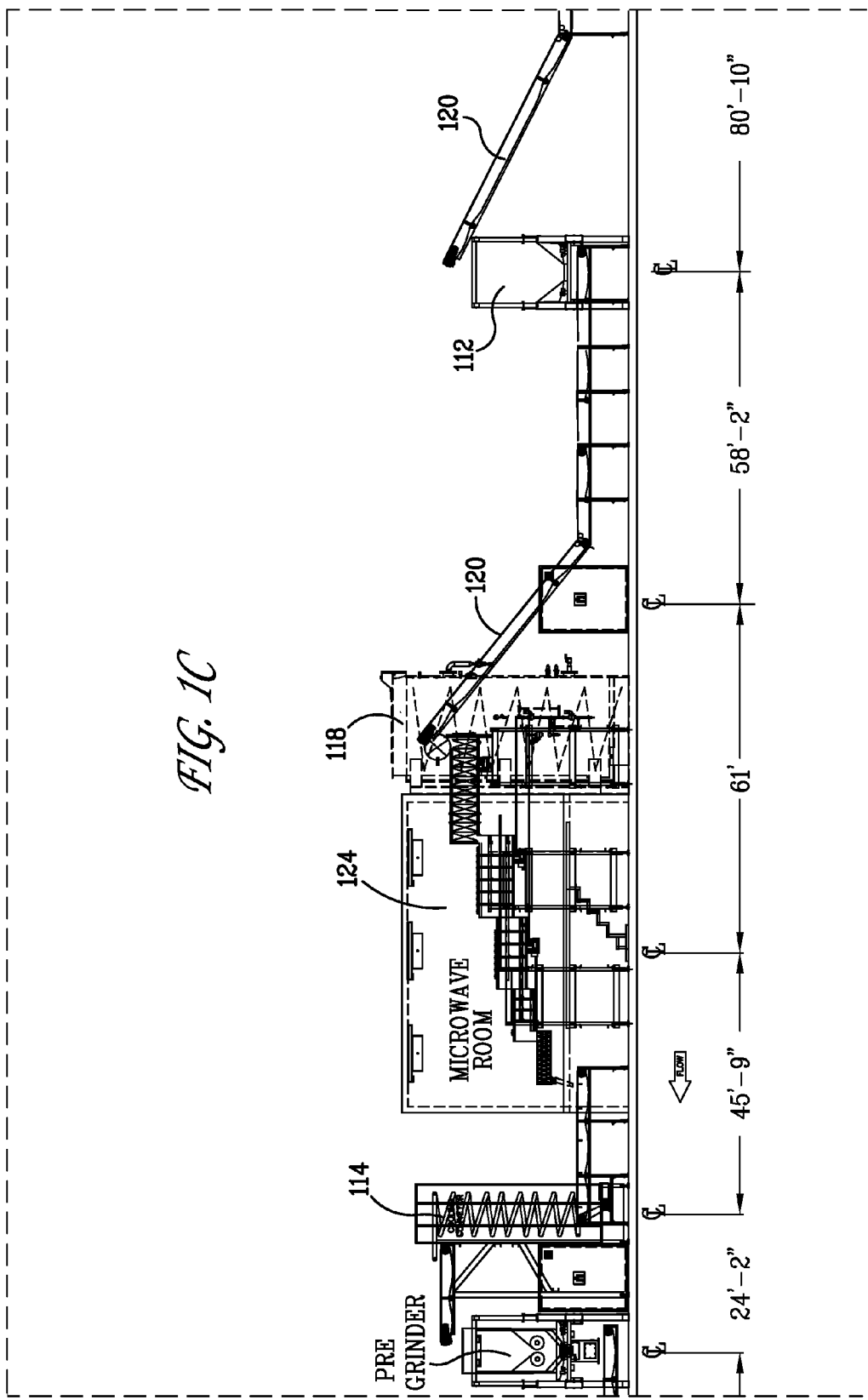
Figure 1D:
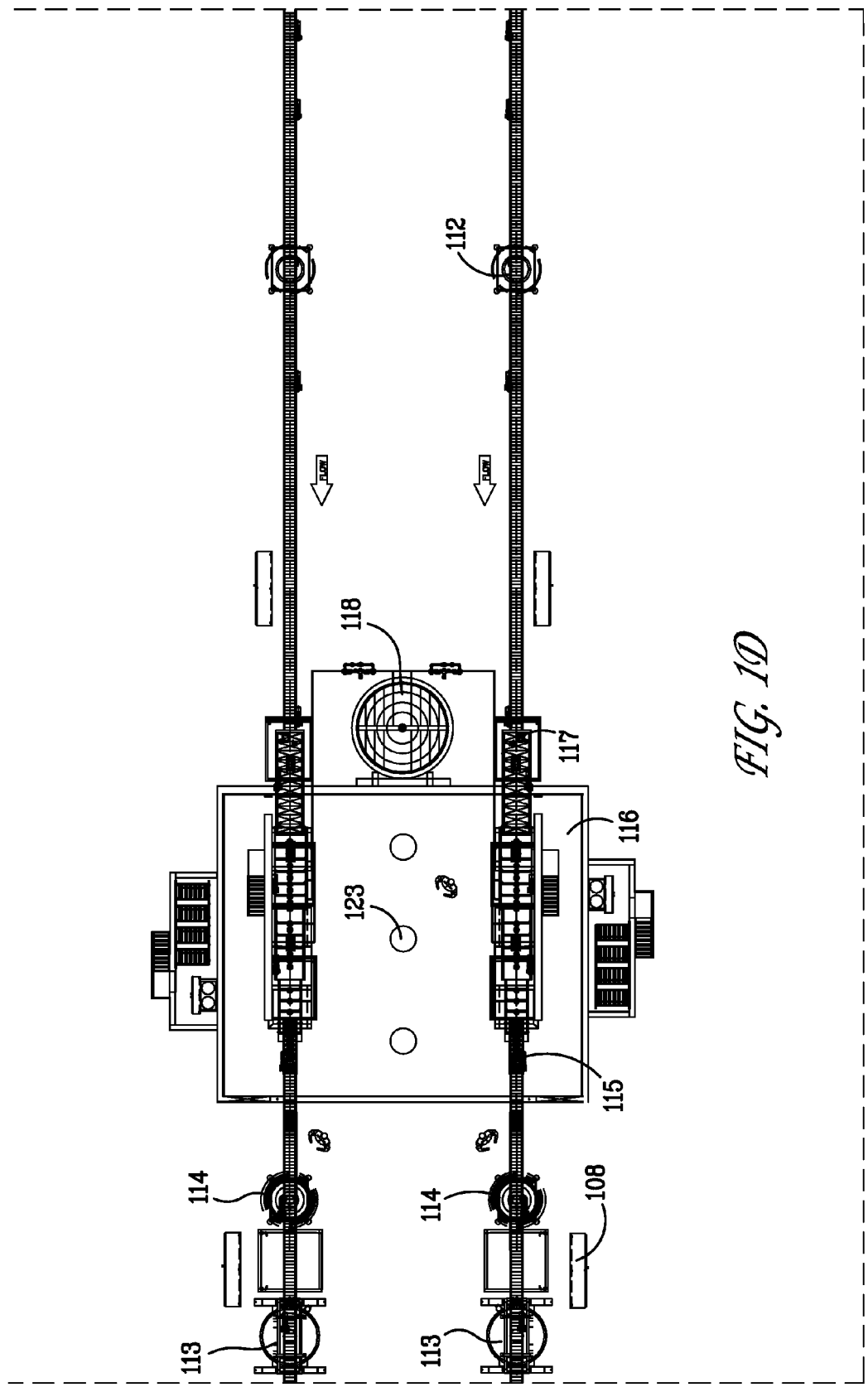
Figure 1E:
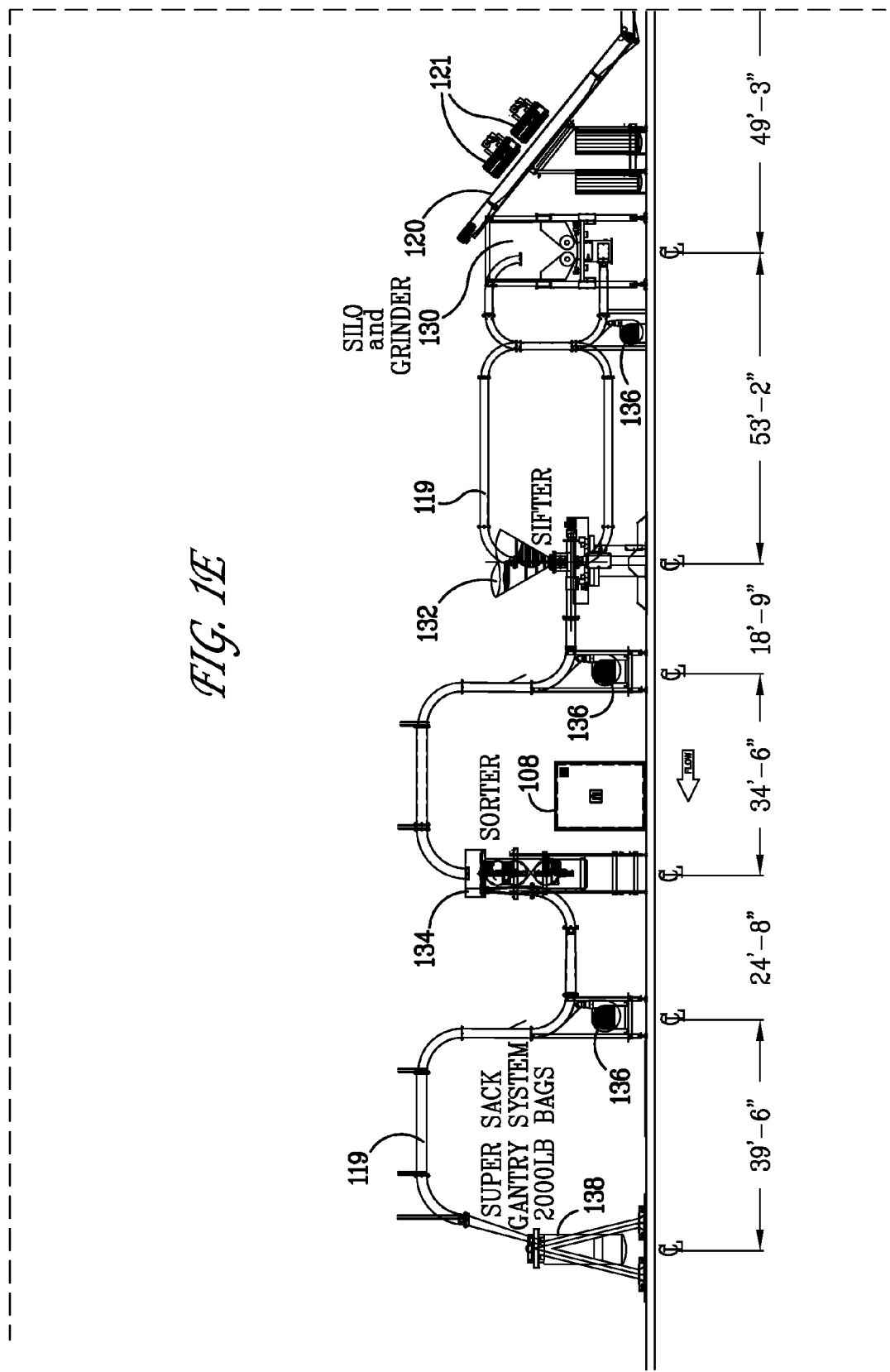
Figure 1F:
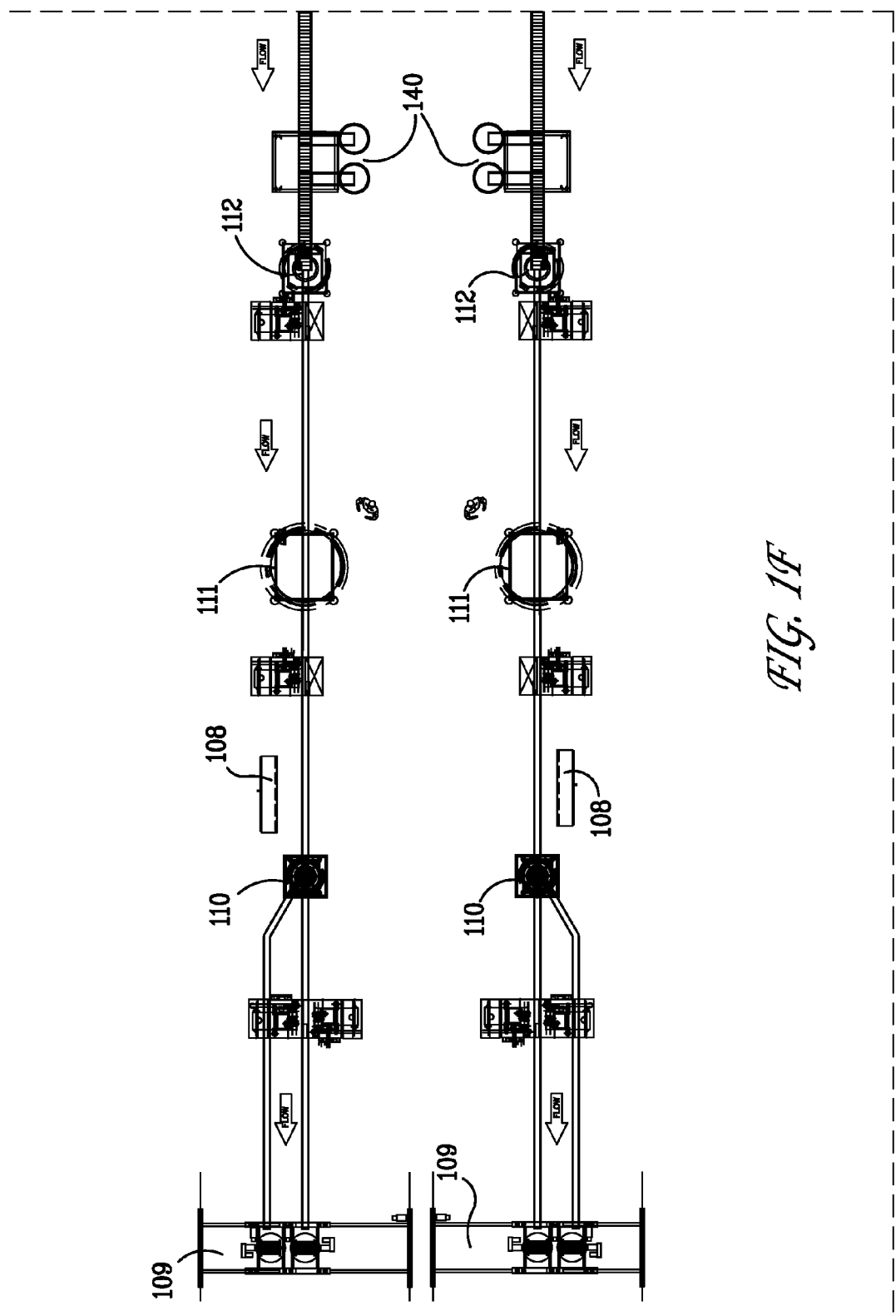
Figure 1G:
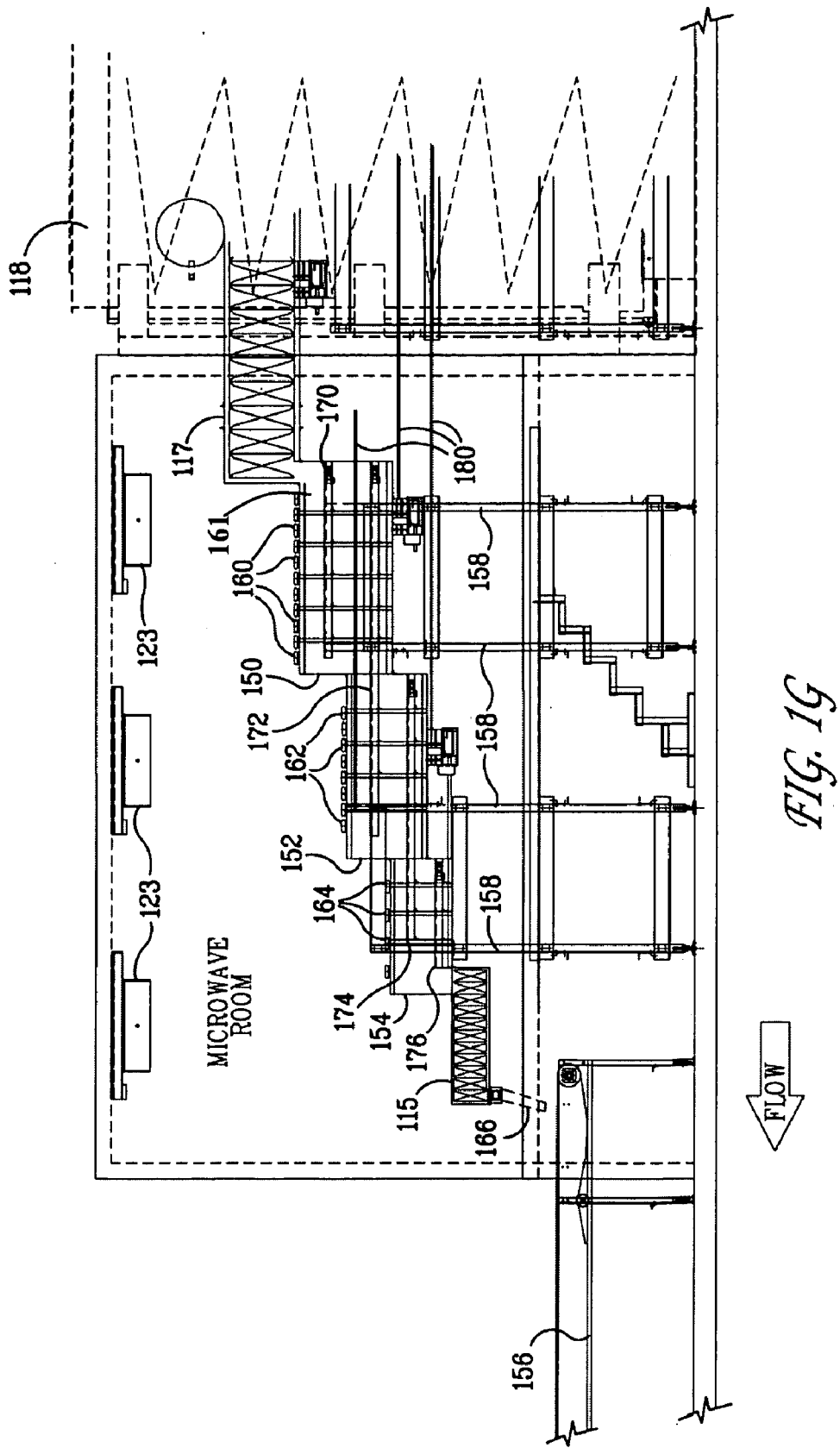

FIG. 1 comprises FIGS. 1A-1F, along with inset FIG. 1G. The orientation of FIGS. 1A through FIG. 1F are set forth in the inset in FIG. 1. Referring to FIGS. 1A-1G, there is provided an embodiment of the present invention directed to processing tire cuttings using microwaves to recover fuel oil. The processing equipment described herein is commercially available from one or more process equipment manufacturing companies.

FIG. 1A illustrates an elevation view of the beginning section of a tire cuttings plant layout according to an aspect of the present invention. This illustration shows two tire processing lines side-by-side in a parallel configuration. Tires from automobiles and trucks are first cut into suitable chips, e.g., 4×4 or 5×5 chips (not shown). The tire chips are transported using incline belt conveyor 120 to accumulation silos 102. The tire chips are then conveyed from the accumulation silos 102 to a pre-washer screw wash section 122. Tire chips are then conveyed to a pressure washer hot water sonic washer 105. Dirt, stones, gravel and other debris is cleaned off of the tire chips to minimize contamination of the process further downstream. The tire chips are then dried using forced air dryer system 106. FIG. 1B is a plan view of the beginning section of a tire cuttings plant layout corresponding to FIG. 1A. Cleaned and dried tire chips are then conveyed up another conveyor 120, as set forth in FIGS. 1C and 1D, below.

FIG. 1C is an elevation view of the midsection of the tire cuttings plant layout described here. Cleaned and dried chips are transported to accumulation silo 112, which are then transported along transport conveyor 120 to microwave room 124. The details of the microwave room 124 or further described in FIG. 1G below. In this elevation view, a dual wall tank with enclosed high high-capacity heat exchanger 118 is shown in dotted lines. This high-capacity heat exchanger receives hydrocarbon vapor produced by the microwave reactors residing within the microwave room 124. The position of the dual wall tank with enclosed high-capacity heat exchanger 118 is illustrated further in FIG. 1D.

FIG. 1D is a plan view of the midsection of the tire cuttings plant layout described here. Accumulation silos 112 feed tire chips via incline belt conveyor 120 and screw feed in-feed section 117 to a series of microwave reactors within hermetically sealed reactor room 116 with filtration system and vacuum pumps. Tire chips in the screw feed in-feed section 117 are fed into a first microwave reactor 150 (see FIG. 1G) residing within the microwave room 116. The microwave room is depicted in FIG. 1D containing two sets of microwave reactors side-by-side. Additional microwave reactors and additional lines can also be added. Hydrocarbon vapors generated in the microwave reactors from the irradiated tire chips are collected out of the top of each of the microwave reactors. The hydrocarbon vapors are then transported, under vacuum (e.g. at a pressure less than ambient) to heat exchanger 118. The heat exchanger is capable of further separating hydrocarbon vapors to oil and high carbon gases by cooling to a liquid or a vapor, depending on the vaporization temperature of the hydrocarbon vapors.

The microwave reactor room 116 is also depicted having refrigeration equipment 123 for maintaining constant room temperature. Processed tire chips exit the microwave reactor 154 (FIG. 1G) by a screw feed discharge section 115. Processed tire chips exit the final microwave room hot and are subsequently cooled using cooler 114. The cooled processed tire chips (below about 110° F.) then enter a pregrader grinder system 113, where processed carbon containing materials are separated from metallic materials (e.g., metal tire cords). Metal materials are separated using a suitable magnetic conveyor take away system, as shown in 121 in FIGS. 1E and 1F. Organic particles (e.g. carbon black) can further be shipped to bulk feed trucks equipped to handle fine particles, other packaging, as well as rail cars. The resulting organic particles are composed primarily of carbon. In some embodiments, the organic particles can be used as electronic activators, as described herein.

FIGS. 1E and 1F illustrate the magnetic conveyor take away system 121 for separating metal particles from nonmagnetic organic matter. Metal is stored in a metal storage unit 140 while nonmagnetic organic matter (e.g., carbon particles) is transported via incline belt conveyor 120 to silo and grinder 130. Carbon particles prepared according to the processes of the present invention are suitable for use as electron activators for the microwave processing of heavy residual refinery oil and other materials (e.g., residual oil from the bottom of a hydrocarbon distillation apparatus that is traditionally unable to be further processed). In one embodiment, the tire sidewalls can be separated from the tire treads. Tire treads typically have a greater amount of carbon black than the sidewalls. Accordingly, the amount of carbon black recovered from the treads is greater than that of the sidewalls. In one aspect, carbon black can be accumulated to form electron activator by processing the treads. Electron activator that can be further used in processing heavy viscous oil feedstocks. Also present is a sifter system with grinder return 111 for preparing controlled particle size carbon material. The matter in the silo and grinder 130 is transported by a pneumatic tube conveyor system 119 and auxiliary pump 136 toward sifter 132, and then to sorter 134, and finally to a super sack gantry system 138. The super sack entry system 109 is suitable for loading and unloading using forklift delivery. Also shown is electrical enclosure 108 containing control panels, a centrifugal feeder/sorter system 110 for managing fine particles.

As shown in FIGS. 1D and 1G, the microwave reactor room contains two series of three reactors each (one series is illustrated in FIG. 1G). Tire pieces enter first reactor 150 via screw feed infeed section 117. This reactor is the largest reactor of the series. 4×4 or 5×5 inch tire chips are first exposed to microwaves in the first reactor 150 by operation of the microwave antennas in the first microwave chamber 161. In this first stage, the tire pieces "pop" or explode into smaller pieces when exposed to the microwaves. The smaller pieces are separated through a mesh belt 170, and then transported onto another transportation mesh belt 172. The mesh is designed to keep the microwaves in the first reactor from getting through and over heating the tire chips. Typically, the temperature of the tire chips is maintained at about 465° F. or less. The mesh size in the larger reactor will have an opening of approximately 2 inches, the mesh size in the midsized reactor is approximately 0.5 inches, and the mesh size opening for the smallest reactor is approximately 1/16".

Microwaves are generally generated outside of the microwave room and transported into the microwave room by a suitable microwave conduit, e.g. stainless steel wire. The design and interconnection of the three microwave reactors in series is provided so that the location of the tire chips in the microwave radiation zone is maintained so that the tire chips do not exceed 465° F. Initially, "popping" of the tire begins in the first reactor 150 when the temperature of the tire chips is in the range of from about 300° F. to about 450° F. It has been surprisingly found that once the temperature exceeds about 450° F., the carbon black residing within the tires can be charred and overcooked and the efficiency of the process for recovering hydrocarbon fuel oils diminishes drastically. Accordingly temperature is desirably maintained below about 465° F., or even below about 550° F. Without being bound by any particular theory of operation, it appears that the tire chips pop because the reactors are under vacuum and a lot of gas within the tire chips is being released suddenly upon irradiation with microwaves.

Suitable operating pressures are the range of up to about 20 mm of mercury, or even up to about 40 mm of mercury, or even up to about 100 mm of mercury. Accordingly, tire chips processed in the first microwave reactor 150 are then transported to the second microwave reactor 152, where the processed chips are further irradiated under vacuum using microwave antennas 162. The tire chips are further reduced in size, and fall through mesh 174, and then transported to the third microwave reactor 154. In the third microwave reactor 154, the processed chips are further irradiated using microwave antenna 164. Processed chips are finally transported by a screw feed discharge section 118 and exit the microwave reactors from screw feed discharge section 166, and through airlock (not shown) and onto conveyor 156.

Each of the microwave reactors are fed with microwave conduits terminating in a suitable cone or nozzle. The first microwave reactor has more microwave nozzles 160 as it is larger than the other two microwave reactors. The second microwave reactor is shown with microwave nozzles 162, and the third microwave reactor is shown with microwave nozzles 164. Each of the microwave reactors contains vacuum lines 180 to transport the resulting hydrocarbon gases to the high-capacity heat exchanger 118 (shown in dotted lines). Also shown in the microwave room 124 are refrigeration equipment 123 to maintain the temperature of the ambient conditions in the microwave room, and support structures 158 for supporting the microwave reactors.

Suitable microwave ranges for the processing of tire chips includes using X-band microwave radiation generators (not shown) transmitted via conduit in tubes at various frequencies to each of the reactors. Microwave frequencies for tire processing varies from X-band down towards C-Band radiation. X-band is 5.2 to 10.9 GHz; C-band is 3.9 to 6.2 GHz. K-band radiation is also useful in some embodiments. K-band is 10.9 GHz to 35 GHz, which includes the sub-bands Ku (15.35 GHz to 17.25 GHz) and Ka (33.0 GHz to 36.0 GHz). Typically separate microwave antenna tubes are separated in frequency by approximately 0.2 gigahertz. In the embodiment shown in FIG. 1G, a total of approximately 36 microwave antenna tubes are transported from a microwave source (not shown) to the microwave reactors. The largest microwave reactor 150 has the greatest number of tubes, for example about 18. The second microwave reactor 152 has fewer tubes, approximately 12. The third microwave reactor 154 has the fewest number of tubes, approximately 60. Each of the tubes are capable of operating at different frequencies, which frequencies in certain preferred embodiments varies between about 7.0 and 6.4 GHz. The ends of the microwave antenna from which the microwave radiation exits into the reactor chambers are fitted with a suitable cone antenna. Each of the cone antennae emits microwave radiation at a separate frequency, which is typically about 0.2 GHz different than the others that irradiate into each of the microwave reactors. Microwaves are typically fixed in frequency but they may also be capable of being swept in a varying frequency manner, for example, by using a variable frequency microwave generator. A number of different frequency combinations are envisioned, for example each of the cone antennas may be fixed in frequency, vary in frequency, or any combination thereof. As the tire chips are irradiated, volatile hydrocarbon vapors are emitted from the tire chips and collected by vacuum tubing. Hydrocarbon vapors are then transported to a heat exchanger condenser. Highly volatile gases and vapors that are not conveniently liquefied can be separately recovered as a high BTU gas product.

The plant layout described in FIGS. 1A-1G is operated at a product speed (per line) of approximately 30 tires per minute on average. Hourly production rate is approximately 36000 pounds per hour or approximately 1300 ft.$^3$ per hour. This is based upon a used automobile tire weight of approximately 20 pounds (9.1 kg). Or alternatively a used truck tire about 40 pounds (18.2 kg). The shredded tire chip sizes can be in the range of from about 3 to about 5 inches. Average loose density of the chips is approximately 24 pounds per cubic foot to about 33 pounds per cubic foot. Heat values generated at atmospheric pressure range from approximately 12,000 BTUs per pound to about 15,000 BTUs per pound.

Figure 2A:
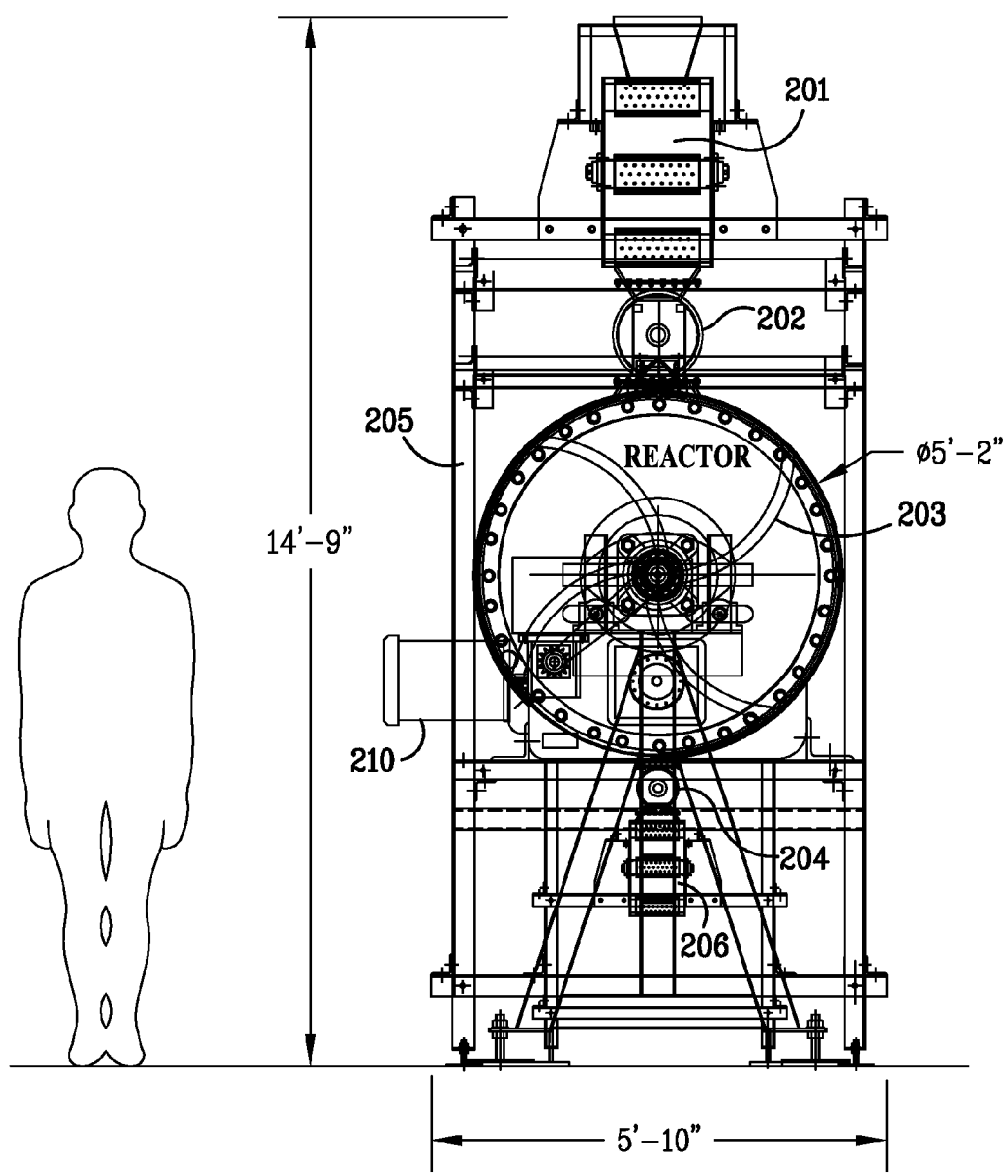
FIG. 2A is an elevation view, axial direction, of a microwave reactor suitable for processing oil cuttings according to an aspect of the present invention.

FIG. 2A is an elevation view, axial direction, of a microwave reactor suitable for processing oil cuttings according to an aspect of the present invention. Oil cuttings comprise dirt, rock, water, carbon deposits, and the like, which oil cuttings are obtained during drilling operations. Drilling operations include drilling from an oil rig, drilling from a deep-sea oil platform, as well as mining of shale rock and coal deposits. During drilling, rock that is rich in hydrocarbons is typically reached prior to hitting a pocket of oil. This hydrocarbon rich rock is transported up to the surface and can comprise up to 15% oil, and even up to 25% oil. The consistency can also be similar to oil shale. Hydrocarbon rich rock can be considered hazardous waste and would need to be disposed of properly. It cannot be sent to a landfill, and accordingly it has traditionally been handled by combustion. This is particularly a problem on an oil rig in the middle of the ocean, where it may be forbidden to dump oil drillings comprising greater than 1% hydrocarbon content. Accordingly, the process of the present invention can also be used to recover hydrocarbons from drill cuttings, thereby permitting the drill cuttings to be placed back in the environment after the hydrocarbons have been substantially removed. As used herein the term "substantially removed" refers to a composition comprising less than 1% by weight hydrocarbon content. Oil drill cuttings having less than 0.01% by weight hydrocarbon has been produced using the processes described herein. Accordingly, the methods suitably provide drill cuttings that comprise less than 1 percent, or even less than 0.5 percent, or even less than 0.2 percent, or even less than 0.1 percent, or even less than 0.05 percent, or even less than 0.02 percent, or even less than 0.01 percent by weight hydrocarbons based on weight oil cuttings. Suitable oil cuttings enter into the system through in-feed grinder system 201. Oil cuttings are ground to a suitable size, then fed into the microwave reactor chamber (vacuum sealed reactor tank 216) via in feed screw 202. The vacuum sealed reactor tank 216 contains a helical mixer element 203 for mixing and stirring the ground oil cuttings. The reactor tank is typically filled to about 40% of its total volume. The microwaves irradiate the contents of the reactor via antennas that are oriented in an orbital arrangement emanating from the top of the reactor. The microwave antennas are desirably flexible and irradiate from several slides from the top the reactor towards the mixing material below. A helical mixer element is turned using a motor 210. Microwaves emanating from a cone antenna or a plurality of cone antennas (not shown) irradiate the oil cuttings with suitable microwave radiation. Hydrocarbon gases and oil vapor exit towards the top vacuum tubing towards vacuum pump and collected in a suitable heat exchanger vapor condensing unit. Hydrocarbon vapor gases produced by the process of irradiating the oil cuttings with microwaves exit via a vacuum discharge tube (not shown). Residual geologic material and unreacted carbon deposits settled towards the bottom of the reactor. The unvaporized matter is discharged from the microwave reactor 216 via screw feed discharge section 204, and exits the system via discharge system 206. Material exiting the system is suitably clean of hydrocarbons so as to be considered nonhazardous waste. For example, material exiting the reactor can be returned to the ocean after drilling, or can be returned to the land after drilling. Also shown is reactor support structure 205 for holding the components as set forth in the system.

Figure 2B:
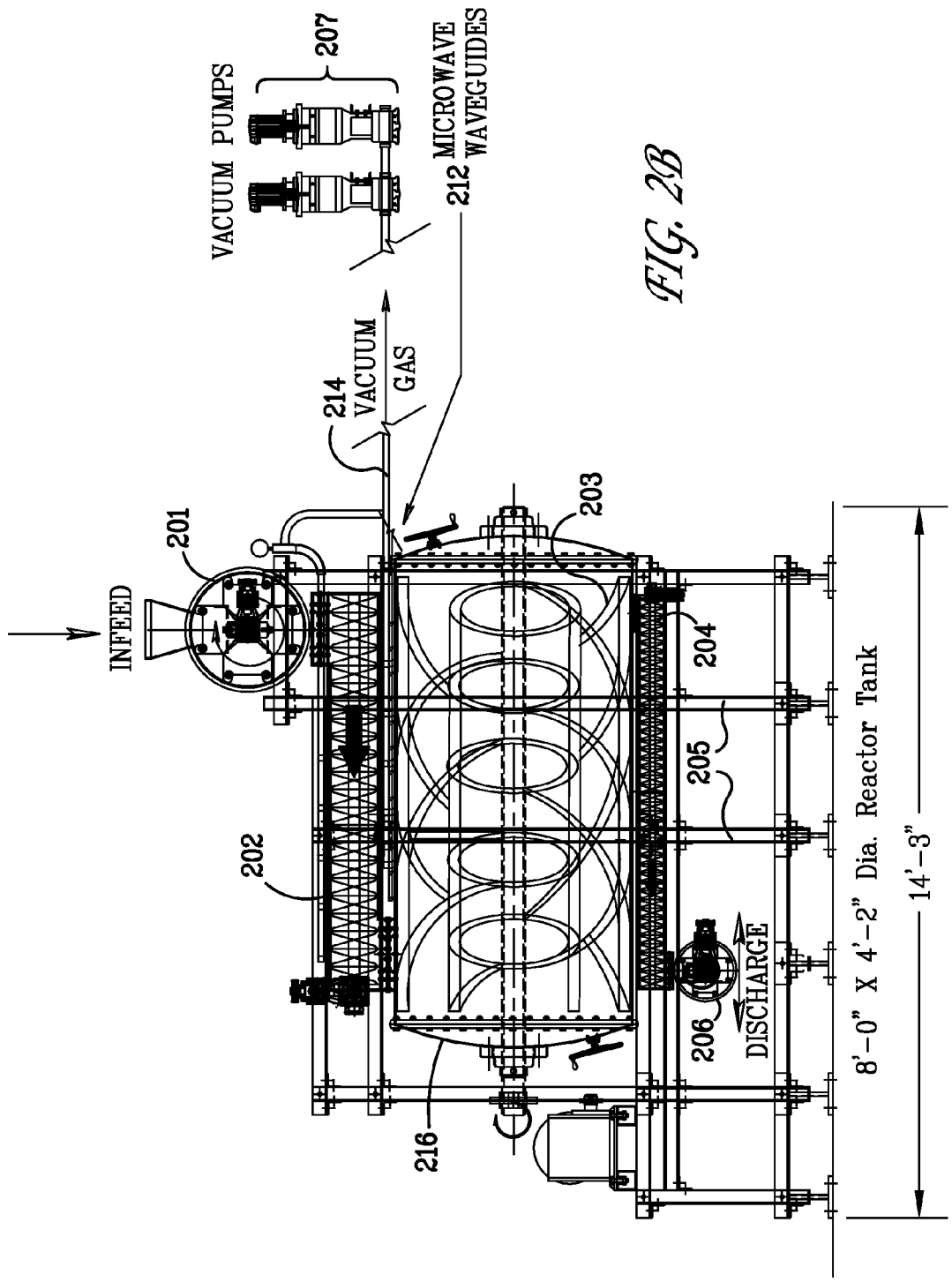
FIG. 2B illustrates an elevation view of the microwave reactor of FIG. 2A, longitudinal direction.

FIG. 2B illustrates an elevation view of the microwave reactor of FIG. 2A, longitudinal direction. Oil cuttings are added to the system as in-feed via an airlock at 201, which oil cuttings are then transported to the reactor 216 via in-feed screw 202. Depicted in this diagram is conduit 214 for pulling vacuum on the airlock, and on the vacuum sealed reactor tank 216, using vacuum pumps 207. Microwave waveguides 212 are shown entering the vacuum sealed reactor tank 216. Microwaves emanating from a suitable microwave cone antenna radiates the oil cuttings within the reactor tank. A helical mixer element 203 rotates to mix the oil cuttings, convey the oil cuttings, and reflects microwaves throughout the volume of the chamber. After suitable microwave processing at a particular residence time, the reacted oil cuttings exits the reactor through screw feed discharge section 204 and exits via a suitable airlock 206 of the discharge system. Also shown is reactor support structure 205.

Figure 2C:
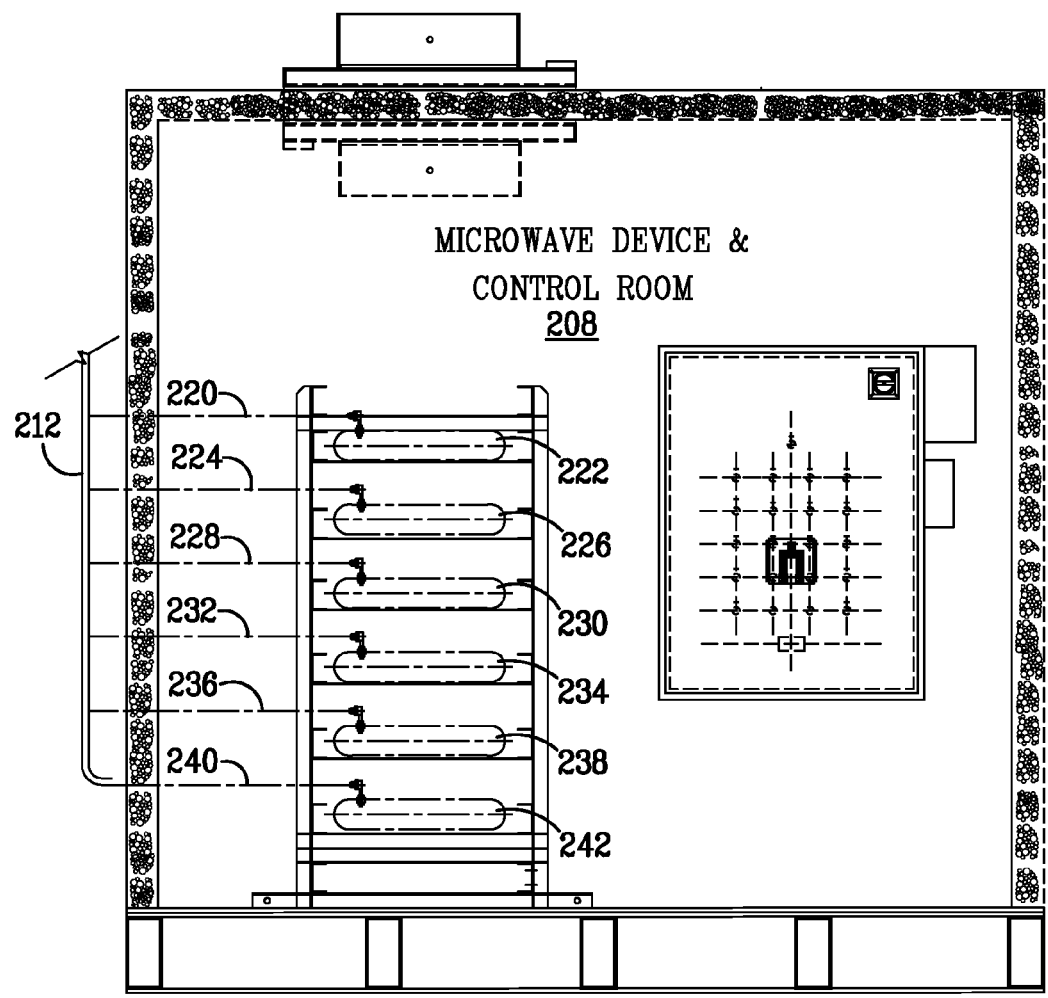
FIG. 2C illustrates an elevation view of the microwave device and control room suitable for generating microwaves and propagating the same through waveguides.

FIG. 2C illustrates an elevation view of the microwave device and control room suitable for generating microwaves and propagating the same through waveguides. The microwave device and control room 208 is depicted as comprising an electrical panel and a series of six individual microwave generators (222, 226, 230, 234, 238, and 242) each connected to a series of microwave antennas (220, 224, 228, 232, 236, and 240). The antennas are combined into a combined antenna conduit 212 which exits the microwave device control room 208 and leads towards the vacuum sealed reactor tank 216 as shown in FIG. 2B. Suitable microwaves for processing oil drill cuttings have frequencies in the range of about 11.2 to about 11.8 GHz, typically about 11.5 GHz. Oil shale can also be processed using the equipment and processes described herein at a microwave frequency in the range of from about 10.6 to about 11.2 GHz, and typically about 10.9 GHz. Tar sands can be appropriately processed using microwaves 4 to about 12 GHz. Tar sands can also be processed in the K-band, preferably in the Ku band. Anthracite coal deposits can also be processed in the KU band as well. A vacuum is maintained within the microwave reactor chamber using suitable vacuum and hydrocarbon vapor condensation equipment, for example at pressures less than about 100 mm of mercury, and even at pressures of less than about 40 mm of mercury, or even at pressures of less than about 20 mm of mercury. Maintaining such low operating pressures helps to keep the overall process temperatures below about 465° F. or even a temperatures less than about 450° F. so as to prevent overheating and efficient recovery of hydrocarbon vapors. A large proportion of the hydrocarbon vapors can be condensed into liquid fuel oil at ambient temperatures.

The system described in FIGS. 2A-2C can be suitably adapted and scaled to process oil cuttings at a throughput of up to about 2 tons per hour to even up to about 10 tons per hour. It should be readily apparent to the skilled person how to increase the size and power of the microwave reactor chamber to yield higher throughputs.

The system described in FIGS. 2A-2C can also be suitably adapted in scale to process oil shale rock. The processing of oil shale rock includes irradiating it with suitable microwaves at power sufficient to increase the temperature of the oil shale rock to within a range of from about 500° C. to about 600° C. Without being bound by any theory of operation, it is believed that these processing temperatures are considerably hotter than compared to tire cuttings for the reason that more energy needs to be applied to the rocks to volatile lies the hydrocarbons. This is in contrast to softer, substantially higher concentration hydrocarbon, tires that readily absorb the microwave energy. Suitable shale rocks are broken down into small pieces after being mined. For example, shale rock pieces are suitably smaller than an inch cube, even smaller than a half inch cube, or even smaller than about ⅜" cube, even smaller than about a half inch cube, or even smaller than about ¼" cube. The hydrocarbon content of the oil shale rock typically comprises hydrocarbons comprising from about C10 to about C25, or even from about C14 to about C22. Oil shale rock can contain up to about 5% by weight hydrocarbons, or even up to about 15% by weight hydrocarbons, or even up to about 25% by weight hydrocarbons. In some cases, shale rock can contain up to about 70% by weight hydrocarbons.

Figure 3A:
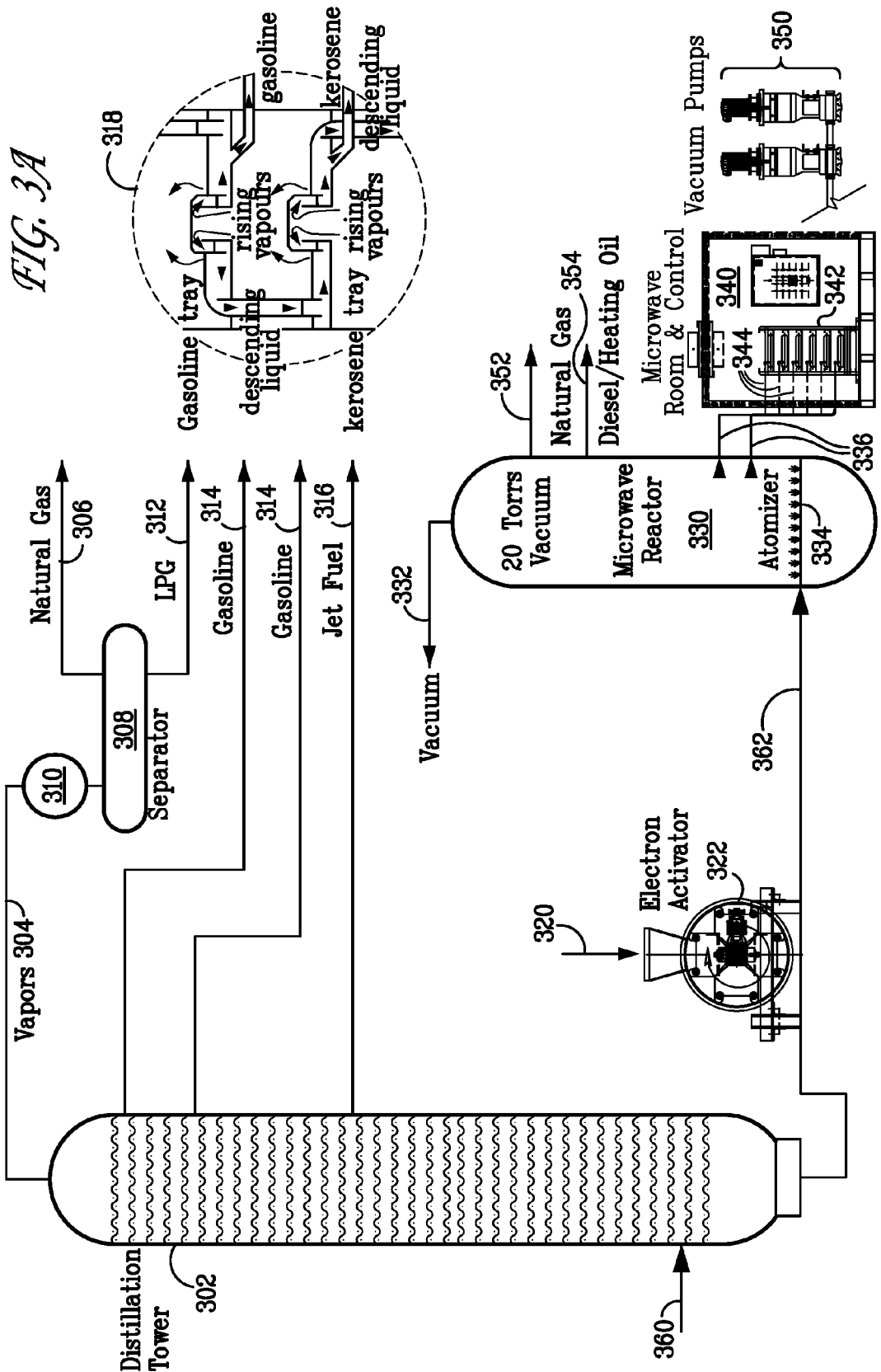
FIGS. 3A-3B illustrate several embodiments of the present invention for extracting petroleum-based materials from oil slurry.
Figure 3B:
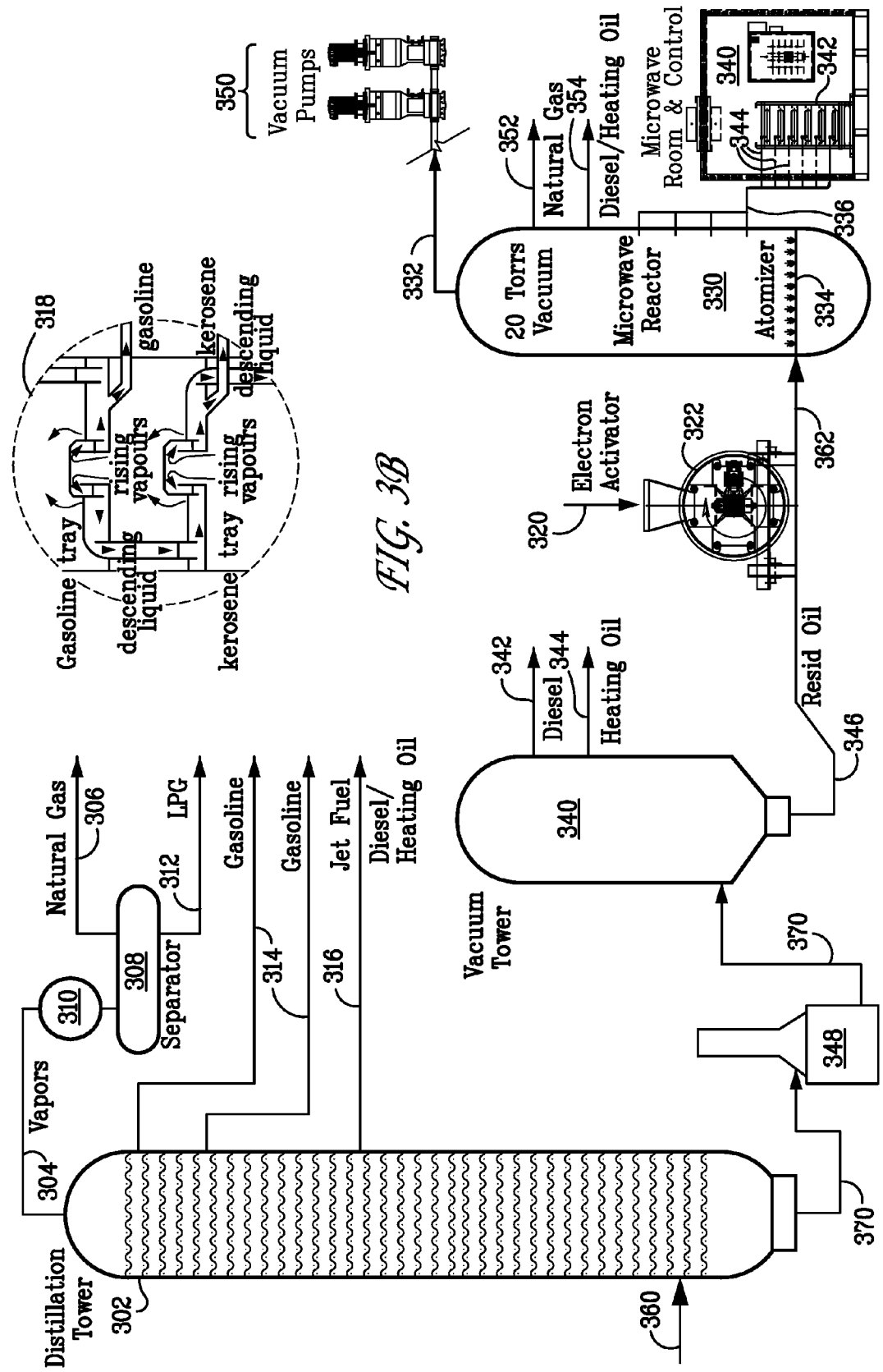

FIGS. 3A and 3B depicts several embodiments of the present invention for recovering petroleum-based materials and hydrocarbons from oil slurry. FIGS. 3A and 3B are schematic illustrations of two embodiments of a microwave assisted system for the distillation and recovery of heavy oil bottoms, e.g., oil slurry, from a distillation plant. FIG. 3A shows the following elements of a traditional hydrocarbon distillation plant: 302 distillation tower 360 unrefined inlet into distillation tower; 304 vapor line; 306 natural gas line; 308 gas separator; 310 pump; 312 LPG line; 314 gasoline lines; 316 jet fuel (kerosene) line; and 318 inset: close-up view of the liquid vapor contact caps with an a distillation tower. This distillation system can be modified using the microwave process of the present invention as follows. An electron activator 320 is added using an electron activator pump 322 into residual oil 362. Hot residual oil line (e.g., heavy oil) 362 is pumped into the microwave reactor 330 and atomized using an atomizer 334. Microwave waveguide antenna 336 is powered from the microwave room and control system 340, which control system includes microwave generators 342 and microwave waveguides 344. The microwaves exit the waveguide antenna 336 at cone nozzles within the microwave reactor so as to radiate the atomized residual oil above the atomizer 334. Vacuum pumps 350 connected to the vacuum line 332 maintains pressure of less than about 20 mmHg, or even less than about 40 mmHg, or even less than about 100 mmHg. The irradiation of the atomized residual oil gives rise to cracking of the residual heavy oil, which in turn produces hydrocarbon vapors such as natural gas 352 and heavier hydrocarbon vapors such as diesel and heating oil 354. In the microwave reactor 330, residual oil 362 is removed from the bottom of a distillation tower 302, combined with electron activator 320 and processed by microwave after atomization. We have discovered that addition of the electron activator to the residual oil, for example about 2% by weight based on residual oil of carbon small particles, gives rise to a much faster, more efficient absorption of the microwaves to yield more efficient cracking of the residual oil. Accordingly, electron activator made using microwave processing of tire chips as described supra is useful for making electron activator. Suitable electron activator is provided as a fine powder, for example of about a hundred mesh, or finer. The electron activator may be coarser than 100 mesh, depending on the precise application and handling requirements. Without being limited by any particular theory of operation, the electron activator enhances the absorption of microwaves by the residual oil, which gives rise to faster processing and more efficient processing of the heavy oil. As a result, the electron activator, which comprises carbon powder particulates, are capable of absorbing microwave radiation. Solid particles containing residual hydrocarbons, such as electron activator, result in popping (as in popcorn) when irradiated. Without being bound by any particular theory of operation, it is believed that the popping action of the small electron activator particles within the residual oil enhances the microwave processing of the residual oil. In certain embodiments, the electron activator functions as a catalyst for effectuating the microwave cracking process.

Suitable microwave radiation frequency ranges from about 8.0 to about 8.8 GHz, or in the range of from about 8.1 GHz to about 8.7 GHz, or even in the range of from about 8.2 GHz to about 8.6 GHz, or even in the range of from about 8.3 GHz to about 8.5 GHz, or even about 8.4 GHz. The microwave reactor contains a series of microwave cone antennas that radiate the atomized residual oil with microwaves. These microwave cone antennas can each receive the same or different microwave frequencies. When the frequencies differ, they typically are separated by increments of about 0.2 GHz. Ranges of microwave frequencies are typically useful for processing the atomized residual oil in this manner. Accordingly multiple microwave antennas 344 receive microwaves generated by a plurality of microwave generators 342 provided in the microwave control system 340. Microwaves are transmitted through microwave antennas 344 to the microwave antenna conduit 336. Microwaves then enters the microwave reactor. Typically the residual oil 362 is pre-heated to a temperature of about 350° C. so that it is capable of flowing under pressure and atomized. The use of microwaves has been demonstrated to effectively crack the hydrocarbon chains in the heavy residual oil. Atomization helps to increase the surface area of the residual oil and decrease particle size, thereby effectuating absorption of the microwaves and cracking of the hydrocarbon chains. The residual oil is suitably heated to temperatures sufficient that can flow under pressure and atomized. Suitable temperatures are at least about 250° C., or even at least about 300° C., or even at least about 350° C., or even at least about 400° C., or even at least about 450° C., or even at least about 500° C. The residual oil may be preheated using any of a variety of heating methods, for example convection, conduction, or irradiation, e.g. microwaves. The heavy residual oil chains crack at least several times.

Processes according to the present invention are capable of producing combustible gases. The processes according to the present invention are also capable of producing at least several different weights of oils. These oil products range from carbon content of hydrocarbon chains comprising from 14 carbons up to about 25 carbons. The starting residual oils comprise hydrocarbon chains having at least 25 carbons or even at least 28 carbons. The hydrocarbons in the residual oil do not necessarily need to be linear hydrocarbon chains, for example cyclic and branched hydrocarbons are also envisioned. Instead of atomization, hot flowing residual oil can be formed into a thin film and irradiated with microwaves, or can be ejected into a shooting stream and irradiated with microwaves, or can be broken into droplets under force of pressure and irradiated with microwaves. Similar related processes give rise to narrow dimension residual oil droplets. In certain embodiments the products of microwave radiation within the microwave reactor 330 illustrated in FIG. 3A can be recycled back to the distillation tower 302 for further processing.

FIG. 3B is a schematic of another embodiment of a microwave assisted distillation and recovery unit for heavy oil bottoms from a distillation plant. This embodiment is similar to that described in FIG. 3B, with the exception that this embodiment further includes a reboiler 348 for heating the bottoms coming from distillation tower 302 by a transfer line 370. The reboiler heats the bottoms which are distilled in vacuum tower 340. Residual oil 346 from the vacuum tower is combined with electron activator 320 using electron activator pump 322 to provide a mixture of residual oil in electron activator 362. This mixture is then atomized in microwave reactor in 330. The operation of the microwave reactor is similar to that discussed supra in FIG. 3A.

Figure 4A:
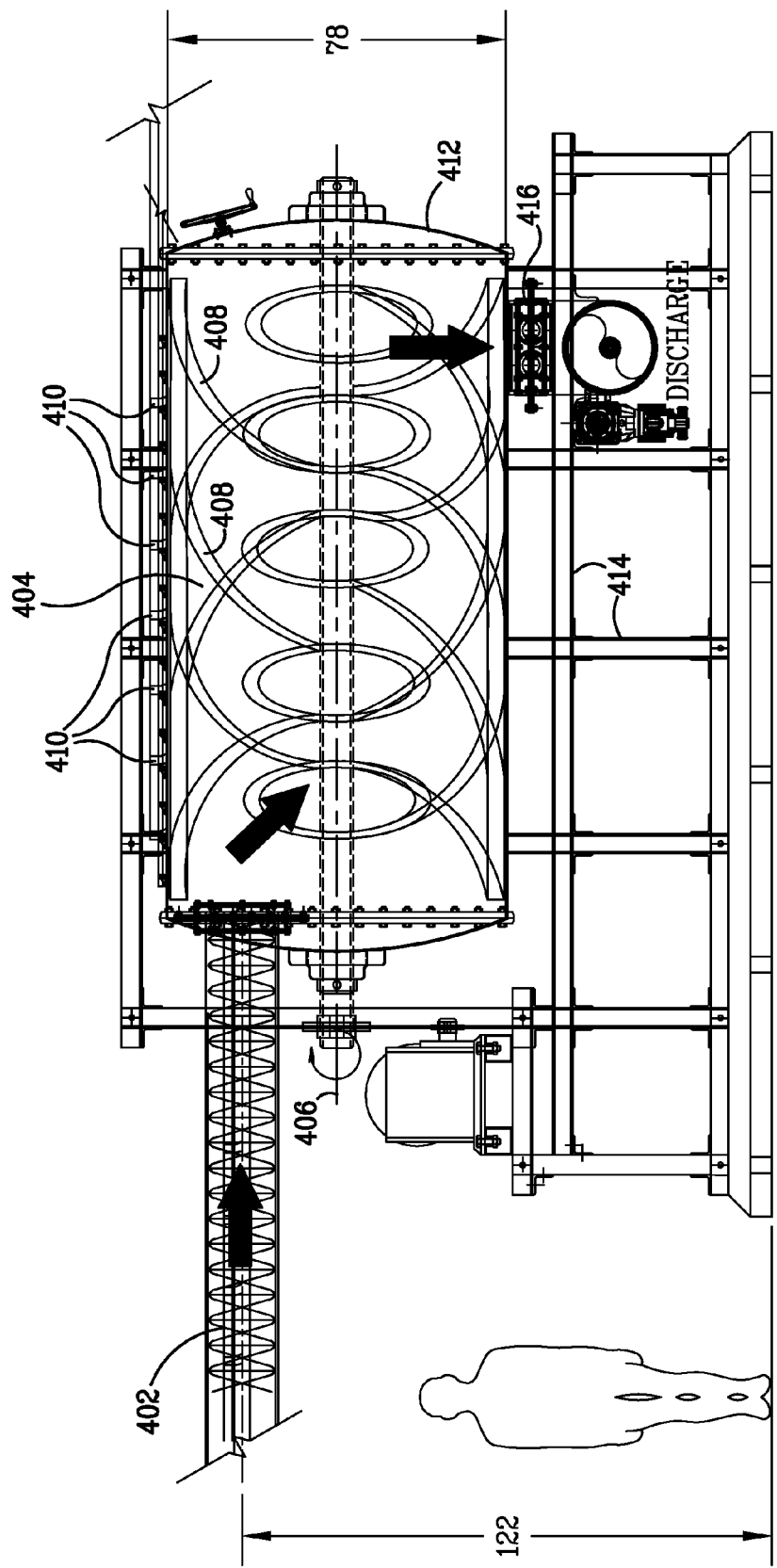

FIG. 4A illustrates an elevation view of a microwave reactor system suitable for processing shale rock, tar sands, drill cuttings, and the like. Inlet feed screw 402 is suitable for transporting shale rock and other hydrocarbon containing cuttings and the like into microwave reaction chamber 412. Helical screw mixing flights 408 are mounted to an axle 406 which is rotated using a motor. Helical screw mixing flights mix and transport the material, such as shale rock pieces, in the microwave reaction chamber interior 404. Microwave antennas 410 enter the interior of the microwave reaction chamber 404. The material within the microwave reaction chamber interior is stirred and irradiated. Vapors are removed using a vacuum recovery system and condensing unit (not shown). Material depleted of hydrocarbon vapor is discharged through the exit discharged from feed system 416. Also shown is a support structure 414.

Figure 4B:
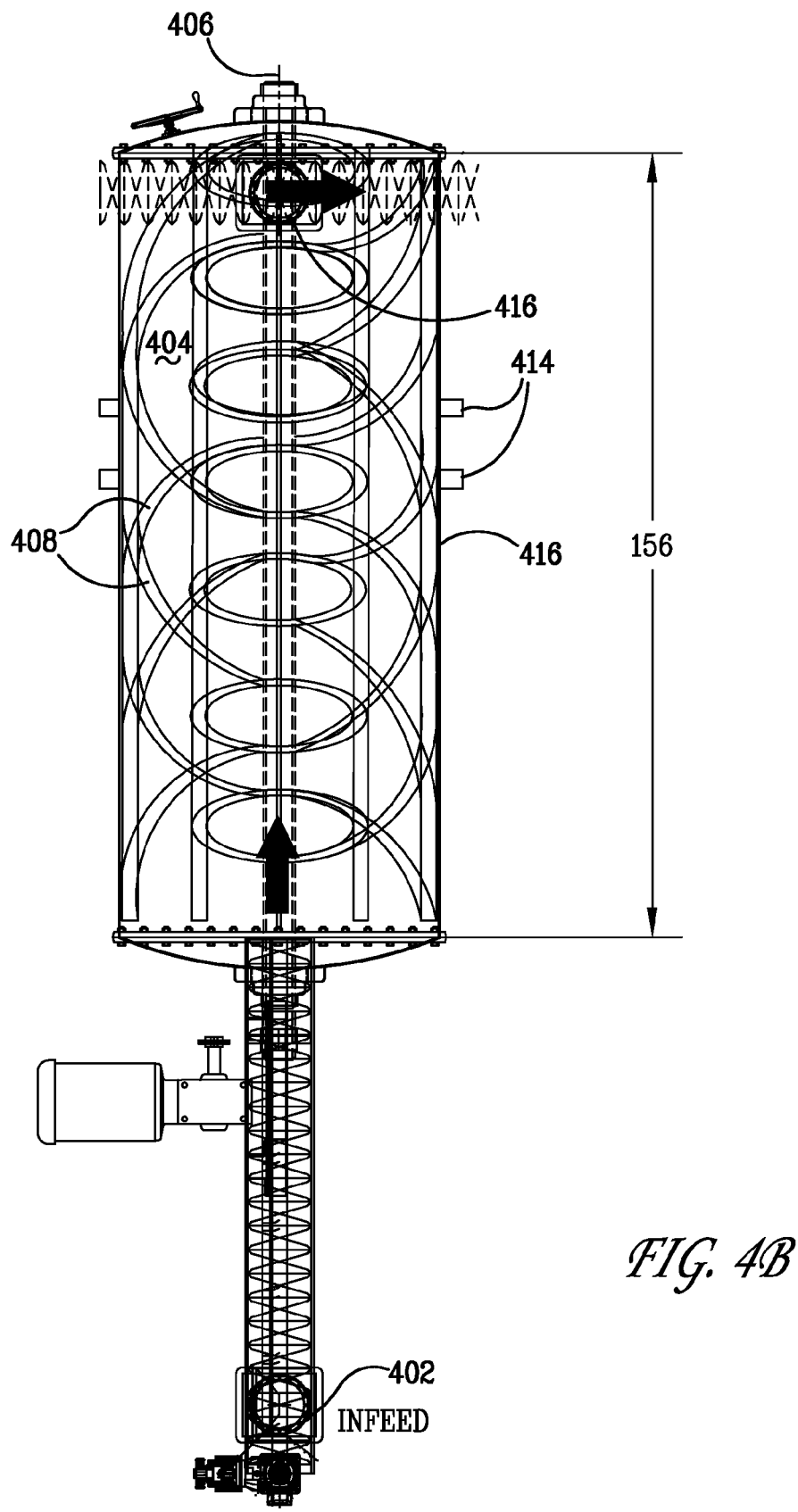
FIG. 4B provides a plan view of FIG. 4A.
Figure 4C:
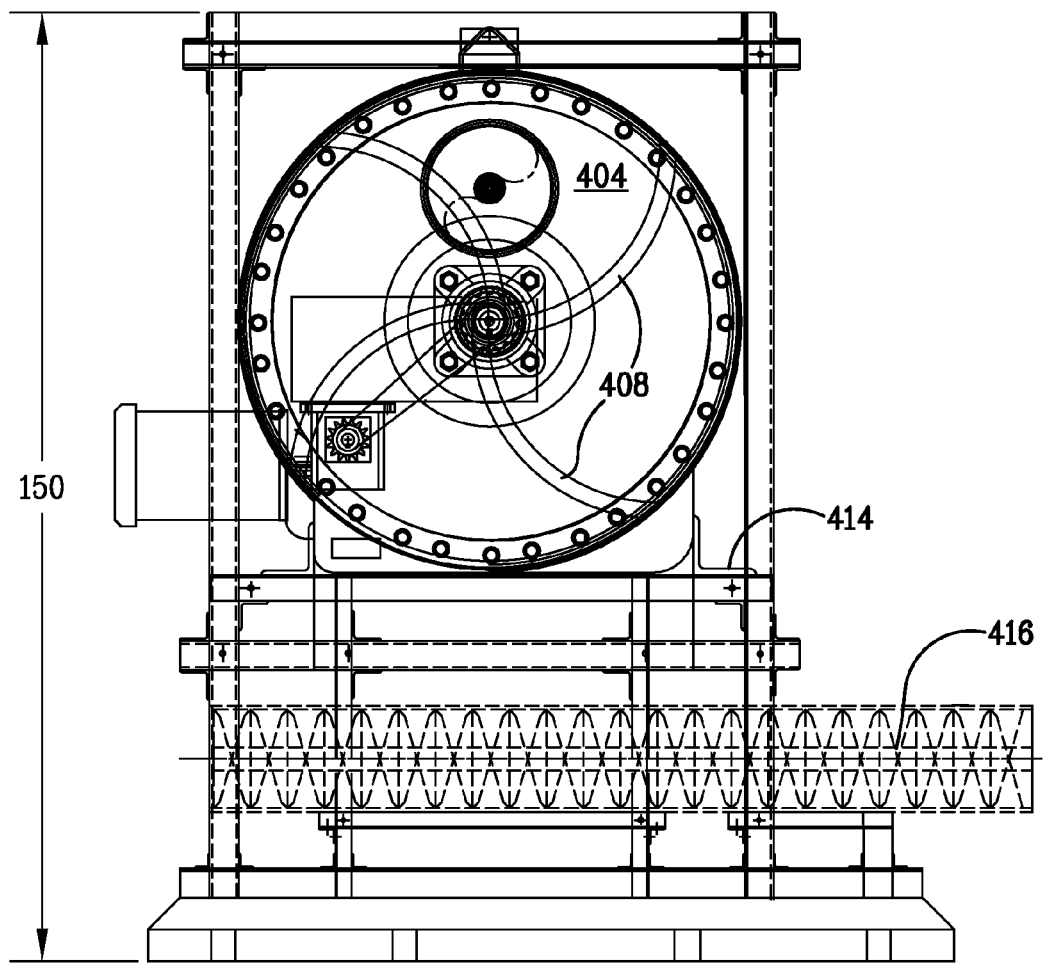
FIG. 4C is an elevation view of the microwave reactor system along the axis 406, the near end being the exit discharge screw feed system section 416.
Figure 4D:
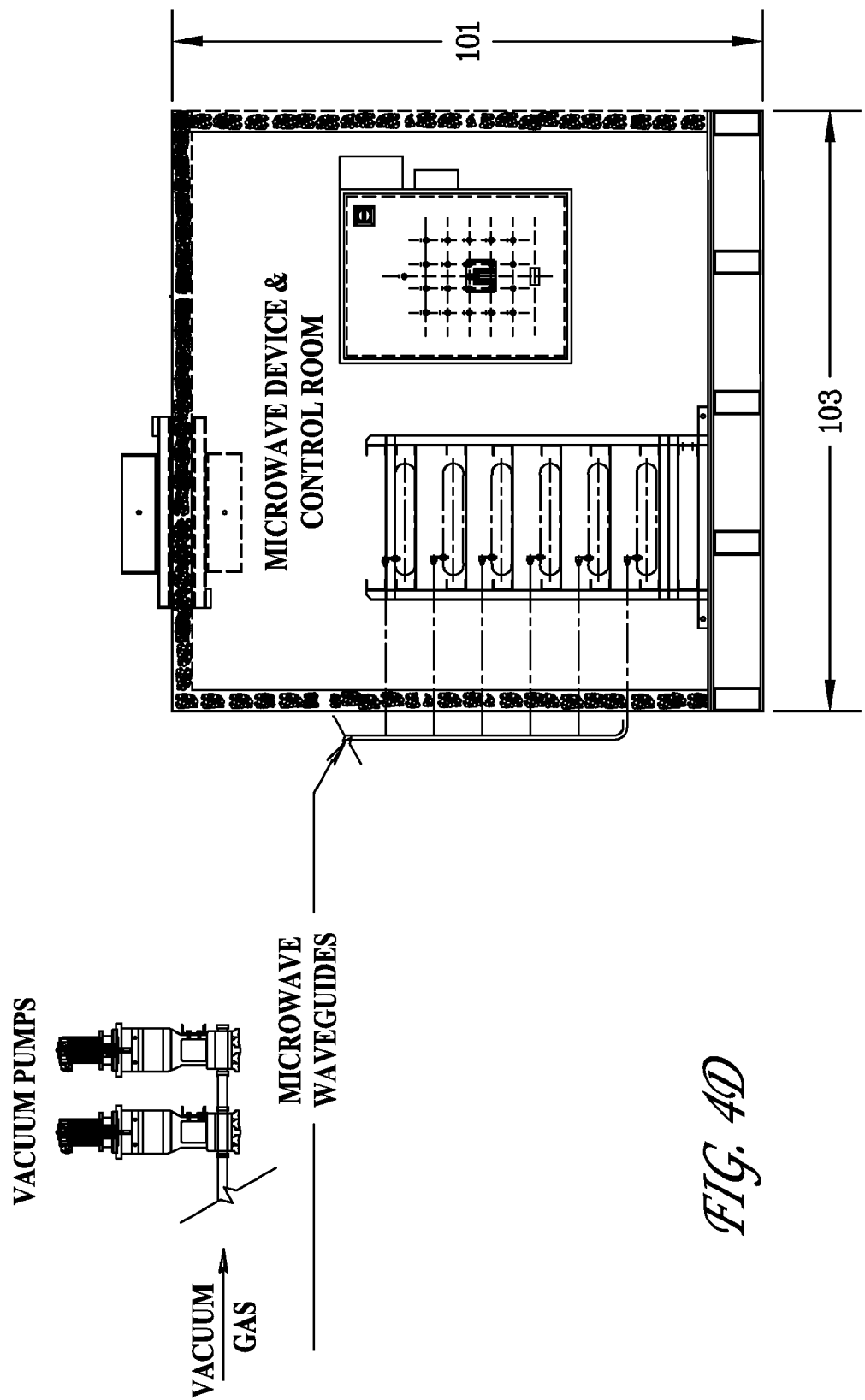
FIG. 4D illustrates a suitable microwave device control room, waveguides, and vacuum pumps suitable for use with the system illustrated in FIG. 4A.
Figure 4E:
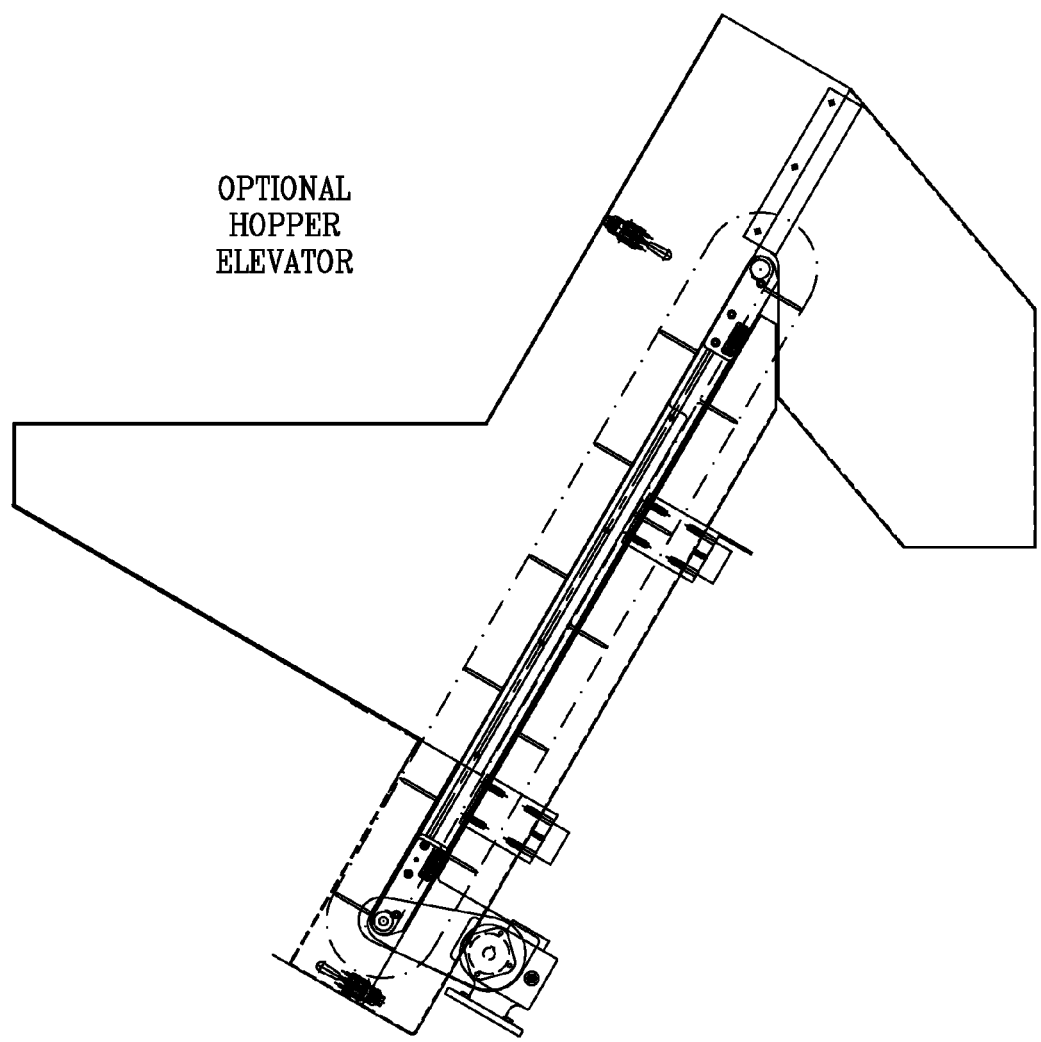
FIG. 4E illustrates an optional hopper elevator for transporting material into the inlet feed section 402.
Figure 4F:
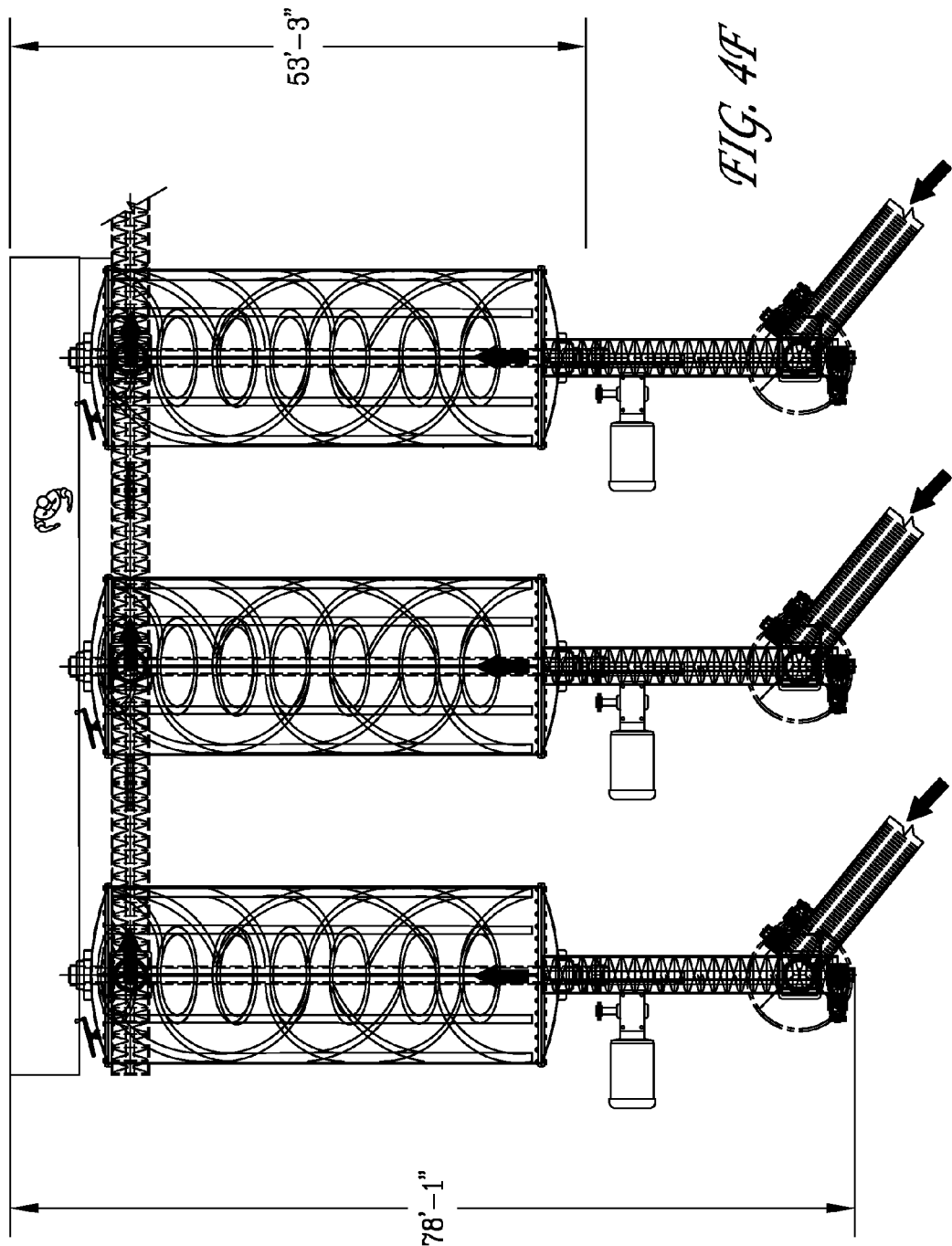
FIGS. 4F and 4G illustrate three horizontal microwave reactor systems operating in parallel.
Figure 4G:
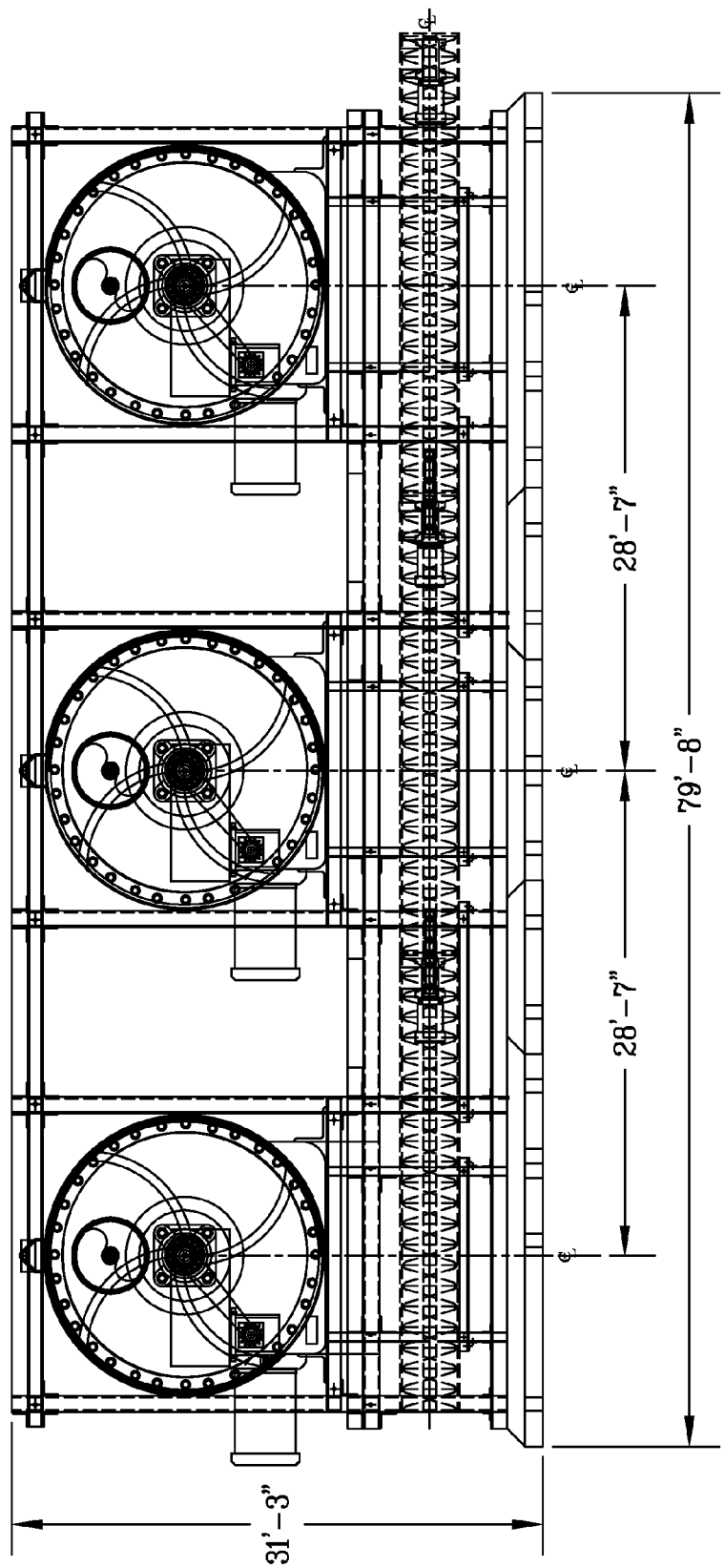
Figure 4H:
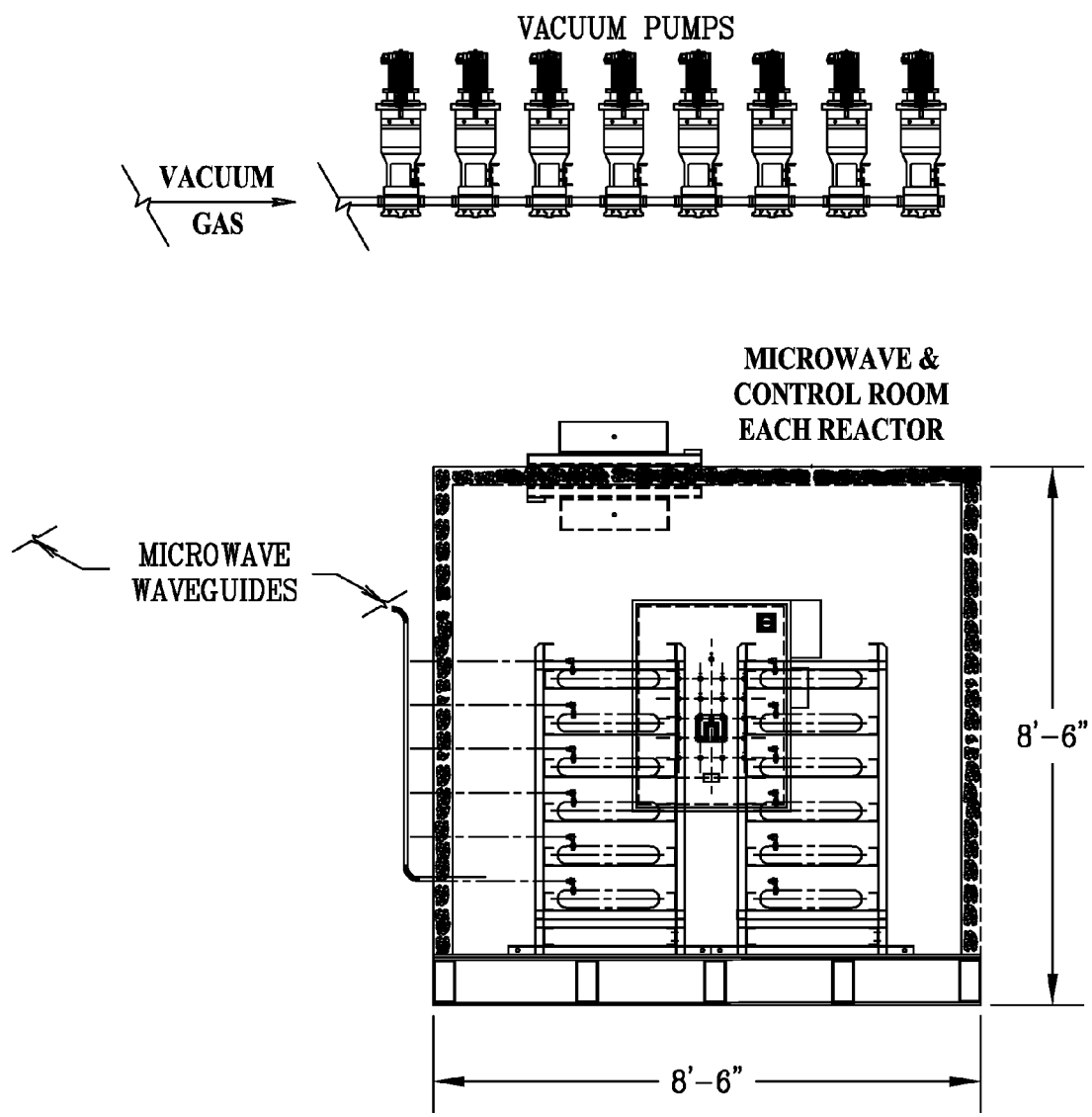
FIG. 4H illustrates additional microwave generators, waveguides and vacuum pumps for operating the three horizontal microwave reactors illustrated in FIGS. 4F and 4G.

FIG. 4B provides a plan view of FIG. 4A, wherein the direction of the material is shown entering the microwave reaction chamber via onlet feed screw 402 mixing within the microwave reaction chamber by a helical screw mixing flights 408, and finally exiting via exit discharge screw feed system 416. FIG. 4C is an elevation view of the microwave reactor system along the axis 406, the near end being the exit discharge screw feed system section 416. FIG. 4D illustrates a suitable microwave device control room, waveguides, and vacuum pumps suitable for use with the system illustrated in FIG. 4A. FIG. 4E illustrates an optional hopper elevator for transporting material into the inlet feed section 402. FIGS. 4F and 4G illustrate three horizontal microwave reactor systems operating in parallel. FIG. 4H illustrates additional microwave generators, waveguides and vacuum pumps for operating the three horizontal microwave reactors illustrated in FIGS. 4F and 4G. The processing of hydrocarbon containing materials, such as shale rock, tar sands, drill cuttings and the like, is conducted in a vacuum environment, less than about 20 mm of mercury, or less than about 40 mm of mercury, or even about less than 100 mm of mercury. The hydrocarbon containing materials are subject to heating by the microwaves and other heating means, up to about 350° C., or even up to about 450° C., or even up to about 550° C., or even up to about 600° C. The hydrocarbon containing materials are removed from the microwave reactor chamber via a suitable vacuum plumbing system. The hydrocarbons are recovered using a suitable heat exchange or condensing system (not shown).

Figure 5A:
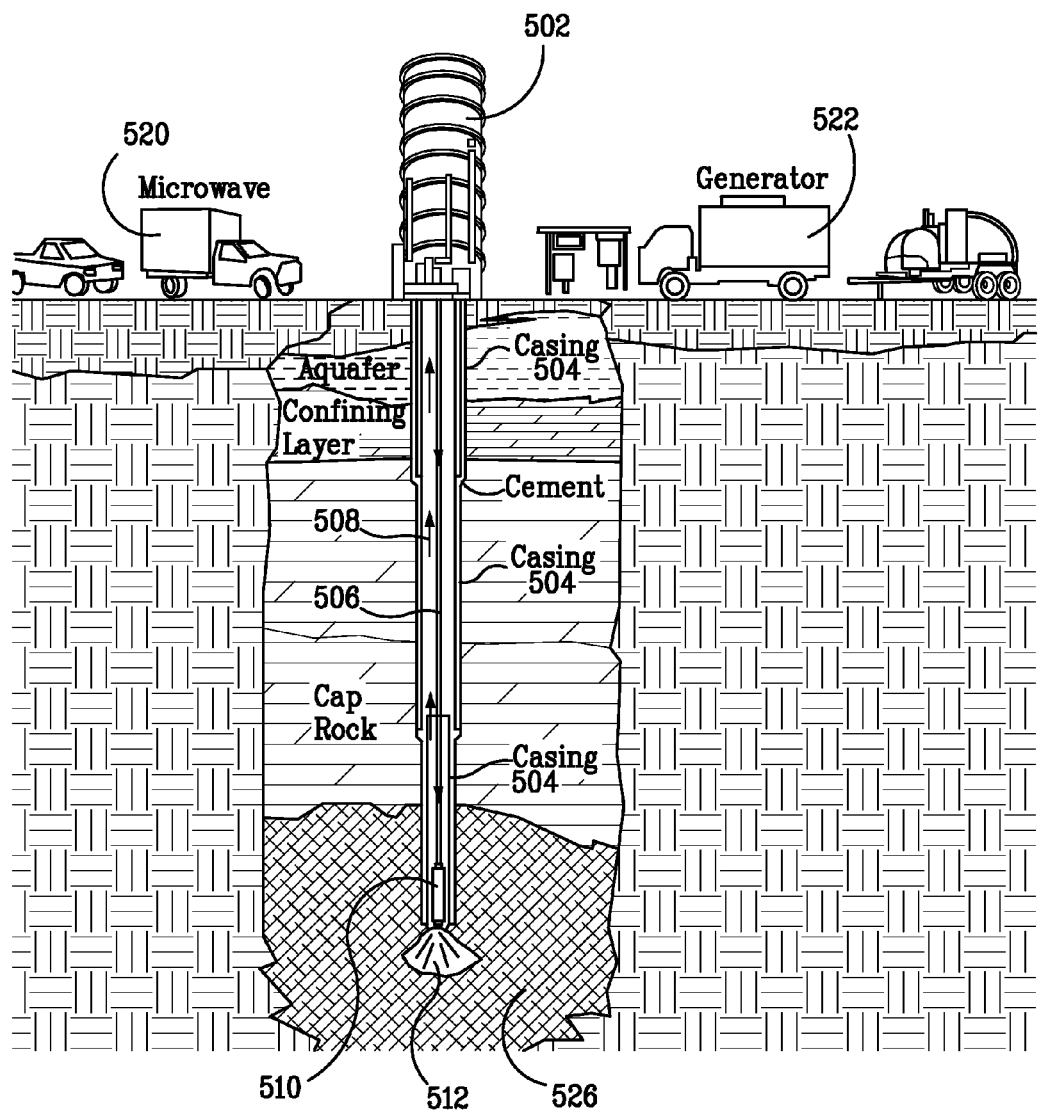
FIG. 5A is an illustration of one embodiment of the present invention for extracting petroleum-based materials from heavy oil contained in oil wells.

FIG. 5A depicts an exemplary embodiment of the present invention for extracting petroleum-based materials, carbon-based materials and hydrocarbon-based materials in situ. A probe capable of generating microwave radiation (e.g., cone, antennae or nozzle) according to the methods of the present invention can be lowered into drilled oil wells. Using the methods of the present invention, the petroleum-based materials can be vaporized and collected at surface-level and processed using techniques known in the art. FIG. 5A illustrates a schematic view of a microwave system for in situ recovery of oil from geologic deposits. A suitable geologic deposit 526 includes an oil well, a capped oil well, a shale rock deposit, a tar sand deposit, a coal deposit, and the like. This illustration depicts a vacuum recovery unit 502 (e.g., a Venturi type system) for recovering geologic hydrocarbons such as fossil fuels from a capped oil well. This system comprises casing 504 extending from the surface of the ground to the geologic carbon deposits at 526. A microwave waveguide is delivered through the casing to the geologic carbon deposit 526. A microwave antenna nozzle 510 resides at the end of the microwave waveguide 506 proximate to the geologic carbon deposit, into which microwaves radiate. On the ground surface is illustrated portable electric generator 522, portable pumping system 524, and portable microwave generation station control unit 520. Hydrocarbon vapors generated by the microwaves in the geologic carbon deposit 526 are transported under vacuum as vaporized geologic carbon deposit (e.g., oil vapor) 508 to the vacuum recovery unit on the surface ground. Capped oil wells contain hydrocarbons that can be cracked to oil, suitable for use as diesel fuel. This involves opening up capped oil wells, optionally adding electron activator into the wells (which aid in absorbing the microwaves and converting the heavy oil in the wells to hydrocarbon vapor), and irradiating the heavy hydrocarbons with microwaves. Once vaporized, the hydrocarbons are readily transported to the surface using suitable vacuum piping, or other plumbing means 528. The vacuum recovery unit 502 is also capable of fractionating the hydrocarbons into other hydrocarbon products. Oils that are difficult to recover using normal pumping means can be recovered according to the processes.

Figure 5B:
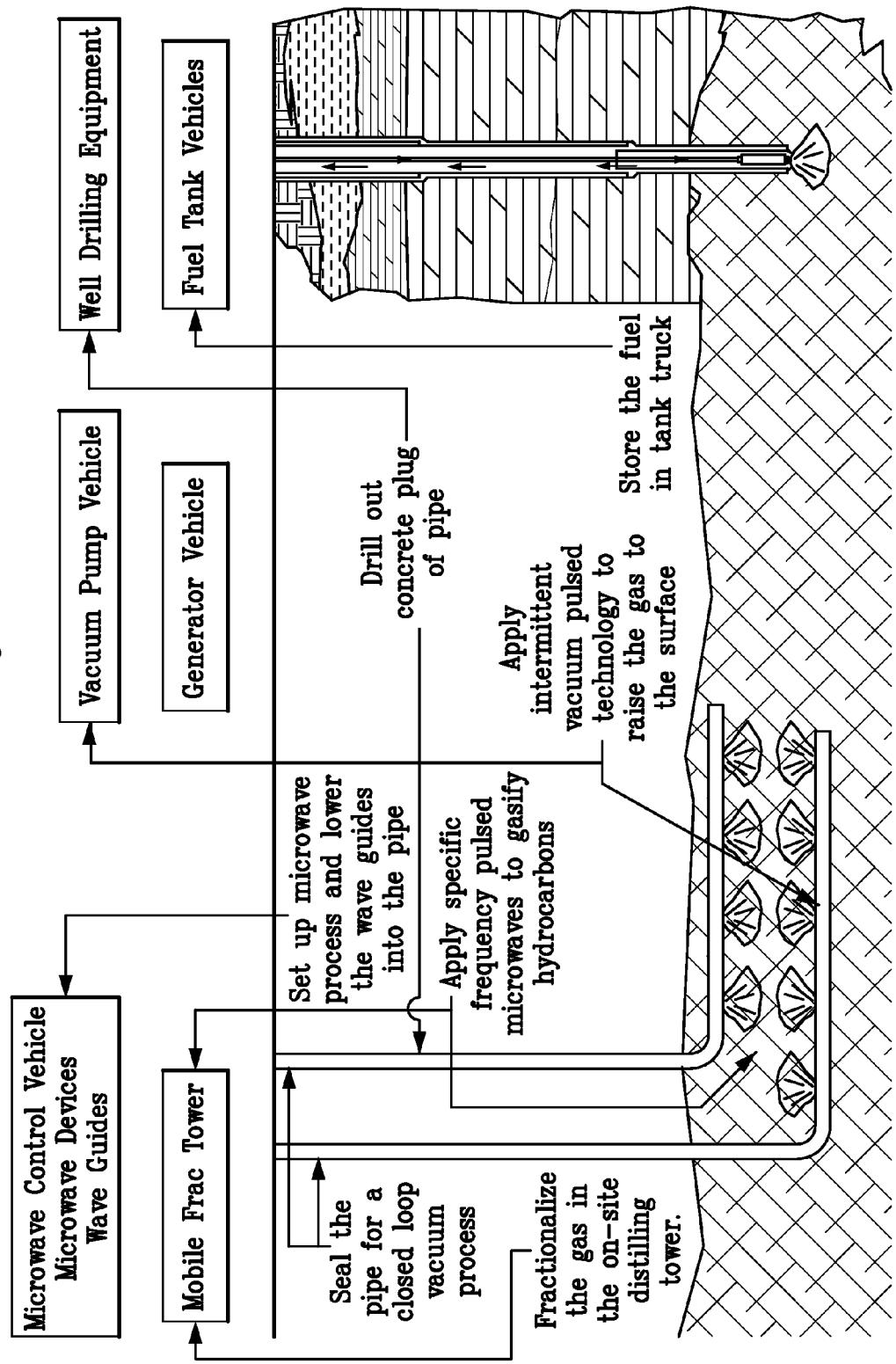
FIG. 5B is an illustration of one embodiment of the present invention for extracting petroleum-based materials from oil shale, in situ.

FIG. 5B depicts an apparatus of the present invention for recovering petroleum-based materials from oil shale, in situ. A probe capable of generating microwave radiation according to the methods of the present invention, can be lowered into oil shale deposits. Using the methods of the present invention, the petroleum-based materials can be vaporized and collected at surface level and processed using techniques known in the art. FIG. 5B illustrates a schematic view of a microwave system for recovering hydrocarbons below ground. In this embodiment, one or more microwave antennae are shown capable of traveling horizontally underground with respect to the ground surface. The microwave antennae are illustrated comprising one or more microwave nozzles for vaporizing hydrocarbon geological deposits in a vacuum environment. FIG. 5B illustrates two conduits (on the left portion of the figure), each containing a plurality of waveguides that terminate it into a suitable microwave nozzle or cone emitter. Suitable microwave cones emitters are commercially available. This process is adapted for recovering residual oil in capped oil wells, and can also be adapted to other geological hydrocarbon deposits such as tar sands and shale rock. If the oil well is "dry" with mainly heavy viscous hydrocarbon material remaining in the well, a microwave antenna is transported down into the oil well and the antenna-end can reside in one or more of the openings. Microwave radiation is directed towards the geologic material in the vicinity of the antenna.

Various hydrocarbon geological deposits can be processed underground using this technology at various depths. Piping for the wells can start at a diameter of about 24 inches at the surface, which diameter is progressively narrower and narrower as sections of piping are added as the depth increases. At a depth of approximately 3000 feet, a typical opening (diameter) of the piping is about 6 inches. For example oil shale deposits in the Western part of the United States are relatively shallow, i.e., near the surface. Strip mines are also relatively shallow, and other deposits may be as deep as 2000 feet or more. Previously pumped oil wells often have chambers of oil that are not readily accessible but require opening by an additional explosive or drilling operation. Certain chambers can also be opened by irradiating the sealing rock material with microwaves. In a laboratory setting, it has been discovered that oil shale pops and reduces in size when irradiated with microwaves. As the oil shale releases hydrocarbons (i.e. oil), the oil shale "pops" like popcorn. Accordingly, directionalizing microwaves within the geological chambers can give rise to breakdown of the geological formation (i.e. the rocks pop, break apart, and fall down and fill the cavity). Accordingly, the antennas can be moved around within geological formations to aid in recovering hydrocarbon material. In some embodiments microwave antennas are placed down about 5000 feet or more, and then are directionalized to travel on the order of approximately 100 yards or so horizontally.

Any type of hydrocarbon material present within the geological formation can be cracked to gas and recovered at the surface using fractionalization condensation units. For example, any carbon suitable for use as diesel fuel can be made by irradiating oil shale. Resulting diesel fuel is suitably used as Cat Diesel Engine Oil. Sometimes oil wells are drilled using directional drilling technologies. Suitable directional drilling technologies are capable of bending at a rate of a degree a foot to create an angle. Accordingly, flexible microwave antennas are suitable for use in such oils. Accordingly, the process includes uncapping a capped oil well. This can be accomplished by drilling out a concrete plug used to cap the well, if present.

The system can include a number of auxiliary equipment located on the surface of the ground. Such equipment includes, for example, well drilling equipment, vacuum pump vehicle, fuel tank vehicles, a generator vehicle, and microwave control vehicle that includes microwave generators, microwave waveguides, and associated equipment. The vacuum pump vehicle can contain a vacuum pump that is capable of applying intermittent vacuum pulse technology to raise hydrocarbon gases to the surface. The hydrocarbon gases are recovered and collected in a suitable distillation tower or fractionation tower that is fitted with heat exchanger and condensing unit. Suitable oil wells and other hydrocarbon geological deposits residing in the ground are accessed via a tube to provide a sealed system with the vacuum pump vehicle for producing the vacuum environment needed for recovering a hydrocarbon vapors. Suitable vacuums include absolute pressures of less than about 20 mm of mercury, or even less than about 40 mm of mercury, or even less than about 100 mm of mercury. The microwave control vehicle contains suitable flexible microwave waveguides and generators. Typically the end of the microwave waveguides (e.g., antennas) are fitted with a suitable microwave cone emitter (e.g., nozzle). The antennas are placed into the mahogany zone in Earth in situ and microwaves are used to radiate tar sands, or oil shale, or other hydrocarbon deposits. The microwaves cause vaporization and gasification of the otherwise viscous and solid-like hydrocarbon and carbon geological sources within the ground. One or more antenna fitted with one or more cone emitter devices can be used.

Figure 5C:
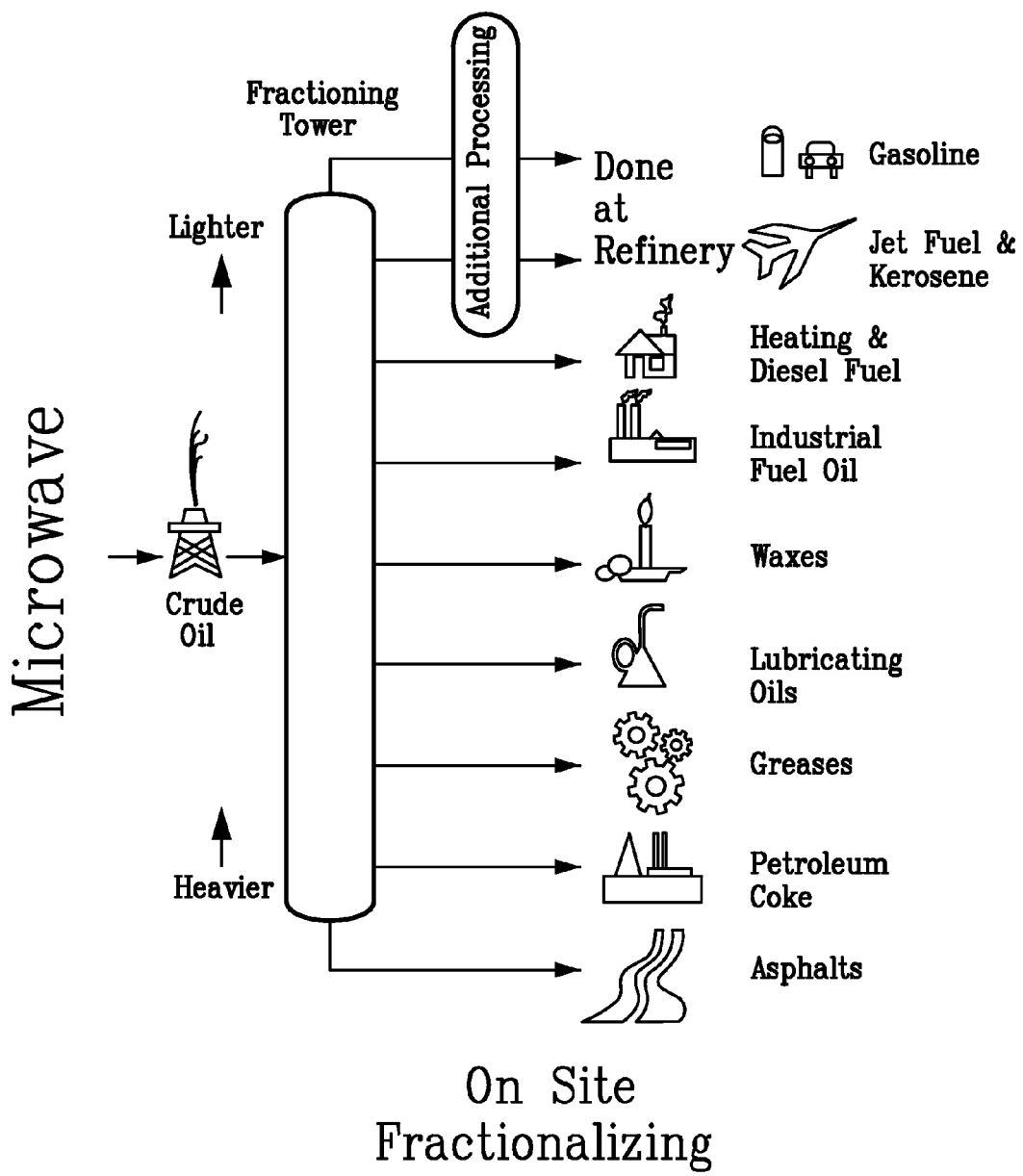
FIG. 5C illustrates the separation of crude oil using a fractionating tower into its component products.

Generated hydrocarbon gases (e.g., take off gases) are transported to a suitable fractionation tower capable of separating the gas, as illustrated in FIG. 5C. Geological material such as sand and rock from which hydrocarbons have been removed remain within the geological formation. In some embodiments, an in situ microwave process is provided. Other embodiments do not require in situ microwave irradiation of the geological formation, e.g., geological material containing hydrocarbons that are mined and provided via separate feed mechanism into a suitable microwave reactor. Geological material such as sand and rock can be substantially totally gasified (i.e., depleted of hydrocarbons and carbons) according to the processes of the present invention, which geological material is then returned to the environment substantially free of hydrocarbons. Finally, fuel and other hydrocarbons recovered form the geological source can be stored in a suitable tanker vehicle and shipped for delivery, further processing, and so on. The recovered hydrocarbons may also be transported by pipeline, rail car, and the like. Optionally, the hydrocarbon vapor recovered from geological sources may be fractionalized on-site using a suitable distillation tower, as illustrated in FIG. 5A. The process of operating a distillation tower is suitably described in FIG. 5C, which illustration shows the separation of crude oil using a fractionating tower into its component products.

Figure 6:
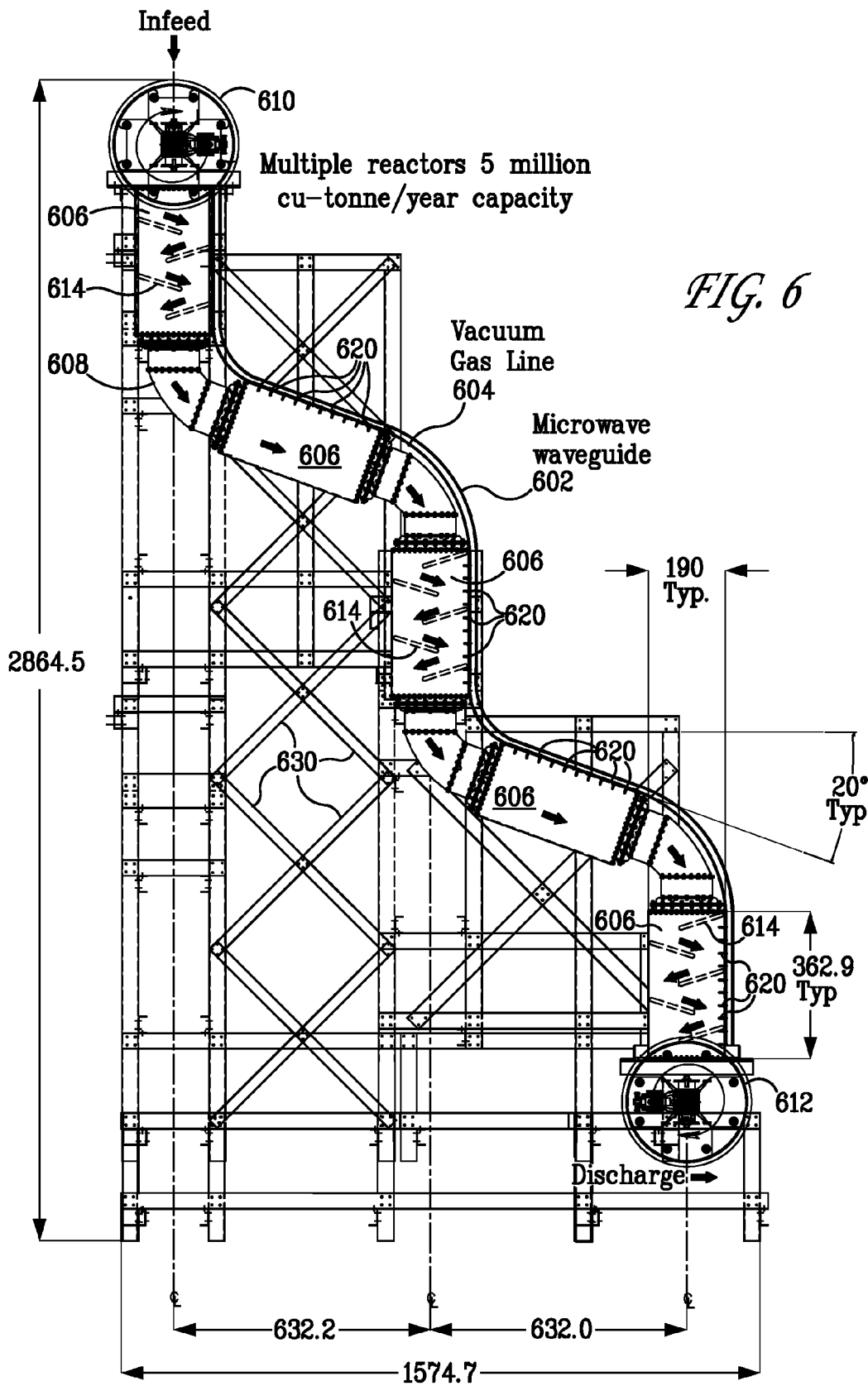
FIG. 6 is an illustration of one embodiment of the present invention for extracting petroleum-based materials from tar sands, oil sands and shale rock.

FIG. 6 depicts one embodiment for extracting petroleum-based materials from shale and tar sands and oil sands. The tar sands can be loaded into the top of the apparatus, which can be under reduced pressure. Using gravity and shaking, the tar sands move through the apparatus while being exposed to microwave radiation as described herein. Vaporized petroleum-based materials can be captured and collected in separate vessels and refined using methods known in the art. After the material has passed through the apparatus, it will be essentially free of petroleum-based materials. FIG. 6 provides an elevation view of a multiple microwave reactor system suitable for high volume recovery of petroleum, carbon and hydrocarbons (e.g. diesel oil) from mined material, e.g., oil shale, oil sands, coal slag, and tar sands. This system is illustrated having the following equipment: microwave waveguide 602; microwave antennas 620; vacuum gas line 604; microwave reactors 606—a total of five connected in series; connecting pipe 608 between microwave reactors 606; top airlock 610 adjacent to in-feed of surface shale and tar sand material; airlock 612 adjacent to discharge of depleted material; baffles 614 within vertically oriented microwave reactors 606; support structure 630 to support multiple microwave reactors connected in series and adjacent to source of surface shale and/or tar sands. Mined material enters the system at airlock in-feed 610, which minimizes the amount of air entering the system. The system is also fitted with a suitable vacuum gas line 604 to maintain a vacuum environment (vacuum pumping equipment not shown) of up to about 20 mm of mercury, or even up to about 40 mm of mercury, or even up to about 100 mm of mercury. Material enters the first microwave reactors 606 adjacent to the airlock, which material is transported along baffles 614 while being irradiated with microwave radiation through microwave antennas 620 (as illustrated in the second through fourth microwave reactors 606). Microwaves irradiate, heat, and crack the hydrocarbons, which hydrocarbons exit the system via a vacuum gas line 604 (connections between the microwave reactors 606 in the vacuum gas line 604 not shown). Geological material leaves the topmost microwave reactor 606 and enters a first connecting pipe 608, which partially reacted material is transported to a second microwave reactor 606. The process is repeated and the material is subsequently transported and irradiated with microwaves as it progresses along the series of microwave reactors and connecting tubes. The processed material eventually arrives at the bottom discharge, where it exits the system through an airlock 612.

Figure 7:
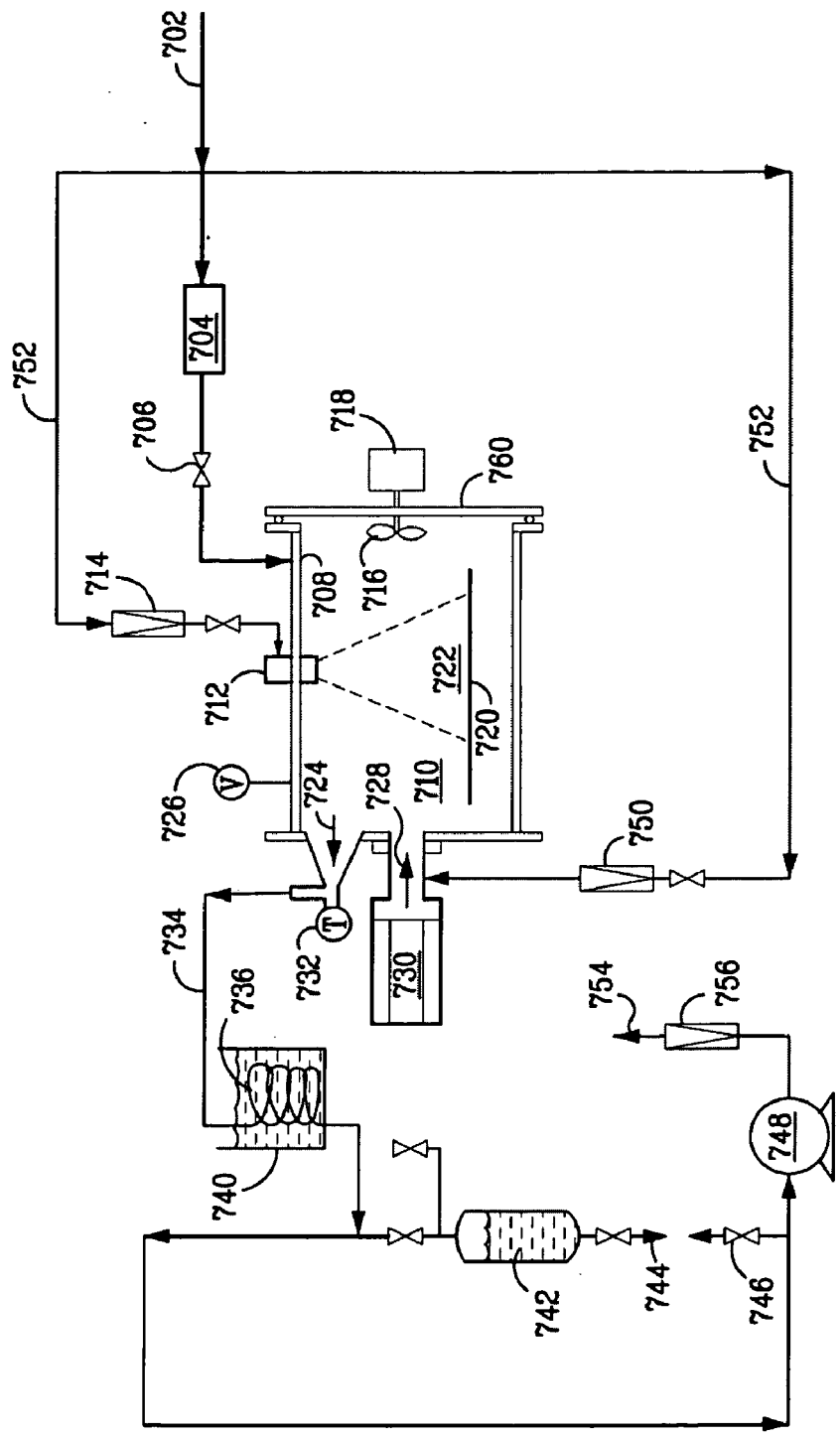
FIG. 7 is an schematic of one embodiment of the present invention for decomposing vehicle tires.

Another embodiment of an apparatus of the present invention is depicted in FIG. 7. FIG. 7 is a schematic view of a microwave reactor chamber and system for recovering fuel oil from a hydrocarbon-containing source, such as used tires. The system includes the following equipment and features: nitrogen supply 702; nitrogen regulator 704; nitrogen flow valve 706; nitrogen inlet 708 to microwave reactor chamber 710; microwave reactor chamber 710; infrared thermocouple 712 to measure average temperature over irradiated area; nitrogen flow meter 714 for infrared thermocouple purge (low flow); microwave scattering reflector 716; motor 718 for microwave scattering reflector 716; platform 720 for holding hydrocarbon containing materials; irradiation area 722; vacuum outlet 724; vacuum gauge 726; opening 728 to microwave antennae; microwave source 730 (TVT or magnetron); temperature gauge 732; vapor transfer tube 734; condenser tube 736; cooling coil 740; oil collector 742; valve drain 744; vacuum bypass valve 746; vacuum pump 748; flow meter 750 for TWT nitrogen purge (flow); nitrogen supply lines 752; exhaust 754; exhaust gas flow meter 756; reactor chamber door 760.

Figure 8A:
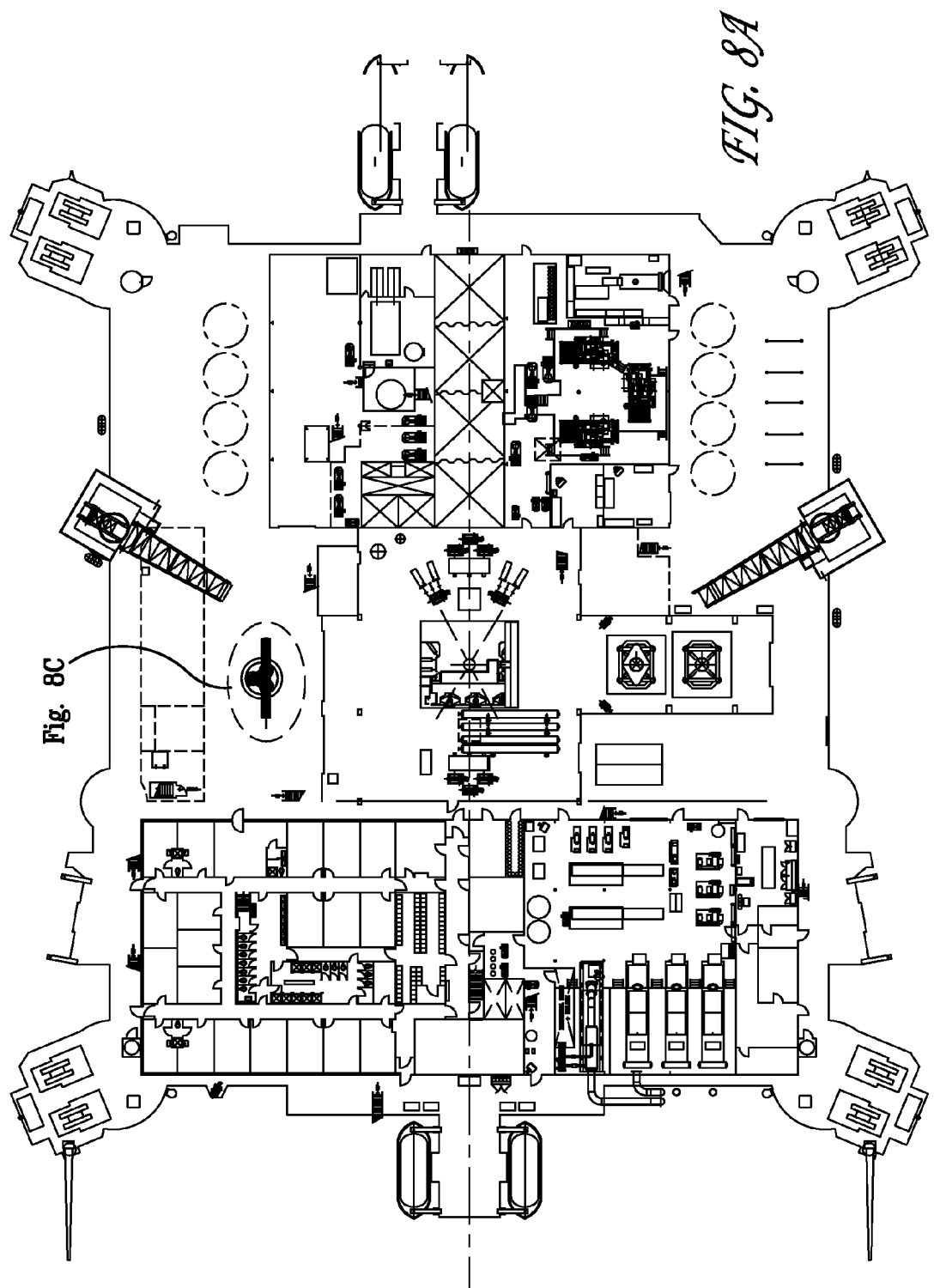
FIG. 8A is a plan view of an oil platform incorporating a drill cuttings microwave processing unit.
Figure 8B:
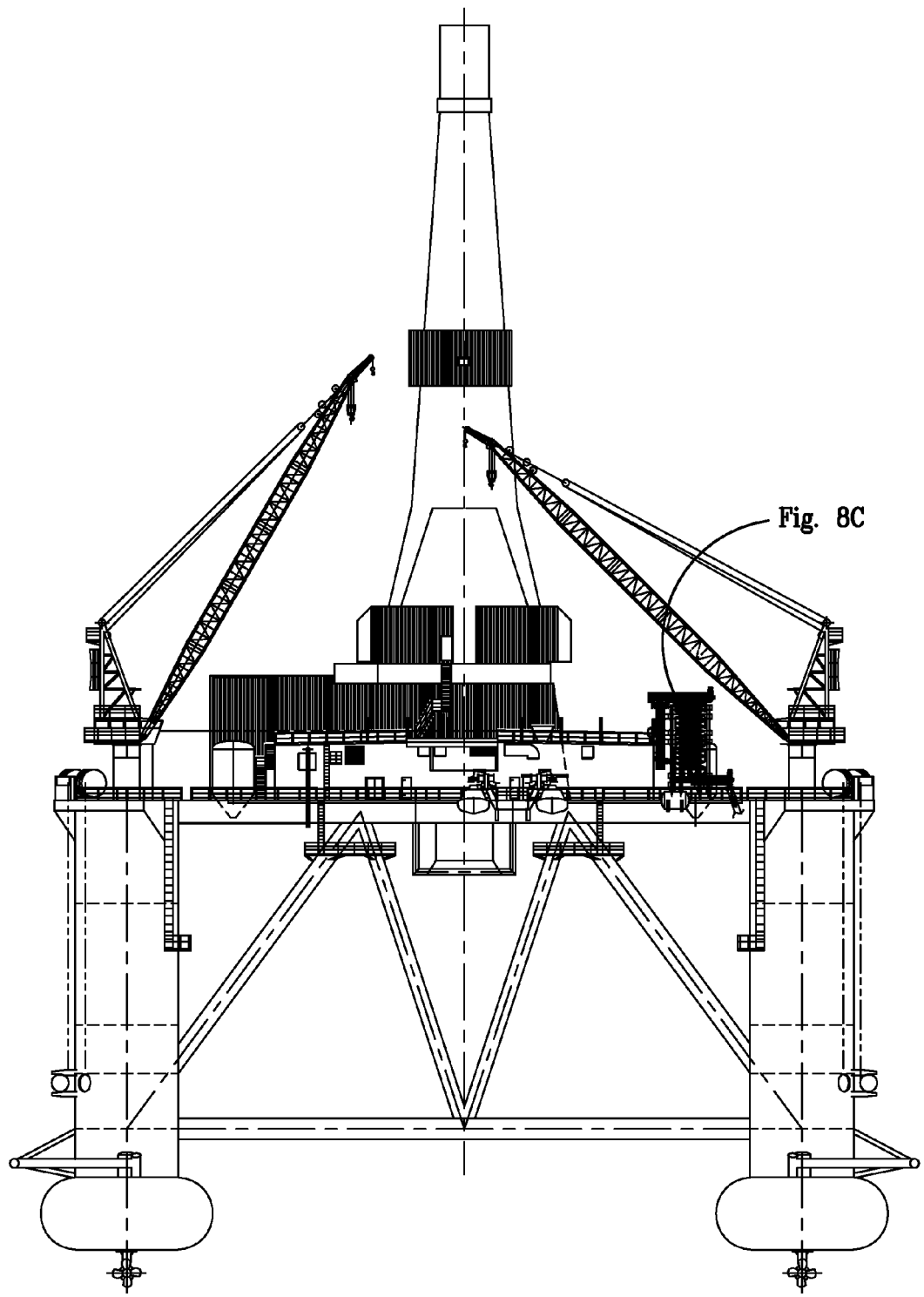
FIG. 8B illustrates an elevation view of the oil platform in FIG. 8A.
Figure 8C:
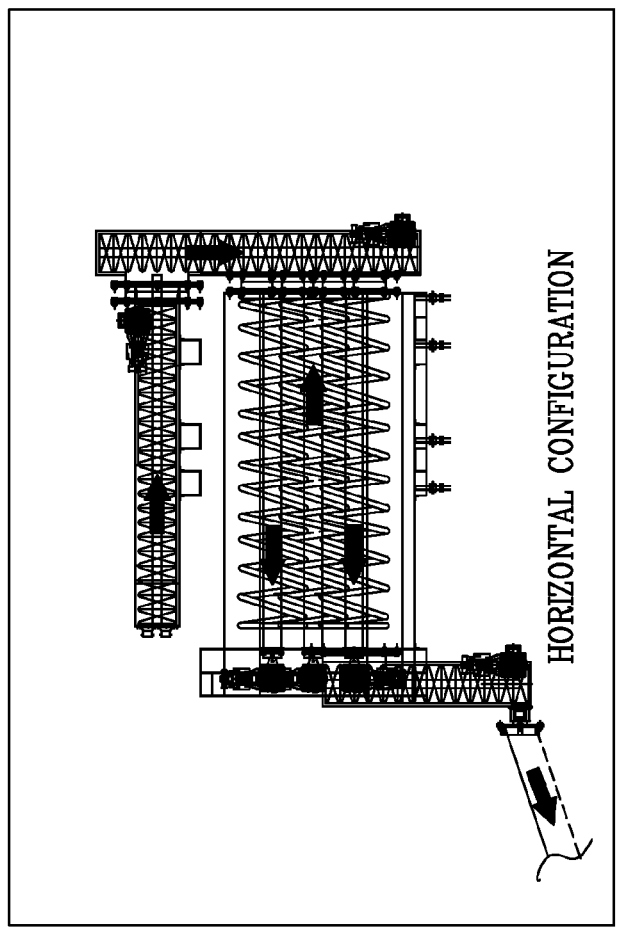
FIG. 8C illustrates a vertical and horizontal configurations of the drill cuttings microwave processing unit suitable for use in the oil platform illustrated in FIG. 8A.
Figure 8C:
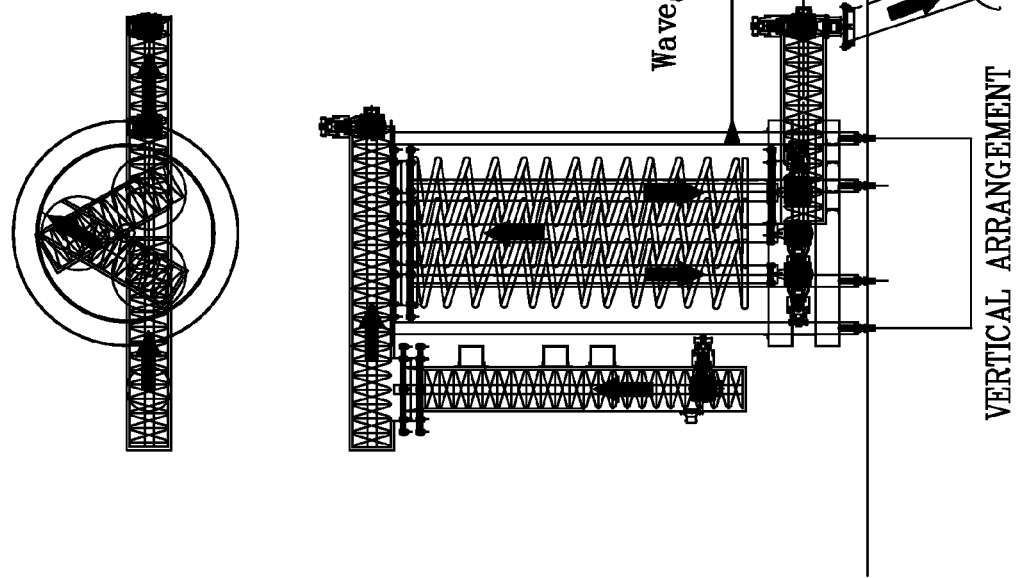

FIGS. 8A, 8B and 8C illustrate an embodiment of the present invention for incorporating a microwave processing system to process drilling cuttings on an oil drilling platform. FIG. 8A is a plan view of an exemplary oil platform incorporating a drill cuttings microwave processing unit. A suitable placement of a microwave processing unit (further illustrated in FIG. 8C) is provided. FIG. 8B illustrates an elevation view of the oil platform in FIG. 8A. FIG. 8C illustrates a vertical and horizontal configurations of the drill cuttings microwave processing unit suitable for use in the oil platform illustrated in FIG. 8A.

Figure 9A:
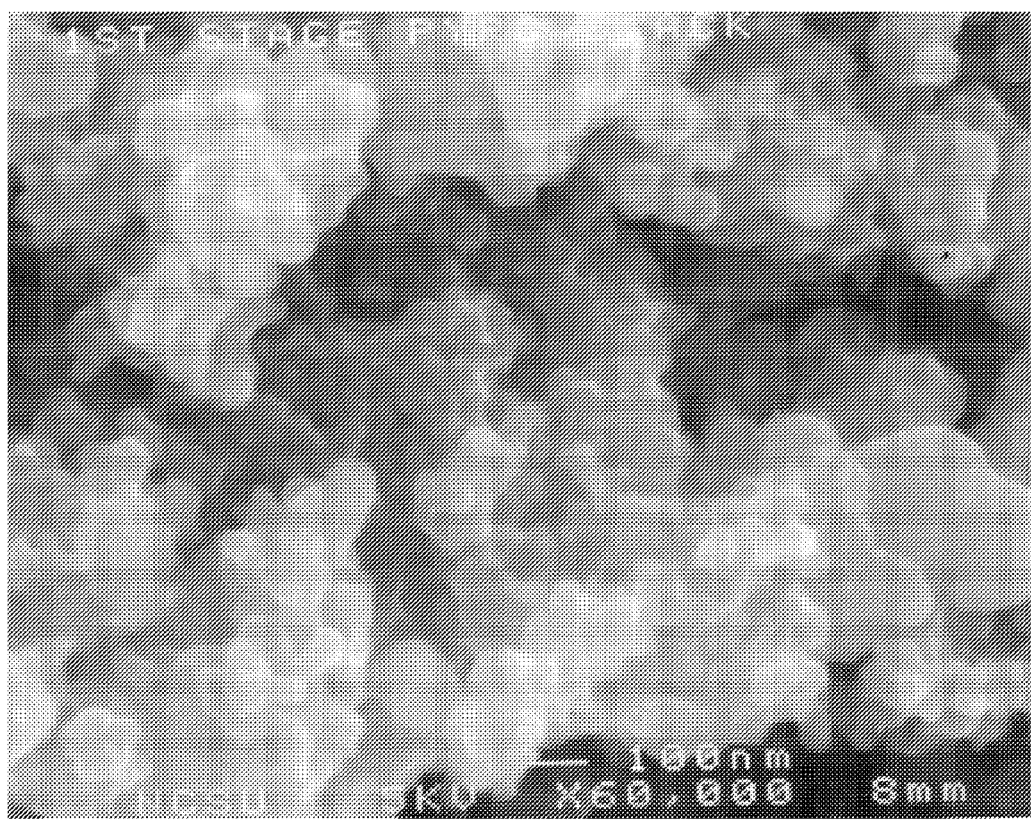
FIG. 9A is a depiction of an electron microscope photograph of carbon black produced by the method of the present invention.
Figure 9B:
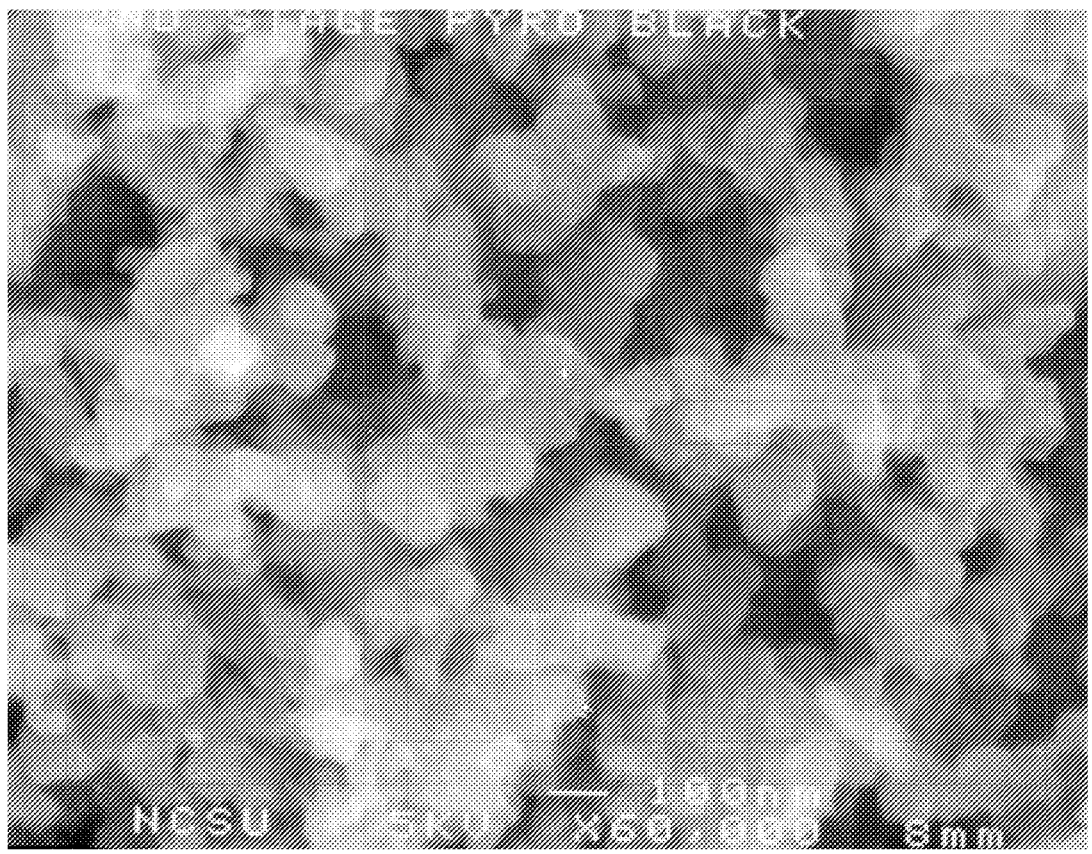
FIG. 9B is a depiction of an electron microscope photograph of carbon black produced by the method of the present invention.
Figure 9C:
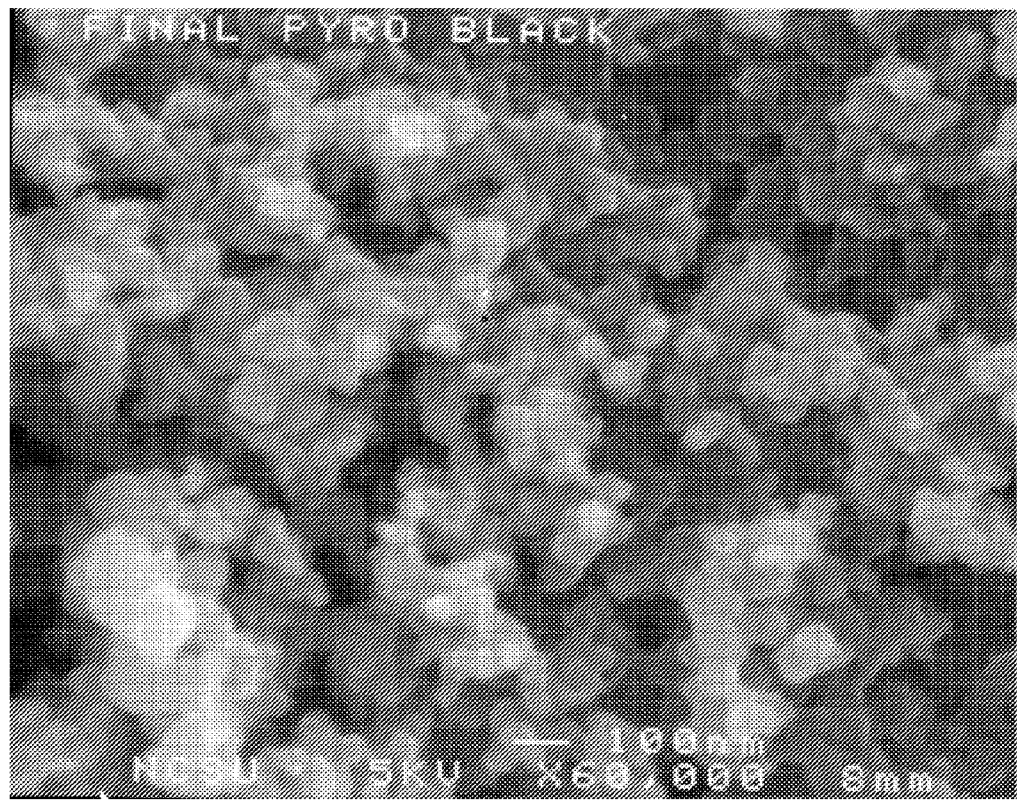
FIG. 9C is a depiction of an electron microscope photograph of carbon black produced by the method of the present invention.

FIGS. 9A-9C are electron microscope photographs at 60,000 times magnification of pyrolytic carbon black material obtained according to Example 3 and using the system illustrated in FIG. 7. The production of this material is further described in Example 3, below.

FIGS. 10A-10E illustrate an additional embodiment of a system for processing materials containing hydrocarbons. Suitable materials include shale rock, drilling cuttings, tar sands, plastics, polymeric materials, recycled hydrocarbon-containing materials, refuse, residual oil, slurry oil, hydrocarbon distillation bottoms, and the like. These figures illustrate the following equipment and features: 1001 microwave tubes, amplifier and waveguides; reactor drum 1004; sealed material in-feed 1002 through reactor drum 1004; in-feed screw 1003; rotating discharge screw 1005; control panel 1006; vacuum pumps 1007; hydraulic drive transmission system 1008 for rotating reactor drum 1004; shipping container 1009; vacuum release support 1010; drum bearing seal 1012; roller bearings 1014; vacuum port 1016; microwave waveguides 1018 entering rotating reactor drum 1004; mixing flight bars 1020 for mixing materials within the rotating reactor drum 1004; bearings 1022 by which mechanism the drum slidably rotates; rotating reactor drum axel 1024 by which mechanism the reactor drum rotates through actuation with the hydraulic drive transmission center 1008.

FIG. 10A is an elevation view of a rotating drum reactor system. Material enters the in-feed 1002 via a suitable source, for example a hopper for receiving chips or chunks of material. The material then enters into the in-feed screw 1003, which meters the material into reactor drum 1004. The material is stirred and mixed using mixing flight bars 1020. The drum is rotated using the hydraulic drive system 1008. The drum reactor is maintained under vacuum by means of vacuum pumps 1007 and vacuum gas line. The reactor drum is vacuum sealed by means of a drum bearing seal 1012 as shown in the inset of FIG. 10D. Microwaves are generated at 1001 and transmitted by a waveguides 1018 into the drum reactor 1004. Hydrocarbon vapors are removed through the vacuum gas line and collected for further processing as described herein above.

Figure 10B:
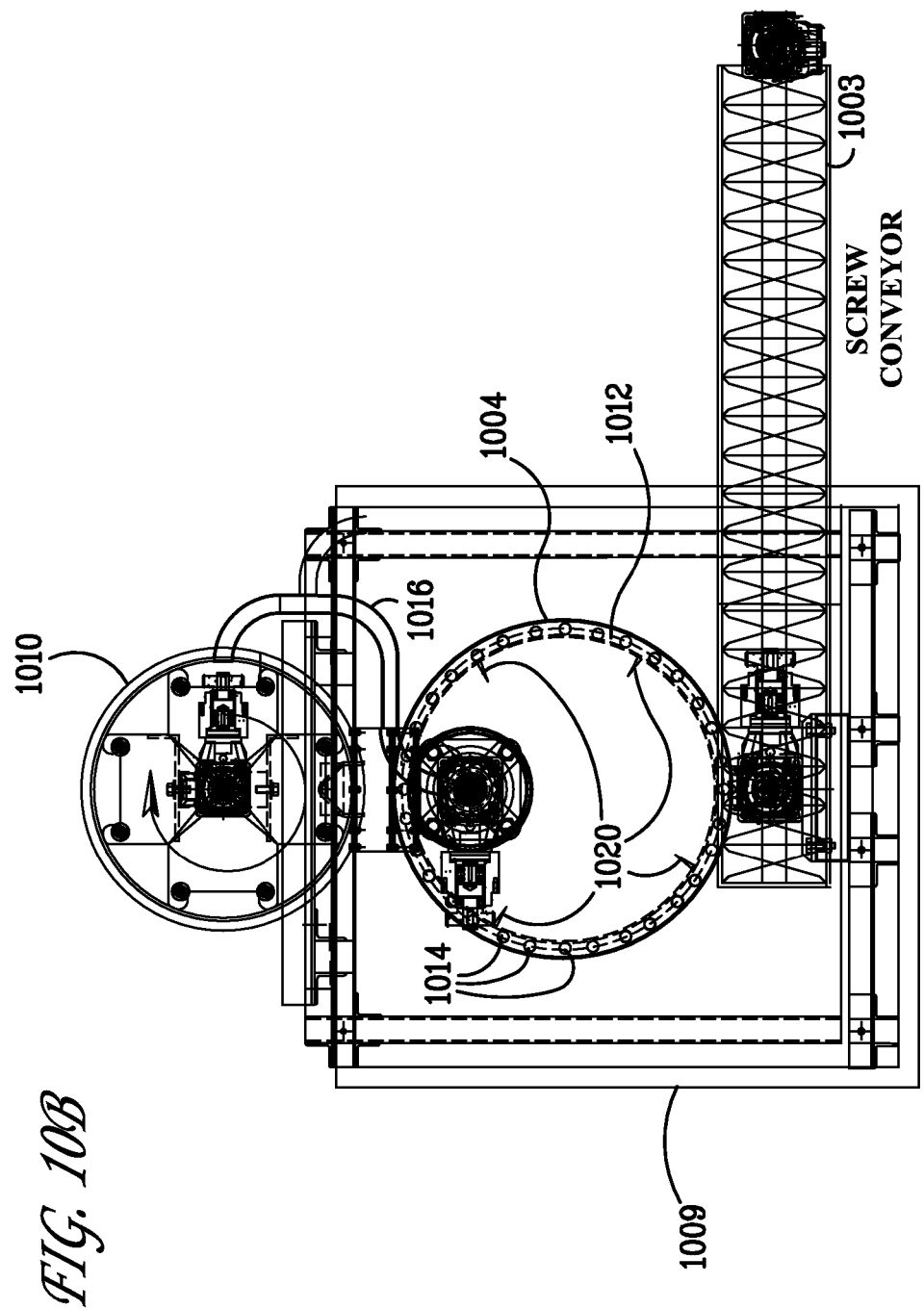
Figure 10C:
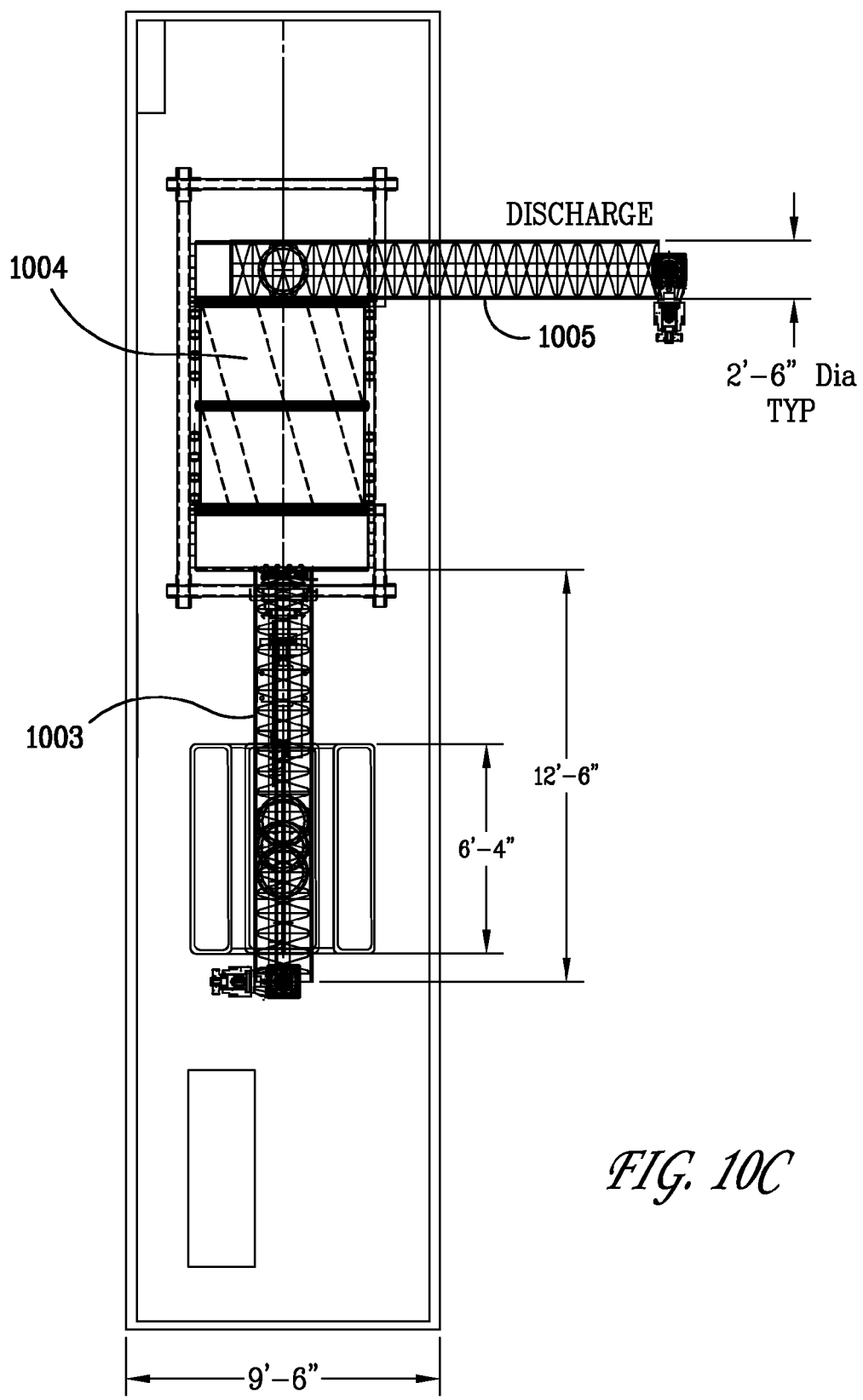

FIG. 10B is a plan view of the rotating drum reactor portion depicted in FIG. 10A. The rotating drum 1004 is shown comprising a drum bearing seal 1012, which drum slidably rotates against end caps comprising ports for microwave antenna and vacuum connections. The reactor drum slides via roller bearings 1014 in the top and bottom end caps. The drum reactor 1004 resides within shipping container 1009. Screw conveyor 1003 conveys material into the drum reactor 1004. FIG. 10C is a plan view of an alternative embodiment of a rotating drum reactor system. FIG. 10D is a cross-sectional view of a drum bearing seal used in the rotating drum reactor system.

Figure 10E:
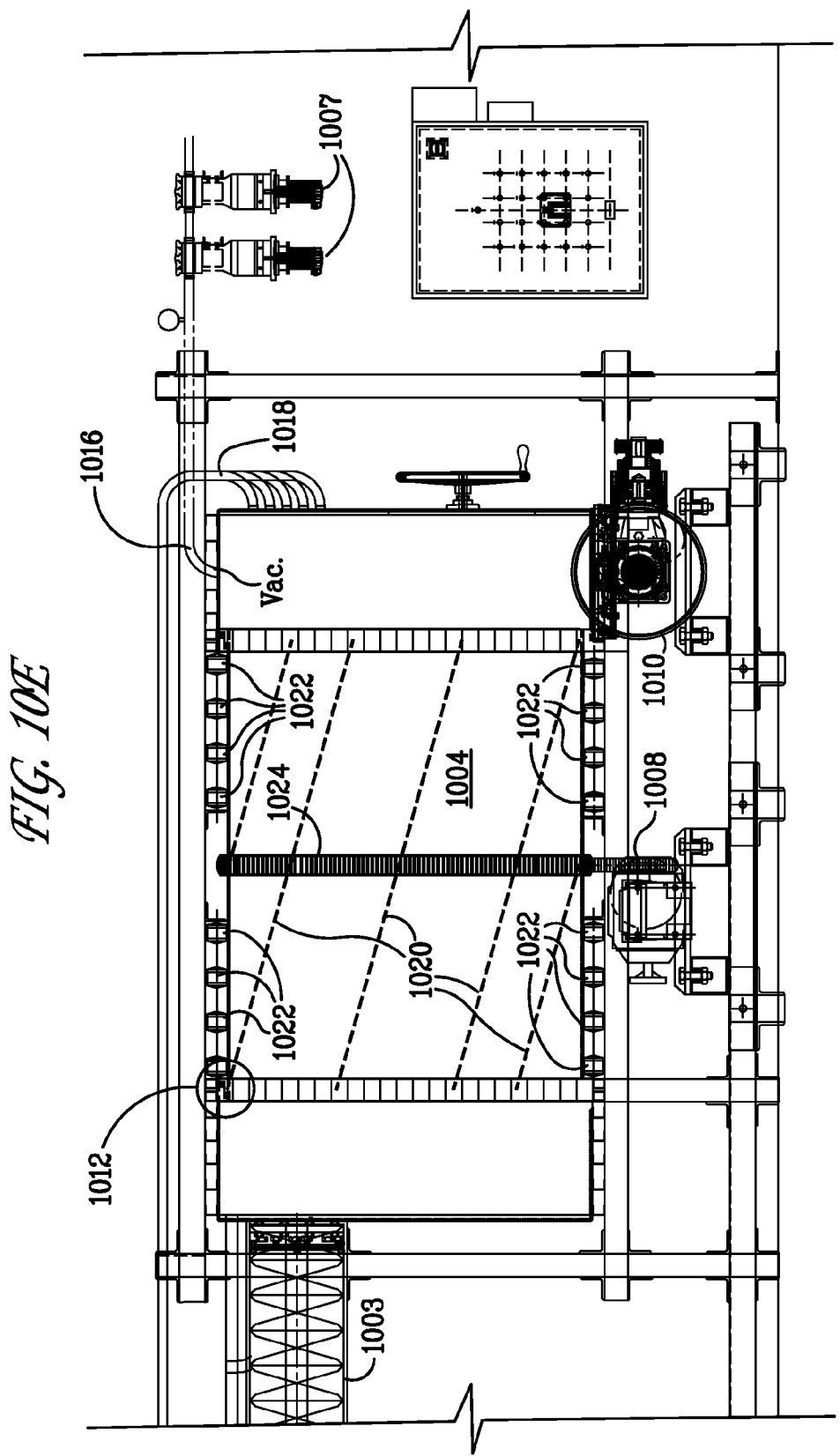

FIG. 10E is an elevation view of the rotating drum reactor portion depicted in FIG. 10A. FIG. 10E further illustrates the in-feed screw 1003 for metering the material into reactor drum 1004, which material is stirred and mixed using mixing flight bars 1020 as the drum is rotated using the hydraulic drive system 1008. The drum reactor is maintained under vacuum by means of vacuum pumps 1007 and vacuum gas line. The reactor drum is vacuum sealed by means of a drum bearing seal 1012 as shown in the inset of FIG. 10D. Microwaves are generated at 1001 and transmitted by waveguides 1018 into the drum reactor 1004. Mixing flight bars 1020 are used for mixing materials within the rotating reactor drum 1004. Bearings 1022 are used for slidably rotating the drum while maintaining the vacuum and microwave antenna connections. The reactor drum rotates by means of axel 1024 through actuation with the hydraulic drive transmission center 1008. Hydrocarbon vapors are removed through the vacuum gas line 1016 and collected for further processing as described herein above. Spent materials substantially depleted of hydrocarbons exit to discharge screw 1005.

As an example, a suitable microwave rotating reactor drum system for extracting hydrocarbons from materials such as drill cuttings and fluids can comprise the following equipment:

A suitable microwave control center includes a number of hydrocarbon specific modular microwave generators, high power amplifiers, master controller module, slave driven power modules, thermal sensors, safety I/O devices for vacuum, interlocks, and emergency shut down, manifold banked configuration of flexible waveguides/windows/adapter plates, thermal metrology gear microwave power measurement instruments and computer control station as per schedule.

A suitable 4'-0" diameter rotating in-feed channel drum unit with vacuum seal provisions comprises ⅜" stainless steel welded frame construction and bolt on stainless steel (replaceable) hardened steel troughs driven by a direct coupled, 5-hp NEMA-4 variable speed (VFD driven) indexing servo-motor to transfer metered product into the feed screw.

A suitable 2'-6" diameter×12'-6" long in-feed screw assembly comprises heavy-duty stainless steel 2" square tubing frame supporting ⅜" stainless steel skins with hardened helical screw driven by a direct coupled, 2-hp NEMA-4 variable speed (VFD) servo-motor to transfer metered product into the reactor vessel.

A suitable 5'-0" diameter×⅜" horizontal seamlessly welded stainless steel and jacketed sub-baric vessel is constructed with internal angular flight bars, (length varies depending on composition of the intended process to) with two—24" long×⅜" stainless steel end cap sections, hardened steel circum-centerline rack & pinion hydraulic transmission driven by a variable speed gear-head motor. Includes a maintenance access door, piping as required to heat vessel jacket, microwave antenna mountings, vacuum port, pressure/flow meters and gauges as required, power transmission is stainless steel guarded. Reactor tank and peripheral equipment is supported by heavy duty stainless steel formed structural channels and heavy duty external bearing wheels.

A suitable 2'-6" diameter×12'-6" long discharge screw assembly comprises heavy-duty stainless steel 2" square tubing frame supporting ⅜" stainless steel skins with hardened helical screw driven by a direct coupled, 2-hp NEMA-4 variable speed (VFD) servo-motor to transfer metered product into the reactor vessel.

A suitable NEMA 4 electrical motor control panel, 480 v/3 ph/60 Hz—24 volt control circuits controls all motors and devices, directly mounted to shipping container wall, includes Allen-Bradley PLC, touch screen diagnostics, VFD drive components, I/O racks, rigid conduit with all marine wire specs, color coded, tagged and match-marked for easy identification.

A suitable vacuum system comprises Dual to Quad (which varies according to throughput) 1.5-hp oil-lubricated, rotary vane vacuum pumps system for −20 in.Hg. continuous duty operation. A vacuum release port system is mounted on the discharge screw section.

Electron activator. It has been discovered that microwave radiation in the frequency range of from about 4 GHz to about 12 GHz is useful for selectively recovering hydrocarbon materials from geological petroleum and mineral sources, as well as manufactured materials such as automobile and truck tires. It has further been found that such materials can comprise carbon particles that absorb energy when irradiated with microwave radiation. The heat from the energized carbon particles is released to the adjacent hydrocarbon materials, and when sufficient heat is released, the hydrocarbons are reduced in molecular weight, i.e., "cracked", and vaporized. Unlike the prior art, the present discovery discloses a particular range of frequencies that is efficacious for the electromagnetic stimulation and heating of carbon particles for recovering hycrocarbons, such as diesel fuel, from difficult to recover hydrocarbon sources.

Disclosed are methods for microwave treatment of difficult-to-recover hydrocarbon source materials comprising contacting the hydrocarbon source material with particles comprising carbon, and subjecting the hydrocarbon source material to microwave radiation. Also disclosed are methods for microwave treatment of hydrocarbon source material comprising contacting the hydrocarbon source material with material having a resonating frequency in the range of from about 4 GHz to about 12 GHz, and subjecting the hydrocarbon source material to microwave radiation characterized as having at least one frequency component that corresponds to the resonating frequency of the material. As used herein, carbon particles or material having a resonating frequency corresponding to the applied microwave radiation frequency are collectively referred to as "electron activator".

In preferred embodiments of the disclosed methods, the microwave radiation is one or more pre-selected microwave radiation frequencies. Preferably, the pre-selected microwave radiation frequency will be the resonating microwave frequency, i.e., the microwave radiation frequency at which the particles comprising carbon absorb a maximum amount of microwave radiation. It has been determined that different compositions of the present invention will absorb more or less microwave radiation, depending on the frequency of the microwave radiation applied. It has also been determined that the frequency at which maximum microwave radiation is absorbed differs by composition. By using methods known in the art, a composition of the present invention can be subjected to different frequencies of microwave radiation and the relative amounts of microwave radiation absorbed can be determined. Preferably, the microwave radiation selected is the frequency that comparatively results in the greatest amount of microwave radiation absorption. In one embodiment, the pre-selected microwave radiation frequency is characterized as having at least one frequency component in the range of from about 4 GHz to about 12 GHz. In other embodiments, the pre-selected microwave radiation frequency is characterized as having at least one frequency component in the range of from about 5 GHz to about 9 GHz, from about 6 GHz to about 8 GHz, or from about 6.5 GHz to about 7.5 GHz.

The particles comprising carbon are preferably carbon substances that have a resonating microwave frequency of from about 4 GHz to about 12 GHz. Many forms of carbon are known by those skilled in the art, and, while not intending to exclude other carbon types, it is contemplated that any form of carbon having a resonating microwave frequency of from about 4 GHz to about 12 GHz will be within the scope of the present invention. For example, the particles comprising carbon can comprise carbon black. Carbon black may be described as a mixture of incompletely-burned hydrocarbons, produced by the partial combustion of natural gas or fossil fuels.

Carbon blacks have chemisorbed oxygen complexes (e.g., carboxylic, quinonic, lactonic, phenolic groups and others) on their surfaces to varying degrees depending on the conditions of manufacture. These surface oxygen groups are collectively referred to as the volatile content. In preferred embodiments, the present invention uses carbon black having a moderate volatile content. The volatile content of the preferred carbon black can be composed of hydrocarbons having up to about 20 carbon atoms, or even up to about 30 carbon atoms.

The constituent parts of the electron activator preferably have characteristic dimensions in the micrometer range, although other particle or fragment sizes may also be used. Because carbon particles or particles comprising another electron activator for use in the present invention can be present in numerous configurations, and can be irregular in shape, the term "characteristic dimensions" is used herein to describe the long axis in the case of substantially cylindrical or otherwise oblong particles, and to describe diameter in the case of substantially spherical particles, etc. In some embodiments wherein the carbon particles comprise carbon black, the particles can have characteristic dimensions of about 10 nm to about 250 µm. In other embodiments, the particles can have characteristic dimensions of about 100 nm to about 100 µm, or of about 200 nm to about 10 µm.

Preferred are electron activators having characteristic dimensions that are conducive to ready dispersion within hydrocarbon materials that are targeted for vaporization. The electron activators can be contacted with the hydrocarbon materials by directly introducing the electron activators into the hydrocarbon materials environment.

In the present systems, the electron activator particles can comprise any material that is capable of absorbing at least a portion of the transmitted microwave radiation generated by the microwave generator. In preferred embodiments the material comprises carbon. The particles comprising carbon are preferably carbon substances that have a resonating microwave frequency of from about 4 GHz to about 12 GHz. Many forms of carbon are known by those skilled in the art, and, while not intending to exclude other carbon types, it is contemplated that any form of carbon having a resonating microwave frequency of from about 4 GHz to about 12 GHz will be within the scope of the present invention. For example, the particles comprising carbon can comprise carbon black. Carbon blacks have chemisorbed oxygen complexes (e.g., carboxylic, quinonic, lactonic, phenolic groups and others) on their surfaces to varying degrees depending on the conditions of manufacture. These surface oxygen groups are collectively referred to as the volatile content. In preferred embodiments, the present invention uses carbon black having a moderate volatile content prepared by processing tire chips using microwave radiation as described herein above.

The constituent parts of the particles preferably have characteristic dimensions in the micrometer range, although other particle or fragment sizes may also be used. Because carbon particles or particles comprising another electron activator for use in the present invention can be present in numerous configurations, and can be irregular in shape, the term "characteristic dimensions" is used herein to describe the long axis in the case of substantially cylindrical or otherwise oblong particles, and to describe diameter in the case of substantially spherical particles, etc. In some embodiments wherein the carbon particles comprise carbon black, the particles can have characteristic dimensions of about 100 µm.

EXAMPLES

The following examples are provided to further describe the present invention. They are not to be construed to limit the scope of the invention described in the claims. Many of the examples make use of the apparatus substantially illustrated and described in FIG. 7.

Example 1

A chamber capable of being subjected to between 4.0 to 12.0 GHz of microwave radiation frequencies and rated to withstand reduced atmospheric pressure, was equipped with a 700 W, 5.8 to 7.0 GHz VFM microwave tube (Lambda Technologies, Morrisville, N.C.). The chamber was outfitted with a nitrogen gas inlet tube, a vacuum inlet tube, and an outlet tube connected to a heat exchanger and collection vessel. The chamber was also equipped with an infrared thermocouple temperature probe.

Example 2

A chamber capable of being subjected to between 4.0 to 12.0 GHz of microwave radiation frequencies and rated to withstand reduced atmospheric pressure, was equipped with a 1800 W, 7.3 to 8.7 GHz VFM microwave tube (Lambda Technologies, Morrisville, N.C.). The chamber was outfitted with an nitrogen gas inlet tube, a vacuum inlet tube, and an outlet tube connected to a heat exchanger and collection vessel. The chamber was also equipped with an infrared thermocouple temperature probe.

Example 3

A 20 lb automobile tire was cut into approximately 4"×4" pieces. These pieces were washed and dried. The pieces were placed on a tray and loaded into the chamber of Example 1. Twenty psi of $N_2$ was introduced into the chamber. The VFM microwave radiation was initiated (700 W, 5.8-7.0 GHz). When the temperature of the tire pieces reached 465° F., the microwave radiation was halted and the tire pieces allowed to cool about 5-25° F. Microwave radiation was resumed. This process was repeated an additional three times. Total experiment run time was approximately twelve minutes. The decomposition products were then analyzed.

This experiment produced 1.2 gallons of #4 oil (see Tables 1 and 2), 7.5 lbs of carbon black, 50 cu. ft. of combustible gases (including methane, ethane, propane, butane, and isobutene), and 2 lbs of steel. FIGS. 9A-9C depict electron microscope photographs of samples of carbon black produced using this method. FIG. 9C demonstrates that the carbon black produced by this method is comparable to commercial-grade rubber black.

TABLE 1

Analysis of Oil Produced by Example 3.

| TEST | RESULT |
| --- | --- |
| Gross Heat of Combustion | 18308 BTU/lb |
| Gross Heat of Combustion | 144688 BTU/gal |
| Sulfur | 0.931 wt. % |
| Kinematic Viscosity @ 122° F. | 9.773 cSt |
| Saybolt Furol Viscosity @ 122° F. | 78.9 sus |
| Sediment by Extraction | 0.02 wt. % |
| Ash @ 775° C. | 0.024 wt. % |
| Nitrogen | 0.43 wt. % |

Samples were tested by ITS Caleb Brett, Deer Park, TX. Samples were filtered through a 100 mesh filter prior to testing.

TABLE 2

Analysis of Oil Produced by Example 3

| TEST | RESULT |
| --- | --- |
| Corrected Flash Point | 92° C. |
| Corrected Flash Point | 198° F. |
| API Gravity 15.56° C., 60° F. | 13.7° API |

Samples were tested by ITS Caleb Brett, Deer Park, TX.

Example 4

A sample of oil cuttings, oil shale, tar sands, oil sands, slurry oil, and/or a material contaminated with petroleum-based materials, is placed in the apparatus of Example 2. The pressure is reduced to 20 Torr. Microwave radiation is applied to the sample for a time sufficient to vaporize all the petroleum-based material in the sample. At 20 Torr, the petroleum-based materials vaporize between about 400 and 520° F. The vaporized petroleum-based materials are cooled and collected in a collection vessel. The material remaining in the chamber is substantially free of petroleum-based material.

Example 5

A plastic bottle was placed in the apparatus of Example 1 and exposed to microwave radiation. The exposure to microwave radiation resulted in complete vaporization of the bottle and recovery of petroleum-based materials.

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for decomposing a composition comprising a petroleum-based material, comprising:
    subjecting said composition to microwave radiation for a time sufficient to at least partially decompose said composition,
        wherein said microwave radiation comprises at least one frequency component in the range of from about 4 GHz to about 18 GHz; and
    recovering decomposed petroleum-based material at a pressure less than one atmosphere, wherein said composition is derived from a tire.

2. The method of claim 1, wherein said composition is decomposed to form at least one of oil, gas, steel, sulfur, and carbon black.

3. A method for decomposing a composition comprising a petroleum-based material, comprising:
    subjecting said composition to microwave radiation for a time sufficient to at least partially decompose said composition,
        wherein said microwave radiation comprises at least one frequency component in the range of from about 4 GHz to about 18 GHz; and
    recovering decomposed petroleum-based material at a pressure less than one atmosphere, wherein said composition comprises plastic.

4. The method of claim 3, wherein said plastic comprises ethylene (co)polymer, propylene (co)polymer, styrene (co) polymer, butadiene (co)polymer, polyvinyl chloride, polyvinyl acetate, polycarbonate, polyethylene terephthalate, (meth)acrylic (co)polymer, or a mixture thereof.

5. The method of claim 3, wherein said composition is decomposed to form at least one monomer.

6. A method for decomposing a composition comprising a petroleum-based material, comprising:
    subjecting said composition to microwave radiation for a time sufficient to at least partially decompose said composition, wherein the temperature of said composition does not exceed about 700° F.;
        wherein said microwave radiation comprises at least one frequency component in the range of from about 4 GHz to about 18 GHz; and
    recovering decomposed petroleum-based material at a pressure less than one atmosphere.

7. The method of claim 6, wherein said composition is exposed to less than about 12% oxygen.

8. The method of claim 6, wherein said composition is exposed to less than about 8% oxygen.

9. The method of claim 6, wherein said composition is exposed to an inert gas atmosphere.

10. The method of claim 6, wherein said microwave radiation comprises at least one frequency component in the range of from 4.0 GHz to about 12 GHz.

11. The method of claim 6, wherein said composition is exposed to less than atmospheric pressure.

12. The method of claim 6, wherein said composition is exposed to a pressure of less than about 40 Torr.

13. The method of claim 6, wherein said composition is exposed to a pressure of less than 20 Torr.

14. The method of claim 6, wherein said composition is exposed to a pressure of less than 5 Torr.

15. The method of claim 6, wherein the temperature of said composition does not exceed about 500° F.

16. The method of claim 6, wherein the temperature of said composition does not exceed about 465° F.

17. The method of claim 6, wherein said microwave radiation comprises one or more pre-selected microwave radiation frequencies.

18. The method of claim 17, wherein said one or more pre-selected microwave radiation frequencies is in the range of from about 4.0 and about 7.2 GHz.

19. The method of claim 17, wherein said one or more pre-selected microwave radiation frequencies is in the range of from about 4.0 and about 6.0 GHz.

20. The method of claim 6, wherein said microwave radiation comprises a sweeping range of microwave radiation frequencies.

21. The method of claim 20, wherein the range of microwave radiation frequencies comprises a bandwidth of about 4 GHz.

22. The method of claim 20, wherein the range of frequencies of said radiation is in the C-Band frequency range.

23. The method of claim 20, wherein the range of frequencies of said radiation is in the X-Band frequency range.

24. The method of claim 20, wherein the frequencies of said radiation is in the range of from about 5.8 GHz to about 7.0 GHz.

25. The method of claim 20, wherein the frequencies of said radiation is in the range of from about 7.9 GHz to about 8.7 GHz.

26. The method of claim 20, wherein the sweeping range of microwave radiation frequencies encompasses one or more pre-selected microwave radiation frequencies.

27. The method of claim 26, wherein the range of microwave radiation frequencies is about +/−2 GHz of the pre-selected microwave radiation frequency.

* * * * *